United States Patent
Daugherty et al.

(10) Patent No.: US 10,544,410 B2
(45) Date of Patent: *Jan. 28, 2020

(54) POLYPEPTIDE DISPLAY LIBRARIES AND METHODS OF MAKING AND USING THEREOF

(71) Applicant: The Regents of the University of California, Oakland, CA (US)

(72) Inventors: Patrick S. Daugherty, Santa Barbara, CA (US); Paul H. Bessette, Camarillo, CA (US); Jeffrey Rice, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/005,583

(22) Filed: Jun. 11, 2018

(65) Prior Publication Data

US 2019/0264194 A1    Aug. 29, 2019

Related U.S. Application Data

(60) Continuation of application No. 14/821,580, filed on Aug. 7, 2015, now Pat. No. 10,041,063, which is a continuation of application No. 13/722,915, filed on Dec. 20, 2012, now Pat. No. 9,134,309, which is a continuation of application No. 12/563,897, filed on Sep. 21, 2009, now Pat. No. 8,361,933, which is a continuation of application No. 11/612,757, filed on Dec. 19, 2006, now Pat. No. 7,612,019, which is a division of application No. 10/920,244, filed on Aug. 18, 2004, now Pat. No. 7,256,038.

(60) Provisional application No. 60/495,698, filed on Aug. 18, 2003.

(51) Int. Cl.
| | | |
|---|---|---|
| C12N 15/10 | (2006.01) | |
| C07K 14/245 | (2006.01) | |
| G01N 33/554 | (2006.01) | |
| C40B 40/10 | (2006.01) | |
| C40B 30/04 | (2006.01) | |

(52) U.S. Cl.
CPC ........ *C12N 15/1037* (2013.01); *C07K 14/245* (2013.01); *C12N 15/1044* (2013.01); *G01N 33/554* (2013.01); *C40B 30/04* (2013.01); *C40B 40/10* (2013.01)

(58) Field of Classification Search
CPC ............ C12N 15/1037; C12N 15/1044; C07K 14/245; G01N 33/554; C40B 30/04; C40B 40/10
See application file for complete search history.

(56) References Cited

U.S. PATENT DOCUMENTS

| | | |
|---|---|---|
| 5,571,698 A | 11/1996 | Ladner et al. |
| 5,962,255 A | 10/1999 | Griffiths et al. |
| 5,990,275 A | 11/1999 | Whitlow et al. |
| 6,300,065 B1 | 10/2001 | Kieke et al. |
| 6,303,344 B1 | 10/2001 | Patten et al. |
| 6,423,538 B1 | 7/2002 | Wittrup et al. |
| 6,492,160 B1 | 12/2002 | Griffiths et al. |
| 6,548,249 B1 | 4/2003 | Anderson et al. |
| 6,660,257 B1 | 12/2003 | McWherter et al. |
| 6,660,843 B1 | 12/2003 | Feige et al. |
| 6,696,251 B1 | 2/2004 | Wittrup et al. |
| 6,699,658 B1 | 3/2004 | Wittrup et al. |
| 6,723,512 B2 | 4/2004 | Larocca et al. |
| 7,256,038 B2 | 8/2007 | Daugherty et al. |
| 7,612,019 B2 | 11/2009 | Daugherty et al. |
| 7,666,817 B2 | 2/2010 | Daugherty et al. |
| 8,293,685 B2 | 10/2012 | Daugherty et al. |
| 8,361,933 B2 | 1/2013 | Daugherty et al. |
| 9,062,107 B2 | 6/2015 | Daugherty et al. |
| 9,121,828 B2 | 9/2015 | Daugherty et al. |
| 9,134,309 B2 | 9/2015 | Daugherty et al. |
| 9,234,847 B2 | 1/2016 | Daugherty et al. |
| 9,309,510 B2 | 4/2016 | La Porte et al. |
| 9,695,415 B2 | 7/2017 | Daugherty et al. |
| 10,017,757 B2 | 7/2018 | Daugherty et al. |
| 10,041,063 B2 | 8/2018 | Daugherty et al. |
| 2003/0013150 A1 | 1/2003 | Manosroi et al. |
| 2003/0049729 A1 | 3/2003 | Manosroi et al. |
| 2003/0082575 A1 | 5/2003 | Schultz et al. |
| 2004/0146976 A1 | 7/2004 | Wittrup et al. |
| 2005/0047461 A1 | 3/2005 | Kihara et al. |
| 2005/0196406 A1 | 9/2005 | Daugherty et al. |

(Continued)

FOREIGN PATENT DOCUMENTS

| | | |
|---|---|---|
| EP | 0474891 | 3/1992 |
| EP | 0474894 | 3/1992 |

(Continued)

OTHER PUBLICATIONS

Ahmed, et al. (2006) "Vascular Endothelial Growth Factor (VEGF) Inhibition by Small Molecules" J. Chemother. 16(Suppl. 4):59-63.

(Continued)

*Primary Examiner* — Robert H Havlin
(74) *Attorney, Agent, or Firm* — Edward J. Baba; Bozicevic, Field & Francis LLP

(57) ABSTRACT

Disclosed herein are expression vectors which display a passenger polypeptide on the outer surface of a biological entity. As disclosed herein the displayed passenger polypeptide is capable of interacting or binding with a given ligand. Also disclosed are methods of making and using the expression vectors. N/C terminal fusion expression vectors and methods of making and using are also disclosed.

17 Claims, 28 Drawing Sheets

Specification includes a Sequence Listing.

(56) References Cited

U.S. PATENT DOCUMENTS

| | | |
|---|---|---|
| 2006/0003387 A1 | 1/2006 | Peelle et al. |
| 2006/0029947 A1 | 2/2006 | Georgiou et al. |
| 2007/0020678 A1 | 1/2007 | Ault-Riche et al. |
| 2016/0010082 A1 | 1/2016 | Daugherty et al. |
| 2016/0010084 A1 | 1/2016 | Daugherty et al. |

FOREIGN PATENT DOCUMENTS

| | | |
|---|---|---|
| EP | 0922957 | 6/1999 |
| WO | WO 1998017810 | 4/1998 |
| WO | WO 2005047461 | 5/2005 |
| WO | WO 2007027935 | 3/2007 |
| WO | WO 2009014726 | 1/2009 |
| WO | WO 2014026136 | 2/2014 |

OTHER PUBLICATIONS

Ascheim, et al., Clipping away at protease substrates, Nature Biothnology, 2006, vol. 24, No. 6, pp. 665.

Baird, et al. (1999) "Circular Permutation and Receptor Insertion within Green Fluorescent Proteins" Proc. Natl. Acad. Sci. U.S.A. 96(20):11241-11246.

Beebe, et al. (2003)"Pharmacological Characterization of CP-547,632, a Novel Vascular Endothelial Growth Factor Receptor-2 Tyrosine Kinase Inhibitor for Cancer Therapy" Cancer Res. 63(21):7301-7309.

Bergsland, et al. (2004) "Vascular Endothelial Growth Factor as a Therapeutic Target in Cancer" Am. J. Health Syst. Pharm. 61(21 Suppl. 5): S4-S11.

Bessette, et al., Flow Cytometric Screening of cDNA Expression Libraries for Fluorescent Proteins, Biotechnology Progress, vol. 20, Issue 3, pp. 963-967, 2004.

Bessette, et al., Rapid isolation of high-affinity protein binding peptides using bacterial display, Protein Engineering, Design and Selection (2004) 17 (10): 731-739.

Beutler, et al. (2000) "Folding and Activity of Circularly Permuted Forms of a Polytopic Membrane Protein" Proc. Natl. Acad. Sci. USA 97(4):1477-1482.

Boder, et al. (1997) "Yeast Surface Display for Screening Combinational Polypeptide Libraries" Nat. Biotechnol. 15(6):553-557.

Boder, et al. (1998) "Optimal Screening of Surface-Displayed Polypeptide Libraries" Biotechnol. Prog. 14(1):55-62.

Boder, et al. (2000) "Directed Evolution of Antibody Fragments with Monovalent Femtomolar Antigen-Binding Affinity" PNAS USA 97(20):10701-10705.

BOS & Tommassen (2004) "Biogenesis of the Gram-negative bacterial outer membrane" Curr Opin Microbiol 7(6):610-616.

Bos, et al. (2004) "Biogenesis of the Gram-Negative Bacterial Outer Membrane" Annu. Rev. Microbiol. 61:191-214.

Boulware, et al. (2006) "Protease specificity determination by using cellular libraries of peptide substrates (CLiPS)" Proc Natl Acad Sci U S A 103(20):7583-7588.

Bupp, et al. (2002) "Altering Retroviral Tropism Using a Random-Display Envelope Library" Mol. Ther. 5(3):329-335.

Camaj, et al., Ligand-mediated protection against phage lysis as a positive selection strategy for the enrichment of epitopes displayed on the surface of E. coli cells, Biol Chem. Dec. 2001;382(12):1669-1677.

Caponigro, et al. (2005) "New Drugs in Cancer Therapy, National Tumor Institute, Naples, Jun. 17-18, 2004" Anticancer Drugs 16(2):211-221.

Charbit, et al. (1986) "Probing the Topology of a Bacterial Membrane Protein by Genetic Insertion of a Foreign Epitope: Expression at the Cell Surface" EMBO J 5(11):3029-3037.

Choo & Klug (1995) "Designing DNA-binding proteins on the surface of filamentous phage" Current Opinion in Biotechnology 6(4):431-436.

Christmann, et al. (1999) "The Cystine Knot of a Squash-Type Protease Inhibitor as a Structural Scaffold for Escherichia coli Cell Surface Display of Conformationally Constrained Peptides" Protein Eng 12(9):797-806.

Ciafré, et al. (2004) "An Anti-VEGF Ribozyme Embedded within the Adenoviral VAI Sequence Inhibits Glioblastoma Cell Angiogenic Potential in Vitro" J. Vasc. Res. 41(3):220-228.

Cunningham, et al. (1979) "Favin versus Concanavalin A: Circularly Permuted Amino Acid Sequences" Proc. Natl. Acad. Sci. U.S.A. 76(7):3218-3222.

Dane, et al. (2006) "Isolation of Cell Specific Peptide Ligands Using Fluorescent Bacterial Display Libraries" J. Immunol. Methods 309(1-2):120-129.

Daugherty, et al. (2000) "Quantitative Analysis of the Effect of the Mutation Frequency on the Affinity Maturation of Single Chain Fv Antibodies" PNAS USA 97(5):2029-2034.

Daugherty, et al., Development of an optimized expression system for the screening of antibody libraries displayed on the Escherichia coli surface., Protein Eng. (1999) 12 (7): 613-621.

Daugherty, et al., Flow cytometric screening of cell-based libraries., Journal of Immunological Methods vol. 243, Issues 1-2, Sep. 21, 2000, pp. 211-227.

Daugherty, et al., Protein engineering with bacterial display, Curr Opin Struct Biol. Aug. 2007;17(4):474-480.

Deperthes, D, Phage display substrate: a blind method for determining protease specificity., Biol Chem. Jul.-Aug. 2002;383(7-8):1107-1112.

Eisenstein, M. (2006) "Sorting Out the Best Targets." Nature Methods, 3(7):498.

EPO Search Report: EP Supplementary Partial EPO Search Report for EP 04816813.2 dated Nov. 2, 2006; EPO Form 1507.2.

EPO Search Report: Supplementary EPO Search Report for EP 04816813.2 dated Jan. 30, 2007; EPO Form 1507.2.

Etz, et al., Bacterial phage receptors, versatile tools for display of polypeptides on the cell surface, Journal of Bacteriology, Dec. 2001, p. 6924-6935, vol. 183, No. 23.

Feldhaus, et al. (2003) "Flow-Cytometric Isolation of Human Antibodies From a Nonimmune Saccharomyces cerevisiae Surface Display Library" Nat. Biotechnol. 21(2):163-170.

Fernandez, et al., Solution NMR studies of the integral membrane proteins OmpX and OmpA from Escherichia coli, FEBS Lett. Aug. 31, 2001;504(3):173-178.

Fields, et al. (1994) "The Two-Hybrid System: An Assay for Protein-Protein Interactions" Trends in Genetics 10(8):286-292.

Francisco, et al. (1992) "Transport and Anchoring of Beta Lactamase to the External Surface of Escherichia coli" PNAS USA 89(7):2713-2717.

Francisco, et al. (1993) "Production and Fluoresence-Activated Cell Sorting of Escherichia coli Expressing a Functional Antibody Fragment Antibody Fragment on the External Surface" Proc. Natl. Acad. Sci. U.S.A. 90(22):10444-10448.

Freudl, Insertion of peptides into cell-surface-exposed areas of the Escherichia coli OmpA protein does not interfere with export and membrane assembly, Gene. Oct. 30, 1989;82(2):229-236.

Gao, et al. (2002) "Down-Regulation of Vascular Endothelial Growth Factor and Up-Regulation of Pigment Epithelium-Derived Factor: A Possible Mechanism for the Anti-Angiogenic Activity of Plasminogen Kringle 5" J. Biol. Chem. 277(11):9492-9497.

Garrett, et al. (2003) "Effect of Linker Sequence on the Stability of Circularly Permuted Variants of Ribonuclease T1" Bioorg. Chem. 31(5):412-424.

Georgiou (2000) "Analysis of Large Libraries of Protein Mutants Using Flow Cytometry" Adv. Protein Chem. 55:293-315.

Georgiou, et al. (1997) "Display of Heterologous Proteins on the Surface of Microorganisms: From the Screening of Combinatorial Libraries to Live Recombinant Vaccines" Nat. Biotechnol. 15(1):29-34.

Giebel, et al. (1995) "Screening of Cyclic Peptide Phage Libraries Identifies Ligands That Bind Streptavidin with High Affinities" Biochemistry 34(47):15430-15435.

Goldenberg & Creighton (1983) "Circular and Circularly Permuted Forms of Bovine Pancreatic Trypsin Inhibitor" J. Mol. Biol. 165(2):407-413.

(56) References Cited

OTHER PUBLICATIONS

Graf & Schachman "Random circular permutation of genes and expressed polypeptide chains: application of the method to the catalytic chains of aspartate transcarbamoylase" Proc Natl Acad Sci U S A. Oct. 15, 1996;93(21):11591-11596.

Hanes, et al. (1997) "In Vitro Selection and Evolution of Functional Proteins by Using Ribosome Display" PNAS USA 94(10):4937-4942.

Heinemann, et al. (1995) "Circular Permutation of Polypeptide Chains. Implications for Protein Folding and Stability" Prog Biophys Mol Biol. 64:121-143.

Hoogenboom, H.R., Designing and optimizing library selection strategies for generating high-affinity antibodies., Trends in Biotechnology, vol. 15, Issue 2, Feb. 1997, pp. 62-70.

James, et al. (2003) "Antibody Multispecificity Media Ted by Conformational Diversity" Science 299:1362-1367.

Jung, et al. (1998) "Surface Display of Zymomonas Mobilis Levansucrase by Using the Ice-nucleation Protein of Pseudomonas Syringae" Nat Biotechnol. 16(6):576-580.

Kim, et al. (2000) "Isolation of Peptide Ligands That Inhibit Glutamate Racemase Activity from a Random Phage Display Library" J Biomol. Screen. 5(6):435-440.

Kjaergaard, et al. (2001) "Novel Zn(2+)-Chelating Peptides Selected from a Fimbria-Displayed Random Peptide Library" Appl Environ Microbiol. 67(12):5467-5473.

Kodadek (2001) "Protein Microarrays: Prospects and Problems" Chem. Biol. 8(2):105-115.

Koebnik, et al., Structural and functional roles of the surface-exposed loops of the beta-barrel membrane protein OmpA from Escherichia coli, Journal of Bacteriology, Jun. 1999, p. 3688-3694, vol. 181, No. 12.

Koebnik, et al., Structure and function of bacterial outer membrane proteins:barrels in a nutshell, Molecular Microbiology, (2000), 37(2), 239-253.

Koebnik, et. al., Membrane assembly of circularly permuted variants of the E. coli outer membrane protein OmpA, J Mol Biol. Jul. 28, 1995;250(5):617-626.

Koebnik, Membrane assembly of the Escherichia coli outer membrane protein OmpA: exploring sequence constraints on transmembrane beta-strands, J Mol Biol. Jan. 29, 1999;285(4):1801-1810.

Konner & Dupont (2004) "Use of Soluble Recombinant Decoy Receptor Vascular Endothelial Growth Factor Trap (VEGF Trap) to Inhibit Vascular Endothelial Growth Factor Activity" Clin. Colorectal. Cancer 4 Suppl. 2:S81-S85.

Ladner, R., Constrained peptides as binding entities,Trends in Biotechnology, vol. 13, Issue 10, Oct. 1995, pp. 426-430.

Lee, et al. (2003) "Microbial Cell-Surface Display" Trends in Biotechnology, 21(1):46-52.

Ley., et al., Obtaining a family of high-affinity, high-specificity protein inhibitors of plasmin and plasma kallikrein., Molecular Diversity, vol. 2, Nos. 1-2, 119-124, Oct. 1996.

Lowman., et al., Selecting high-affinity binding proteins by monovalent phage display., Biochemistry. Nov. 12, 1991;30(45):10832-10838.

Lu, et al. (1995) "Expression of Thioredoxin Random Peptide Libraries on the Escherichia coli Cell Surface as Functional Fusions to Flagellin: A System Designed for Exploring Protein-Protein Interactions" Biotechnology 13(4):366-372.

Macintyre, et al., The signal sequence of an Escherichia coli outer membrane protein can mediate translocation of a not normally secreted protein across the plasma membrane, J. Biol. Chem., vol. 262, Issue 17, 8416-8422, 06, 1987.

Markland, et al., Affinity maturation of proteins displayed on surface of MI3 bacteriophage as major coat protein fusions., Methods in Enzymology, vol. 267, 1996, pp. 68-82.

Markland, et al., Iterative Optimization of High-Affinity Protease Inhibitors Using Phage Display. 2. Plasma Kallikrein and Thrombin., Biochemistry, 1996, 35 (24), pp. 8058-8067.

Markland, et al., Iterative Optimization of High-Affinity Protease Inhibitors Using Phage Display. 1. Plasmin., Biochemistry, 1996, 35 (24), pp. 8045-8057.

Markland, et al., Selection for protease inhibitors using bacteriophage display., Methods in Enzymology vol. 267, 1996, pp. 28-51.

Matthews & Wells (1993) "Substrate phage: selection of protease substrates by monovalent phage display" Science 260(5111):1113-1117.

Maurer, et al. (1997) "Autodisplay: One-Component System for Efficient Surface Display and Release of Soluble Recombinant Proteins from Escherichia coli" J Bacteriol. 179(3):794-804.

Mejare, et al., (1998) Selection of cadmium specific hexapeptides and their expression as OmpA fusion proteins in Escherichia coli, Protein Engineering, vol. 11, 489-494.

Morimoto, et al. (2004) "Gene Expression Profiling of Human Colon Xenograft Tumors Following Treatment with SU11248, a Multitargeted Tyrosine Kinase Inhibitor" Oncogene 23(8):1618-1626.

Müller, et al. (2003) "Random Peptide Libraries Displayed on Adeno-Associated Virus to Select for Targeted Gene Therapy Vectors" Nat Biotechnol. 21(9):1040-1046.

Nakajima, et al. (2000) "Expression of Random Peptide Fused to Invasin on Bacterial Cell Surface for Selection of Cell Targeting Peptides" Gene 260(1-2):121-131.

Nguyen, et al. (2005) "Evolutionary Optimization of Fluorescent Proteins for Intracellular FRET" Nat Biotechnol. 23(3):355-360.

Olsen, et al. (2003) "High-Throughput Facs Method for Directed Evolution of Substrate Specificity" Methods Mol. Biol. 230:329-342.

Pasqualini & Ruoslahti (1996) "Organ Targeting In Vivo Using Phage Display Peptide Libraries" Nature 380(67572):364-366.

Pautsch & Schulz (2000) "High-Resolution Structure of the OmpA Membrane Domain" J. Mol. Biol. 298(2):273-282.

Poul, et al. (2000) "Selection of Tumor Specific Internalizing Human Antibodies from Phage Libraries" J Mol Biol. 301(5):1149-1161.

Proba, et al. (1998) "Antibody scFv Fragments without Disulfide Bonds Made by Molecular Evolution" J. Mol. Biol. 275(2):245-253.

Rice, et al., Bacterial display using circularly permuted outer membrane protein OmpX yields high affinity peptide ligands, Protein Sci. Apr. 2006; 15(4): 825-836.

Rice, et al., Directed evolution of a biterminal bacterial display scaffold enhances the display of diverse peptides, Protein Eng Des Sel. Jul. 2008;21(7):435-442.

Riedel, et al. (2005) "Antiangiogenic Therapy of Head and Neck Squamous Cell Carcinoma by Vascular Endothelial Growth Factor Antisense Therapy" Adv. Otorhinolaryngol. 62:103-120.

Roberts, et al. (1996) "Affinity Maturation of Proteins Displayed on Surface of M13 Bacteriophage as Major Coat Protein Fusions" Methods Enzymol., 267:68-82.

Shusta, et al. (1999) "Biosynthetic Polypeptide Libraries" Curr Opin Biotechnol. 10(2):117-122.

Smith (1985) "Filamentous Fusion Phage: Novel Expression Vectors That Display Cloned Antigens on the Virion Surface" Science 228(4705):1315-1317.

Ståhl & Uhlén (1997) "Bacterial Surface Display: Trends and Progress" Trends Biotechnol. 15(5):185-192.

Susman (2005) "Bevacizumab Adds Survival Benefit in Colorectal Cancer" Lancet Oncol. 6:136.

Takahara, et al., The ompA signal peptide directed secretion of Staphylococcal nuclease A by Escherichia coli,J. Biol. Chem., vol. 260, Issue 5, 2670-2674, 03, 1985.

Taschner, et al. (2002) "Selection of Peptide Entry Motifs by Bacterial Surface Display" Biochem. J., 367:393-402.

Tuccillo, et al. (2005) "Antitumor Activity of ZD6474, a Vascular Endothelial Growth Factor-2 and Epidermal Growth Factor Receptor Small Molecule Tyrosine Kinase Inhibitor, in Combination with SC-236, A Cyclooxygenase-2 Inhibitor" Clin. Cancer Res. 11(3):1268-1276.

Vogt, et al., The structure of the outer membrane protein OmpX from Escherichia coli reveals possible mechanisms of virulence, Structure (London), vol. 7, Issue 10, Oct. 15, 1999, pp. 1301-1309.

(56) References Cited

OTHER PUBLICATIONS

Wang, et al., Phage display of proteases and macromolecular inhibitors., Methods in Enzymology vol. 267, 1996, pp. 52-68.
Wentzel, et al. (2001) "Display of Passenger Proteins on the Surface of *Escherichia coli* K-12 by the Enterohemorrhagic *E. coli* Intimin EaeA" *J. Bacteriol.* 183(24):7272-7284.
Whaley, et al. (2000) "Selection of Peptides with Semiconductor Binding Specificity for Directed Nanocrystal Assembly" *Nature* 405(6787):665-668.
Wild, et al. (2000) "Inhibition of Angiogenesis and Tumor Growth by VEGF121 Toxin Conjugate: Differential Effect on Proliferating Endothelial Cells" *Br. J. Cancer* 83(8):1077-1083.
Wilson, et al. (2001) "The Use of mRNA Display to Select High-Affinity Protein-Binding Peptides" *PNAS USA* 98(7):3750-3755.
Wittrup (2001) "Protein Engineering by Cell-Surface Display" *Curr. Opin. Biotechnol.* 12(4):395-399.
Yang, et al. (1995) "CDR Walking Mutagenesis for the Affinity Maturation of a Potent Human Anti-HIV-1 Antibody into the Picomolar Range" *J Mol. Biol.* 254(3):392-403.
Yonezawa, et al. (2003) "DNA Display for In Vitro Selection of Diverse Peptide Libraries" *Nucleic Acids Research* 31:e118.
Yu & Lutz (2011) "Circular Permutation: A Different Way to Engineer Enzyme Structure and Function" Trends Biotechnol. 29(1):18-25.

$K_D = 2$ nM ⟶
```
TTCKYYLSCRWRKDL
YPPRFQYYRFYYRGP
TDFLSYYRVYRTPLQ
TFMPSYYRSWGPPPT
```
} Group 1

```
RYIMNHRGFYIFVPR
 LMNWRGFMVPRESPK
  PYLNARGFSVTREQI
  MIFNSRGFLSLMSSG
WTKLKNSRGFELQLD
 EWACNDRGFNCQLQR
 FPIYNQRGFITLASP
```
} Group 2

| Clone | # | Sequence | % Fluor | Brightness |
|---|---|---|---|---|
| 1A.1 | (1) | IC_NIKK__WACE_R | 12 | 6 |
| 1A.2 | (1) | N_VRLMT_L_CT_D | 55 | 48 |
| 1A.3 | (3) | GC__LPT_S_CFGR | 29 | 21 |
| 2B.1 | (1) | VCRLMRG_CL___F | 15 | 11 |
| 2B.2 | (2) | _CVLHRQ_CL___R | 91 | 119 |
| 4C.1 | (1) | --KQRGAT__LRT_TLR | 28 | 19 |
| 4C.2 | (1) | --YER_PT_VLRT_RPW | 73 | 42 |
| Gent1 | (15) | YCLS_SNG__FHCPA--- | 25 | 11 |
| Gent2 | (1) | RVWW_M_G__R__Q--- | | |
| Gent3 | (1) | -----E__FRL_A_PQSLVS | | |

Figure 20

YCCHPQVCFLGHRAACP
WCCHPQVCSLSLAYKCQ
ICCHPQVCAWNRVFLCK
ICCHPQVCSGLNRFRCG
WCCHPQVCHRAMVRNCI
ACCHPQVCVMALPYHCL
LCCHPQVCASAGYYACY
LCCHPQNCVSFRHVECR
ICCHPQWCGLTVWWPCK

QSLVCQNVCWMRE
CMIICQNVCYRKC
KALVCQNVCYTMS
SKWICQNVCYPGL
GTLVCMNFCYLSK
PTLICMNVCFYDQ
SHWFCVNVCFRIQ
TYSWCANVCMHYS
TRLICANLCWYAE

QAGLTWYWWYSCRQI
MNYWIYFCGVWMQAH
SYWVYHCYYGWYSQW  Group 1
CWYQWCGYYYSYNCH
QTATVSYWCYWWWKV
HPKSPYRYWDWTAHRYYSYQLCNLSS MVWTKWSWCAFYRRI
QEWRQLTRWCWVQIK  Group 2
PWCWMWTKGRWYYVA
TWTWCWRNYIWQLST
WVAGYWWCWSVMYRS

GDTWVWYCWYWTRS wt OmpX T7tag
19 AA
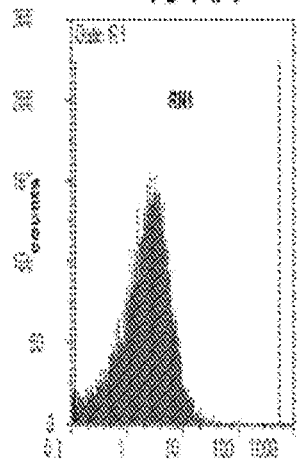
Mean FL3 = 3.4
19 AA + Tfl
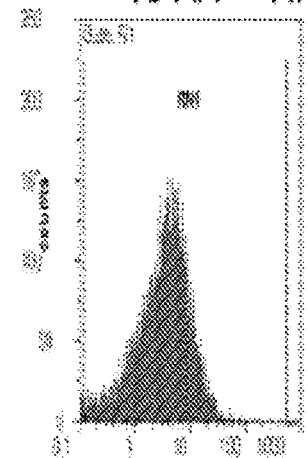
Mean FL3 = 5.6
20 AA
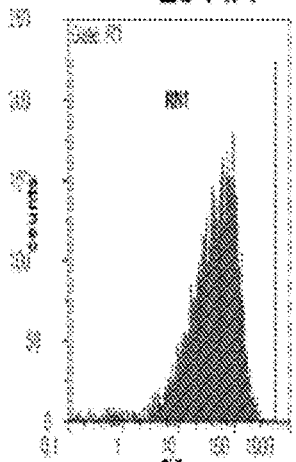
Mean FL3 = 58.6
Leu- OmpX T7tag
19 AA
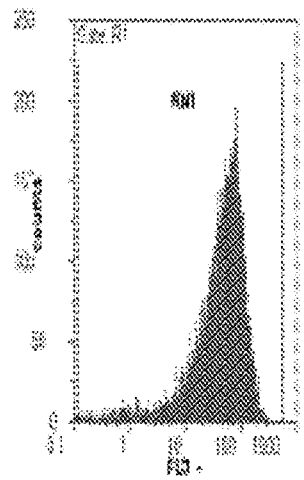
Mean FL3 = 59.0
19 AA + Tfl
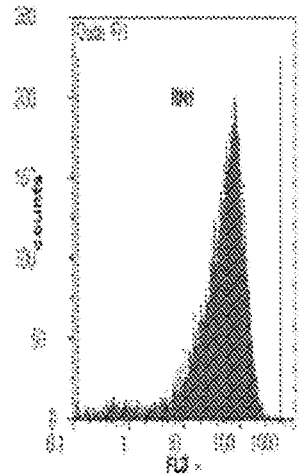
Mean FL3 = 63.7
20 AA
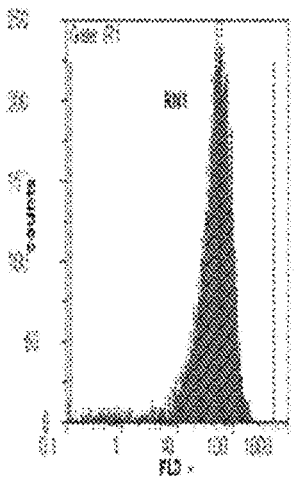
Mean FL3 = 56.3
Figure 34

```
                           SEQUENCE LISTING

<160> NUMBER OF SEQ ID NOS: 321

<210> SEQ ID NO 1
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 1

Glu Trp Ala Cys Asn Asp Arg Gly Phe Asn Cys Gln Leu Gln Arg
1               5                   10                  15

<210> SEQ ID NO 2
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (5)..(5)
<223> OTHER INFORMATION: Xaa = Any Naturally Occurring Amino Acid

<400> SEQUENCE: 2

Leu Ile Gly Gln Xaa Asn Asn Gly Pro Thr
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 3

Met Ala Ser Met Thr Gly Gly Gln Gln Met Gly
```

<210> SEQ ID NO 4
<211> LENGTH: 29
<212> TYPE: PRT
<213> ORGANISM: Escherichia coli

<400> SEQUENCE: 4

Ala Lys Leu Gly Trp Ser Gln Tyr His Asp Thr Gly Phe Ile Asn Asn
1               5                   10                  15

Asn Gly Pro Thr His Glu Asn Gln Leu Gly Ala Gly Ala
            20                  25

<210> SEQ ID NO 5
<211> LENGTH: 29
<212> TYPE: PRT
<213> ORGANISM: Escherichia coli

<400> SEQUENCE: 5

Ala Lys Leu Gly Trp Ser Gln Tyr His Asp Thr Gly Leu Ile Asn Asn
1               5                   10                  15

Asn Gly Pro Thr His Glu Asn Gln Leu Gly Ala Gly Ala
            20                  25

<210> SEQ ID NO 6
<211> LENGTH: 29
<212> TYPE: PRT
<213> ORGANISM: Shigella sonnei

<400> SEQUENCE: 6

Ala Lys Leu Gly Trp Ser Gln Tyr His Asp Thr Gly Phe Ile Asn Asn
1               5                   10                  15

Asn Gly Pro Thr His Glu Asn Gln Leu Gly Ala Gly Ala
            20                  25

<210> SEQ ID NO 7
<211> LENGTH: 29
<212> TYPE: PRT
<213> ORGANISM: Shigella dysenteriae

<400> SEQUENCE: 7

Ala Lys Leu Gly Trp Ser Gln Tyr His Asp Thr Gly Phe Ile Asp Asn
1               5                   10                  15

Asn Gly Pro Thr His Glu Asn Gln Leu Gly Ala Gly Ala
            20                  25

<210> SEQ ID NO 8
<211> LENGTH: 29
<212> TYPE: PRT
<213> ORGANISM: Shigella flexneri

<400> SEQUENCE: 8

Ala Lys Leu Gly Trp Ser Gln Tyr His Asp Thr Gly Phe Ile Pro Asn
1               5                   10                  15

Asn Gly Pro Thr His Glu Asn Gln Leu Gly Ala Gly Ala
            20                  25

<210> SEQ ID NO 9
<211> LENGTH: 29
<212> TYPE: PRT
<213> ORGANISM: Salmonella typhimurium

<400> SEQUENCE: 9

Ala Lys Leu Gly Trp Ser Gln Tyr His Asp Thr Gly Phe Ile His Asn
1               5                   10                  15

Asp Gly Pro Thr His Glu Asn Gln Leu Gly Ala Gly Ala
            20                  25

<210> SEQ ID NO 10
<211> LENGTH: 29
<212> TYPE: PRT
<213> ORGANISM: Salmonella enterica

<400> SEQUENCE: 10

Ala Lys Leu Gly Trp Ser Gln Tyr His Asp Thr Gly Phe Ile His Asn
1               5                   10                  15

Asp Gly Pro Thr His Glu Asn Gln Leu Gly Ala Gly Ala
            20                  25

<210> SEQ ID NO 11
<211> LENGTH: 33
<212> TYPE: PRT
<213> ORGANISM: Enterobacter aerogenes

<400> SEQUENCE: 11

Ala Lys Leu Gly Trp Ser Gln Phe His Asp Thr Gly Trp Tyr Asn Ser
1               5                   10                  15

Asn Leu Asn Asn Asn Gly Pro Thr His Glu Ser Gln Leu Gly Ala Gly
            20                  25                  30

Ala

<210> SEQ ID NO 12
<211> LENGTH: 30
<212> TYPE: PRT
<213> ORGANISM: Yersinia pestis

<400> SEQUENCE: 12

Ala Lys Leu Gly Trp Ser Gln Tyr Gln Asp Thr Gly Ser Ile Ile Asn
1               5                   10                  15

Asn Asp Gly Pro Thr His Lys Asp Gln Leu Gly Ala Gly Ala
            20                  25                  30

<210> SEQ ID NO 13
<211> LENGTH: 34
<212> TYPE: PRT
<213> ORGANISM: Klebsiella pneumoniae

<400> SEQUENCE: 13

Ala Lys Leu Gly Trp Ser Gln Tyr His Asp Thr Gly Phe Tyr Gly Asn
1               5                   10                  15

Gly Phe Gln Asn Asn Asn Gly Pro Thr Arg Asn Asp Gln Leu Gly Ala
            20                  25                  30

Gly Ala

<210> SEQ ID NO 14
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 14

Ala Ser Asn Ala Ser Asn Ala Ser Asn
1               5

```
<210> SEQ ID NO 15
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (5)..(9)
<223> OTHER INFORMATION: Xaa = Any Amino Acid

<400> SEQUENCE: 15

Gly Gly Cys Cys Xaa Xaa Xaa Xaa Xaa Gly Gly Cys Cys
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 16

Glu Trp Ala Cys Asn Asp Arg Gly Phe Asn Cys Gln Leu Gln Arg
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 17

Phe Pro Ile Tyr Asn Gln Arg Gly Phe Ile Thr Leu Ala Ser Pro
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 18

His Met Arg Trp Asn Thr Arg Gly Phe Leu Tyr Pro Ala Met Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 19

Arg Tyr Ile Met Asn His Arg Gly Phe Tyr Ile Phe Val Pro Arg
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 20
```

Val Arg Thr Trp Asn Asp Arg Gly Phe Gln Gln Ser Val Asp Arg
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 21

Met Ile Phe Asn Ser Arg Gly Phe Leu Ser Leu Met Ser Ser Gly
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 22

Leu Met Asn Trp Arg Gly Phe Met Val Pro Arg Glu Ser Pro Lys
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 23

Trp Thr Lys Leu Lys Asn Ser Arg Gly Phe Glu Leu Gln Leu Asp
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 24

Pro Tyr Leu Asn Ala Arg Gly Phe Ser Val Thr Arg Glu Gln Ile
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (2)..(4)
<223> OTHER INFORMATION: Xaa = Any Naturally Occurring Amino Acid

<400> SEQUENCE: 25

Ile Xaa Asn Xaa Arg Gly Phe
1               5

<210> SEQ ID NO 26
<211> LENGTH: 15
<212> TYPE: PRT
<213> ORGANISM: Artificial Sequence
<220> FEATURE:

<223> OTHER INFORMATION: Synthetic Peptide

<400> SEQUENCE: 26

Tyr Pro Pro Arg Phe Gln Tyr Tyr Arg Phe Tyr Tyr Arg Gly Pro
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 27

Thr Asp Phe Leu Ser Tyr Tyr Arg Val Tyr Arg Thr Pro Leu Gln
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 28

Thr Phe Met Pro Ser Tyr Tyr Arg Ser Trp Gly Pro Pro Pro Thr
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 29

Thr Thr Cys Lys Tyr Tyr Leu Ser Cys Arg Trp Arg Lys Asp Leu
1               5                   10                  15

<210> SEQ ID NO 30
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 30

Ser Tyr Tyr Arg Ser Tyr
1               5

<210> SEQ ID NO 31
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 31

Arg Leu Glu Ile Cys Gln Asn Val Cys Tyr Tyr Leu Gly Thr Leu
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 32

Ile Cys Ser Tyr Val Met Tyr Thr Thr Cys Phe Leu Arg Val Tyr
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 33

Thr Val Leu Ile Cys Met Asn Ile Cys Trp Thr Gly Glu Thr Gln
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 34

Val Thr Ser Leu Cys Met Asn Val Cys Tyr Ser Leu Thr Thr Tyr
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 35

Tyr Trp Val Cys Met Asn Val Cys Met Tyr Tyr Thr Ala Arg Gln
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 36

Leu Pro Val Trp Cys Val Met His Val Cys Leu Thr Ser Ser Arg
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 37

Asn Glu Trp Tyr Cys Gln Asn Val Cys Glu Arg Met Pro His Ser
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic Peptide

```
<400> SEQUENCE: 38

Ile Met Met Glu Cys Phe Tyr Val Cys Thr Ile Ala Asn Thr Gln
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 39

Thr Trp Val Gln Cys Thr Met Val Cys Tyr Gly Met Ser Thr Thr
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 40

Ser Ile Thr Ile Cys Trp Tyr Thr Cys Met Val Gln Lys Thr Ala
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 41

Ala Asp Thr Ile Cys Trp Tyr Val Cys Thr Ile Ser Val His Ala
1               5                   10                  15

<210> SEQ ID NO 42
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 42

Ile Cys Met Asn Val Cys
1               5

<210> SEQ ID NO 43
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 43

Asn Pro Phe Cys Ser Trp Tyr Arg Trp Arg Asn Trp Cys Thr Lys
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 44
```

```
Arg His Leu Tyr Cys Trp Thr Trp Arg Trp Cys His Phe Lys Asp
1               5                  10                  15

<210> SEQ ID NO 45
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (2)..(2)
<223> OTHER INFORMATION: The amino acid at this position can be present
      or absent, Xaa = Any Amino Acid
<220> FEATURE:
<221> NAME/KEY: VARIANT
<222> LOCATION: (4)..(5)
<223> OTHER INFORMATION: The amino acids at these positions can be
      present or absent, Xaa = Any Amino Acid
<220> FEATURE:
<221> NAME/KEY: VARIANT
<222> LOCATION: (8)..(8)
<223> OTHER INFORMATION: The amino acid at this position can be present
      or absent, Xaa = Any Amino Acid

<400> SEQUENCE: 45

Cys Xaa Trp Xaa Xaa Trp Arg Xaa Trp
1               5

<210> SEQ ID NO 46
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 46

Ser Tyr Ile Ser Thr Trp Leu Asn Phe Leu Phe Cys Gly Gln Ser
1               5                  10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 47

Asn Asn Tyr Ser Ala Trp Leu Arg Cys Leu Leu Arg Ala Tyr Ser
1               5                  10                  15

<210> SEQ ID NO 48
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (2)..(2)
<223> OTHER INFORMATION: The amino acid at this position can be present
      or absent, Xaa = Any Amino Acid
<220> FEATURE:
<221> NAME/KEY: VARIANT
<222> LOCATION: (5)..(6)
<223> OTHER INFORMATION: The amino acids at these positions can be
      present or absent, Xaa = Any Amino Acid
<220> FEATURE:
<221> NAME/KEY: VARIANT
<222> LOCATION: (8)..(11)
<223> OTHER INFORMATION: The amino acids at these positions can be
```

```
                present or absent, Xaa = Any Amino Acid

<400> SEQUENCE: 48

Ser Xaa Trp Leu Xaa Xaa Leu Xaa Xaa Xaa Xaa Ser
1               5                   10

<210> SEQ ID NO 49
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 49

Gly Asp Thr Trp Val Trp Tyr Cys Trp Tyr Trp Thr Arg Ser Ile
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 50

Trp Val Cys Thr Trp Asn Tyr Trp Thr Arg Val Thr Trp Cys Leu
1               5                   10                  15

<210> SEQ ID NO 51
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (3)..(6)
<223> OTHER INFORMATION: The amino acids at theses positions can be
        present or absent, Xaa = Any Amino Acid

<400> SEQUENCE: 51

Trp Val Xaa Xaa Xaa Xaa Tyr Trp Thr Arg
1               5                   10

<210> SEQ ID NO 52
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 52

Pro Trp Cys Trp Met Trp Thr Lys Gly Arg Trp Tyr Tyr Val Ala
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 53

Gln Ile Gln Trp Cys Trp Val Asn His Arg Trp Ser Pro Val Val
1               5                   10                  15

<210> SEQ ID NO 54
```

```
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 54

Trp Val Ala Gly Tyr Trp Trp Cys Trp Ser Val Met Tyr Arg Ser
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 55

Thr Trp Thr Trp Cys Trp Arg Asn Tyr Ile Trp Gln Leu Ser Thr
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 56

Gln Glu Trp Arg Gln Leu Thr Arg Trp Cys Trp Val Gln Ile Lys
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 57

Gln Thr Ala Thr Val Ser Tyr Trp Cys Tyr Trp Trp Trp Lys Val
1               5                   10                  15

<210> SEQ ID NO 58
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (4)..(6)
<223> OTHER INFORMATION: The amino acids at theses positions can be
      present or absent, Xaa = Any Amino Acid

<400> SEQUENCE: 58

Trp Cys Trp Xaa Xaa Xaa Lys
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 59

Ser Met Gly Pro Gln Gln Met
```

```
<210> SEQ ID NO 60
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 60

Cys Asn Asp Arg Gly Phe Asn Cys
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 61

Cys Gln Asn Val Cys
1               5

<210> SEQ ID NO 62
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (8)..(8)
<223> OTHER INFORMATION: Xaa = Any Naturally Occurring Amino Acid

<400> SEQUENCE: 62

Ser Met Gly Pro Gln Gln Met Xaa Ala Trp
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 63

Ser Met Gly Pro Gln Gln Met Ala Trp
1               5

<210> SEQ ID NO 64
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (2)..(2)
<223> OTHER INFORMATION: The amino acid at this position can be present
      or absent, Xaa = Any Amino Acid
<220> FEATURE:
<221> NAME/KEY: VARIANT
<222> LOCATION: (4)..(4)
<223> OTHER INFORMATION: The amino acid at this position can be present
      or absent, Xaa = Any Amino Acid
<220> FEATURE:
<221> NAME/KEY: VARIANT
<222> LOCATION: (8)..(10)
<223> OTHER INFORMATION: The amino acids at theses positions can be
``` present or absent, Xaa = Any Amino Acid

<400> SEQUENCE: 64

Ile Xaa Asn Xaa Arg Gly Phe Xaa Xaa Xaa Val
1               5                   10

<210> SEQ ID NO 65
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 65

Ser Ala Glu Cys His Pro Gln Gly Pro Pro Cys Ile Glu Gly Arg
1               5                   10                  15

<210> SEQ ID NO 66
<211> LENGTH: 16
<212> TYPE: PRT
<213> ORGANISM: Escherichia coli

<400> SEQUENCE: 66

Glu Lys Ser Arg Thr Ala Ser Ser Gly Asp Tyr Asn Lys Asn Gln Tyr
1               5                   10                  15

<210> SEQ ID NO 67
<211> LENGTH: 16
<212> TYPE: PRT
<213> ORGANISM: Shigella flexneri

<400> SEQUENCE: 67

Glu Lys Ser Arg Thr Ala Ser Ser Gly Asp Tyr Asn Lys Asn Gln Tyr
1               5                   10                  15

<210> SEQ ID NO 68
<211> LENGTH: 16
<212> TYPE: PRT
<213> ORGANISM: Salmonella enterica

<400> SEQUENCE: 68

Glu Lys Asp Arg Thr Asn Gly Ala Gly Asp Tyr Asn Lys Gly Gln Tyr
1               5                   10                  15

<210> SEQ ID NO 69
<211> LENGTH: 15
<212> TYPE: PRT
<213> ORGANISM: Klebsiella pneumoniae

<400> SEQUENCE: 69

Glu Lys Asp Asn Asn Ser Asn Gly Thr Tyr Asn Lys Gly Gln Tyr
1               5                   10                  15

<210> SEQ ID NO 70
<211> LENGTH: 15
<212> TYPE: PRT
<213> ORGANISM: Serratia marcescens

<400> SEQUENCE: 70

Glu Lys Asp Gly Ser Gln Asp Gly Phe Tyr Asn Lys Ala Gln Tyr
1               5                   10                  15

<210> SEQ ID NO 71
<211> LENGTH: 16
<212> TYPE: PRT

<213> ORGANISM: Yersinia pestis

<400> SEQUENCE: 71

Glu Lys Ser Gly Phe Gly Asp Glu Ala Val Tyr Asn Lys Ala Gln Tyr
1 5 10 15

<210> SEQ ID NO 72
<211> LENGTH: 16
<212> TYPE: PRT
<213> ORGANISM: Escherichia coli

<400> SEQUENCE: 72

Lys Phe Gln Thr Thr Glu Tyr Pro Thr Tyr Lys Asn Asp Thr Ser Asp
1 5 10 15

<210> SEQ ID NO 73
<211> LENGTH: 16
<212> TYPE: PRT
<213> ORGANISM: Shigella flexneri

<400> SEQUENCE: 73

Lys Phe Gln Thr Thr Glu Tyr Pro Thr Tyr Lys Asn Asp Thr Ser Asp
1 5 10 15

<210> SEQ ID NO 74
<211> LENGTH: 16
<212> TYPE: PRT
<213> ORGANISM: Salmonella enterica

<400> SEQUENCE: 74

Lys Phe Gln Thr Thr Asp Tyr Pro Thr Tyr Lys His Asp Thr Ser Asp
1 5 10 15

<210> SEQ ID NO 75
<211> LENGTH: 15
<212> TYPE: PRT
<213> ORGANISM: Klebsiella pneumoniae

<400> SEQUENCE: 75

Lys Phe Gln Asn Asn Asn Tyr Pro His Lys Ser Asp Met Ser Asp
1 5 10 15

<210> SEQ ID NO 76
<211> LENGTH: 17
<212> TYPE: PRT
<213> ORGANISM: Serratia marcescens

<400> SEQUENCE: 76

Lys Phe Thr Thr Asn Ala Gln Asn Gly Thr Ser Arg His Asp Thr Ala
1 5 10 15

Asp

<210> SEQ ID NO 77
<211> LENGTH: 18
<212> TYPE: PRT
<213> ORGANISM: Yersinia pestis

<400> SEQUENCE: 77

Arg Phe Thr Gln Asn Glu Ser Ala Phe Val Gly Asp Lys His Ser Thr
1 5 10 15

Ser Asp

<210> SEQ ID NO 78

```
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 78

Gly Leu Tyr Gly Leu Tyr Ser Glu Arg Gly Leu Tyr Gly Leu Tyr
 1               5                  10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 79

Gly Leu Tyr Ser Glu Arg Gly Leu Tyr Gly Leu Tyr Ser Glu Arg
 1               5                  10                  15

<210> SEQ ID NO 80
<211> LENGTH: 45
<212> TYPE: DNA
<213> ORGANISM: Artificial Sequence
<220> FEATURE:
<223> OTHER INFORMATION: Synthetic Primer

<400> SEQUENCE: 80
gagtccagag gtaccaacga ggcgcaaaaa atgaaaaaga cagct          45

<210> SEQ ID NO 81
<211> LENGTH: 35
<212> TYPE: DNA
<213> ORGANISM: Artificial Sequence
<220> FEATURE:
<223> OTHER INFORMATION: Synthetic Primer

<400> SEQUENCE: 81
cgttatgtca agcttttaag cctgcggctg agtta                35

<210> SEQ ID NO 82
<211> LENGTH: 45
<212> TYPE: DNA
<213> ORGANISM: Artificial Sequence
<220> FEATURE:
<223> OTHER INFORMATION: Synthetic Primer

<400> SEQUENCE: 82
cagtaccatg acactggcct catcggccaa aatggtccga cccat          45

<210> SEQ ID NO 83
<211> LENGTH: 45
<212> TYPE: DNA
<213> ORGANISM: Artificial Sequence
<220> FEATURE:
<223> OTHER INFORMATION: Synthetic Primer

<400> SEQUENCE: 83
aacatcggtg acgcaggcca gatcggccag cgtccggaca acggc          45

<210> SEQ ID NO 84
<211> LENGTH: 96
<212> TYPE: DNA
<213> ORGANISM: Artificial Sequence
<220> FEATURE:
<223> OTHER INFORMATION: Synthetic Primer
```

<400> SEQUENCE: 84
cgtcctggcc tcatcggcca aggatccatg gcctccatga ccggaggaca acaaatggga    60
tccggaaatg gtccgaccca tgaaaaccaa ctgggc                              96

<210> SEQ ID NO 85
<211> LENGTH: 96
<212> TYPE: DNA
<213> ORGANISM: Artificial Sequence
<220> FEATURE:
<223> OTHER INFORMATION: Synthetic Primer

<400> SEQUENCE: 85
cgtcatctgg ccgatctggc ctccggatcc catttgttgt cctccggtca tggaggccat    60
ggatcctgcg tcaccgatgt tgttggtcca ctggta                              96

<210> SEQ ID NO 86
<211> LENGTH: 54
<212> TYPE: DNA
<213> ORGANISM: Artificial Sequence
<220> FEATURE:
<223> OTHER INFORMATION: Synthetic Primer

<400> SEQUENCE: 86
catccgcagg gcccgccgtg cattgaaggc cgcaatggtc cgacccatga aaac          54

<210> SEQ ID NO 87
<211> LENGTH: 53
<212> TYPE: DNA
<213> ORGANISM: Artificial Sequence
<220> FEATURE:
<223> OTHER INFORMATION: Synthetic Primer

<400> SEQUENCE: 87
gcacggcggg ccctgcggat ggcattccgc gctttggccg atgaggccag tgt           53

<210> SEQ ID NO 88
<211> LENGTH: 96
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (22)..(23)
<223> OTHER INFORMATION: n = A,T,C or G
<220> FEATURE:
<221> NAME/KEY: misc_feature
<222> LOCATION: (25)..(26)
<223> OTHER INFORMATION: n = A,T,C or G
<220> FEATURE:
<221> NAME/KEY: misc_feature
<222> LOCATION: (28)..(29)
<223> OTHER INFORMATION: n = A,T,C or G
<220> FEATURE:
<221> NAME/KEY: misc_feature
<222> LOCATION: (31)..(32)
<223> OTHER INFORMATION: n = A,T,C or G
<220> FEATURE:
<221> NAME/KEY: misc_feature
<222> LOCATION: (34)..(35)
<223> OTHER INFORMATION: n = A,T,C or G
<220> FEATURE:
<221> NAME/KEY: misc_feature
<222> LOCATION: (37)..(38)
<223> OTHER INFORMATION: n = A,T,C or G
<220> FEATURE:
<221> NAME/KEY: misc_feature
<222> LOCATION: (40)..(41)

```
<223> OTHER INFORMATION: n = A,T,C or G
<220> FEATURE:
<221> NAME/KEY: misc_feature
<222> LOCATION: (43)..(44)
<223> OTHER INFORMATION: n = A,T,C or G
<220> FEATURE:
<221> NAME/KEY: misc_feature
<222> LOCATION: (46)..(47)
<223> OTHER INFORMATION: n = A,T,C or G
<220> FEATURE:
<221> NAME/KEY: misc_feature
<222> LOCATION: (49)..(50)
<223> OTHER INFORMATION: n = A,T,C or G
<220> FEATURE:
<221> NAME/KEY: misc_feature
<222> LOCATION: (52)..(53)
<223> OTHER INFORMATION: n = A,T,C or G
<220> FEATURE:
<221> NAME/KEY: misc_feature
<222> LOCATION: (55)..(56)
<223> OTHER INFORMATION: n = A,T,C or G
<220> FEATURE:
<221> NAME/KEY: misc_feature
<222> LOCATION: (58)..(59)
<223> OTHER INFORMATION: n = A,T,C or G
<220> FEATURE:
<221> NAME/KEY: misc_feature
<222> LOCATION: (61)..(62)
<223> OTHER INFORMATION: n = A,T,C or G
<220> FEATURE:
<221> NAME/KEY: misc_feature
<222> LOCATION: (64)..(65)
<223> OTHER INFORMATION: n = A,T,C or G

<400> SEQUENCE: 88
cgtcctggcc tcatcggcca annsnnsnns nnsnnsnnsn nsnnsnnsnn snnsnnsnns    60
nnsnnsaatg gtccgaccca tgaaaaccaa ctgggc                              96

<210> SEQ ID NO 89
<211> LENGTH: 51
<212> TYPE: DNA
<213> ORGANISM: Artificial Sequence
<220> FEATURE:
<223> OTHER INFORMATION: Synthetic Primer

<400> SEQUENCE: 89
cgtcatctgg ccgatctggc ctgcgtcacc gatgttgttg gtccactggt a             51

<210> SEQ ID NO 90
<211> LENGTH: 60
<212> TYPE: DNA
<213> ORGANISM: Artificial Sequence
<220> FEATURE:
<223> OTHER INFORMATION: Synthetic Primer

<400> SEQUENCE: 90
actgtttctc catacccgtt tttttgggct agcgaattcc gtcctggcct catcggccaa    60

<210> SEQ ID NO 91
<211> LENGTH: 60
<212> TYPE: DNA
<213> ORGANISM: Artificial Sequence
<220> FEATURE:
<223> OTHER INFORMATION: Synthetic Primer

<400> SEQUENCE: 91
ggctgaaaat cttctctcat ccgccaaaac agccaagccg tcatctggcc gatctggcct    60

<210> SEQ ID NO 92
<211> LENGTH: 20
```

<210> SEQ ID NO 92
<211> LENGTH: 20
<212> TYPE: DNA
<213> ORGANISM: Artificial Sequence
<220> FEATURE:
<223> OTHER INFORMATION: Synthetic Primer

<400> SEQUENCE: 92
tcgcaactct ctactgtttc                                                    20

<210> SEQ ID NO 93
<211> LENGTH: 18
<212> TYPE: DNA
<213> ORGANISM: Artificial Sequence
<220> FEATURE:
<223> OTHER INFORMATION: Synthetic Primer

<400> SEQUENCE: 93
ggctgaaaat cttctctc                                                      18

<210> SEQ ID NO 94
<211> LENGTH: 52
<212> TYPE: DNA
<213> ORGANISM: Artificial Sequence
<220> FEATURE:
<223> OTHER INFORMATION: Synthetic Primer

<400> SEQUENCE: 94
tagtagcaaa cgttctggca gatctccaag cgttcaatgt tgtgtctaat tt                 52

<210> SEQ ID NO 95
<211> LENGTH: 53
<212> TYPE: DNA
<213> ORGANISM: Artificial Sequence
<220> FEATURE:
<223> OTHER INFORMATION: Synthetic Primer

<400> SEQUENCE: 95
tgccagaacg tttgctacta cctcgggacg ctcgatggtt ctgttcaatt agc                53

<210> SEQ ID NO 96
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 96

Ser Ala Glu Cys His Pro Gln Gly Pro Pro Cys Ile Glu Gly Arg
1               5                   10                  15

<210> SEQ ID NO 97
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 97

Met Ala Pro Gln Gln
1               5

<210> SEQ ID NO 98
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 98

Met Gly Pro Gln Gln
1               5

<210> SEQ ID NO 99
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 99

Glu Trp Ala Cys Asn Asp Arg Gly Phe Asn Cys Gln Leu Gln Arg
1               5                   10                  15

<210> SEQ ID NO 100
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (2)..(4)
<223> OTHER INFORMATION: Xaa = Any Naturally Occurring Amino Acid

<400> SEQUENCE: 100

Ile Xaa Asn Xaa Arg Gly Phe
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 101

Cys Asn Asp Arg Gly Phe Asn Cys
1               5

<210> SEQ ID NO 102
<211> LENGTH: 519
<212> TYPE: DNA
<213> ORGANISM: Escherichia coli

<400> SEQUENCE: 102
atgaaaaaaa ttgcatgtct ttcagcactg gccgcagttc tggctttcac cgcaggtact    60
tccgtagctg cgacttctac tgtaactggc ggttacgcac agagcgacgc tcagggccaa   120
atgaacaaaa tgggcggttt caacctgaaa taccgctatg aagaagacaa cagcccgctg   180
ggtgtgatcg gttcttttca cttacaccgag aaaagccgta ctgcaagctc tggtgactac   240
aacaaaaacc agtactacgg catcactgct ggtccggctt accgcattaa cgactgggca   300
agcatctacg gtgtagtggg tgtgggttat ggtaaattcc agaccactga atacccgacc   360
tacaaacacg acaccagcga ctacggtttc tcctacggtg cgggtctgca gttcaacccg   420
atggaaaacg ttgctctgga cttctcttac gagcagagcc gtattcgtag cgttgacgta   480
ggcacctgga ttgccggtgt tggttaccgc ttctaataa                         519

<210> SEQ ID NO 103
<211> LENGTH: 40
<212> TYPE: DNA
<213> ORGANISM: Artificial Sequence
<220> FEATURE:
<223> OTHER INFORMATION: Synthetic Primer

<400> SEQUENCE: 103
ttcgagctcg gtacctttga ggtggttatg aaaaaaattg                    40

<210> SEQ ID NO 104
<211> LENGTH: 52
<212> TYPE: DNA
<213> ORGANISM: Artificial Sequence
<220> FEATURE:
<223> OTHER INFORMATION: Synthetic Primer

<400> SEQUENCE: 104
aaaacagcca agcttggcca ccttggcctt attagaagcg gtaaccaaca cc      52

<210> SEQ ID NO 105
<211> LENGTH: 60
<212> TYPE: DNA
<213> ORGANISM: Artificial Sequence
<220> FEATURE:
<223> OTHER INFORMATION: Synthetic Primer

<400> SEQUENCE: 105
gcgagcatga ccggcggcca gcagatgggt ggcgggagtt ctggtgacta caacaaaaac   60

<210> SEQ ID NO 106
<211> LENGTH: 60
<212> TYPE: DNA
<213> ORGANISM: Artificial Sequence
<220> FEATURE:
<223> OTHER INFORMATION: Synthetic Primer

<400> SEQUENCE: 106
ctggccgccg gtcatgctcg ccatttggcc cgactggccg cttgcagtac ggcttttctc   60

<210> SEQ ID NO 107
<211> LENGTH: 40
<212> TYPE: DNA
<213> ORGANISM: Artificial Sequence
<220> FEATURE:
<223> OTHER INFORMATION: Synthetic Primer

<400> SEQUENCE: 107
agaaaagccg tactgcaagc ggcgggagtt ctggtgacta                    40

<210> SEQ ID NO 108
<211> LENGTH: 35
<212> TYPE: DNA
<213> ORGANISM: Artificial Sequence
<220> FEATURE:
<223> OTHER INFORMATION: Synthetic Primer

<400> SEQUENCE: 108
tatctaagct tttattagaa gcggtaacca acacc                         35

<210> SEQ ID NO 109
<211> LENGTH: 96
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (38)..(39)
<223> OTHER INFORMATION: n = A,T,C or G
<220> FEATURE:

```
<221> NAME/KEY: misc_feature
<222> LOCATION: (41)..(42)
<223> OTHER INFORMATION: n = A,T,C or G
<220> FEATURE:
<221> NAME/KEY: misc_feature
<222> LOCATION: (44)..(45)
<223> OTHER INFORMATION: n = A,T,C or G
<220> FEATURE:
<221> NAME/KEY: misc_feature
<222> LOCATION: (47)..(48)
<223> OTHER INFORMATION: n = A,T,C or G
<220> FEATURE:
<221> NAME/KEY: misc_feature
<222> LOCATION: (53)..(54)
<223> OTHER INFORMATION: n = A,T,C or G
<220> FEATURE:
<221> NAME/KEY: misc_feature
<222> LOCATION: (56)..(57)
<223> OTHER INFORMATION: n = A,T,C or G
<220> FEATURE:
<221> NAME/KEY: misc_feature
<222> LOCATION: (59)..(60)
<223> OTHER INFORMATION: n = A,T,C or G
<220> FEATURE:
<221> NAME/KEY: misc_feature
<222> LOCATION: (65)..(66)
<223> OTHER INFORMATION: n = A,T,C or G
<220> FEATURE:
<221> NAME/KEY: misc_feature
<222> LOCATION: (68)..(69)
<223> OTHER INFORMATION: n = A,T,C or G
<220> FEATURE:
<221> NAME/KEY: misc_feature
<222> LOCATION: (71)..(72)
<223> OTHER INFORMATION: n = A,T,C or G
<220> FEATURE:
<221> NAME/KEY: misc_feature
<222> LOCATION: (74)..(75)
<223> OTHER INFORMATION: n = A,T,C or G

<400> SEQUENCE: 109
aagcaagctg caagtccgaa gcggccagtc gggccaanns nnsnnsnnst gcnnsnnsnn    60
stgcnnsnns nnsnnsggcg ggagttctgg tgacta                              96

<210> SEQ ID NO 110
<211> LENGTH: 100
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (30)..(31)
<223> OTHER INFORMATION: n = A,T,C or G
<220> FEATURE:
<221> NAME/KEY: misc_feature
<222> LOCATION: (39)..(40)
<223> OTHER INFORMATION: n = A,T,C or G
<220> FEATURE:
<221> NAME/KEY: misc_feature
<222> LOCATION: (42)..(43)
<223> OTHER INFORMATION: n = A,T,C or G
<220> FEATURE:
<221> NAME/KEY: misc_feature
<222> LOCATION: (45)..(46)
<223> OTHER INFORMATION: n = A,T,C or G
<220> FEATURE:
<221> NAME/KEY: misc_feature
<222> LOCATION: (48)..(49)
<223> OTHER INFORMATION: n = A,T,C or G
<220> FEATURE:
<221> NAME/KEY: misc_feature
<222> LOCATION: (54)..(55)
<223> OTHER INFORMATION: n = A,T,C or G
<220> FEATURE:
<221> NAME/KEY: misc_feature
```

<222> LOCATION: (57)..(58)
<223> OTHER INFORMATION: n = A,T,C or G
<220> FEATURE:
<221> NAME/KEY: misc_feature
<222> LOCATION: (60)..(61)
<223> OTHER INFORMATION: n = A,T,C or G
<220> FEATURE:
<221> NAME/KEY: misc_feature
<222> LOCATION: (63)..(64)
<223> OTHER INFORMATION: n = A,T,C or G
<220> FEATURE:
<221> NAME/KEY: misc_feature
<222> LOCATION: (66)..(67)
<223> OTHER INFORMATION: n = A,T,C or G
<220> FEATURE:
<221> NAME/KEY: misc_feature
<222> LOCATION: (69)..(70)
<223> OTHER INFORMATION: n = A,T,C or G
<220> FEATURE:
<221> NAME/KEY: misc_feature
<222> LOCATION: (72)..(73)
<223> OTHER INFORMATION: n = A,T,C or G
<220> FEATURE:
<221> NAME/KEY: misc_feature
<222> LOCATION: (78)..(79)
<223> OTHER INFORMATION: n = A,T,C or G

<400> SEQUENCE: 110
tgcaagtccg aagcggccag tcgggccaan nstgctgcnn snnsnnsnns tgcnnsnnsn        60
nsnnsnnsnn snnstgcnns ggcgggagtt ctggtgacta                             100

<210> SEQ ID NO 111
<211> LENGTH: 171
<212> TYPE: PRT
<213> ORGANISM: Escherichia coli

<400> SEQUENCE: 111

Met Lys Lys Ile Ala Cys Leu Ser Ala Leu Ala Ala Val Leu Ala Phe
1               5                   10                  15

Thr Ala Gly Thr Ser Val Ala Ala Thr Ser Thr Val Thr Gly Gly Tyr
            20                  25                  30

Ala Gln Ser Asp Ala Gln Gly Gln Met Asn Lys Met Gly Gly Phe Asn
        35                  40                  45

Leu Lys Tyr Arg Tyr Glu Glu Asp Asn Ser Pro Leu Gly Val Ile Gly
    50                  55                  60

Ser Phe Thr Tyr Thr Glu Lys Ser Arg Thr Ala Ser Ser Gly Asp Tyr
65                  70                  75                  80

Asn Lys Asn Gln Tyr Tyr Gly Ile Thr Ala Gly Pro Ala Tyr Arg Ile
                85                  90                  95

Asn Asp Trp Ala Ser Ile Tyr Gly Val Val Gly Val Gly Tyr Gly Lys
            100                 105                 110

Phe Gln Thr Thr Glu Tyr Pro Thr Tyr Lys His Asp Thr Ser Asp Tyr
        115                 120                 125

Gly Phe Ser Tyr Gly Ala Gly Leu Gln Phe Asn Pro Met Glu Asn Val
    130                 135                 140

Ala Leu Asp Phe Ser Tyr Glu Gln Ser Arg Ile Arg Ser Val Asp Val
145                 150                 155                 160

Gly Thr Trp Ile Ala Gly Val Gly Tyr Arg Phe
                165                 170

<210> SEQ ID NO 112
<211> LENGTH: 519
<212> TYPE: DNA
<213> ORGANISM: Escherichia coli

<400> SEQUENCE: 112

| | |
|---|---|
| atgaaaaaaa ttgcatgtct ttcagcactg gccgcagttc tggctttcac cgcaggtact | 60 |
| tccgtagctg cgacttctac tgtaactggc ggttacgcac agagcgacgc tcagggccaa | 120 |
| atgaacaaaa tgggcggttt caacctgaaa taccgctatg aagaagacaa cagcccgctg | 180 |
| ggtgtgatcg gttctttcac ttacaccgag aaaagccgta ctgcaagctc tggtgactac | 240 |
| aacaaaaacc agtactacgg catcactgct ggtccggctt accgcattaa cgactgggca | 300 |
| agcatctacg gtgtagtggg tgtgggttat ggtaaattcc agaccactga atacccgacc | 360 |
| tacaaacacg acaccagcga ctacggtttc tcctacggtg cgggtctgca gttcaacccg | 420 |
| atggaaaacg ttgctctgga cttctcttac gagcagagcc gtattcgtag cgttgacgta | 480 |
| ggcacctgga ttgccggtgt tggttaccgc ttctaataa | 519 |

<210> SEQ ID NO 113
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 113

| | |
|---|---|
| atgaaaaaaa ttgcatgtct ttcagcactg gccgcagttc tggctttcac cgcaggtact | 60 |
| tccgtagctg cgacttctac t | 81 |

<210> SEQ ID NO 114
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 114

| | |
|---|---|
| atggcgagca tgaccggcgg ccagcagatg ggt | 33 |

<210> SEQ ID NO 115
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 115

| | |
|---|---|
| ggaggccagt ctggccag | 18 |

<210> SEQ ID NO 116
<211> LENGTH: 285
<212> TYPE: DNA
<213> ORGANISM: Artificial Sequence
<220> FEATURE:
<223> OTHER INFORMATION: Synthetic Polynucleotide

<400> SEQUENCE: 116

| | |
|---|---|
| tctggtgact acaacaaaaa ccagtactac ggcatcactg ctggtccggc ttaccgcatt | 60 |
| aacgactggg caagcatcta cggtgtagtg ggtgtgggtt atggtaaatt ccagaccact | 120 |
| gaatacccga cctacaaaca cgacaccagc gactacggtt tctcctacgg tgcgggtctg | 180 |
| cagttcaacc cgatggaaaa cgttgctctg gacttctctt acgagcagag ccgtattcgt | 240 |
| agcgttgacg taggcacctg gattgccggt gttggttacc gcttc | 285 |

<210> SEQ ID NO 117
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 117
ggaggaagcg ga                                                         12

<210> SEQ ID NO 118
<211> LENGTH: 159
<212> TYPE: DNA
<213> ORGANISM: Artificial Sequence
<220> FEATURE:
<223> OTHER INFORMATION: Synthetic Polynucleotide

<400> SEQUENCE: 118
gcgacttcta ctgtaactgg cggttacgca cagagcgacg ctcagggcca aatgaacaaa     60
atgggcggtt tcaacctgaa ataccgctat gaagaagaca acagcccgct gggtgtgatc    120
ggttctttca cttacaccga gaaaagccgt actgcaagc                           159

<210> SEQ ID NO 119
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 119 taataa                                                                 6

<210> SEQ ID NO 120
<211> LENGTH: 192
<212> TYPE: PRT
<213> ORGANISM: Artificial Sequence
<220> FEATURE:
<223> OTHER INFORMATION: Synthetic Peptide

<400> SEQUENCE: 120

Met Lys Lys Ile Ala Cys Leu Ser Ala Leu Ala Ala Val Leu Ala Phe
1               5                   10                  15

Thr Ala Gly Thr Ser Val Ala Met Ala Ser Met Thr Gly Gly Gln Gln
            20                  25                  30

Met Gly Gly Gly Gln Ser Gly Gln Ser Gly Asp Tyr Asn Lys Asn Gln
        35                  40                  45

Tyr Tyr Gly Ile Thr Ala Gly Pro Ala Tyr Arg Ile Asn Asp Trp Ala
    50                  55                  60

Ser Ile Tyr Gly Val Val Gly Val Gly Tyr Gly Lys Phe Gln Thr Thr
65                  70                  75                  80

Glu Tyr Pro Thr Tyr Lys His Asp Thr Ser Asp Tyr Gly Phe Ser Tyr
                85                  90                  95

Gly Ala Gly Leu Gln Phe Asn Pro Met Glu Asn Val Ala Leu Asp Phe
            100                 105                 110

Ser Tyr Glu Gln Ser Arg Ile Arg Ser Val Asp Val Gly Thr Trp Ile
        115                 120                 125

Ala Gly Val Gly Tyr Arg Phe Gly Gly Ser Gly Ala Thr Ser Thr Val
    130                 135                 140

Thr Gly Gly Tyr Ala Gln Ser Asp Ala Gln Gly Gln Met Asn Lys Met
145                 150                 155                 160

Gly Gly Phe Asn Leu Lys Tyr Arg Tyr Glu Glu Asp Asn Ser Pro Leu
            165                 170                 175

Gly Val Ile Gly Ser Phe Thr Tyr Thr Glu Lys Ser Arg Thr Ala Ser
            180                 185                 190

<210> SEQ ID NO 121
<211> LENGTH: 576
<212> TYPE: DNA
<213> ORGANISM: Artificial Sequence
<220> FEATURE:
<223> OTHER INFORMATION: Synthetic Polynucleotide

<400> SEQUENCE: 121
atgaaaaaaa ttgcatgtct ttcagcactg gccgcagttc tggctttcac cgcaggtact      60
tccgtagcta cctacaaaca cgacaccagc gactacggtt tctcctacgg tgcgggtctg     120
cagttcaacc cgatggaaaa cgttgctctg gacttctctt acgagcagag ccgtattcgt     180
agcgttgacg taggcacctg gattgccggt gttggttacc gcttcggagg aagcggagcg     240
acttctactg taactggcgg ttacgcacag agcgacgctc agggccaaat gaacaaaatg     300
ggcggtttca acctgaaata ccgctatgaa gaagacaaca gcccgctggg tgtgatcggt     360
tctttcactt acaccgagaa aagccgtact gcaagctctg gtgactacaa caaaaaccag     420
tactacggca tcactgctgg tccggcttac gcattaacg actgggcaag catctacggt     480
gtagtgggtg tgggttatgg taaattccag accactgaat acggaggaag cggaggaatg     540
gcgagcatga ccggcggcca gcagatgggt taataa                              576

<210> SEQ ID NO 122
<211> LENGTH: 190
<212> TYPE: PRT
<213> ORGANISM: Artificial Sequence
<220> FEATURE:
<223> OTHER INFORMATION: Synthetic Peptide

<400> SEQUENCE: 122

Met Lys Lys Ile Ala Cys Leu Ser Ala Leu Ala Ala Val Leu Ala Phe
1               5                   10                  15

Thr Ala Gly Thr Ser Val Ala Thr Tyr Lys His Asp Thr Ser Asp Tyr
            20                  25                  30

Gly Phe Ser Tyr Gly Ala Gly Leu Gln Phe Asn Pro Met Glu Asn Val
            35                  40                  45

Ala Leu Asp Phe Ser Tyr Glu Gln Ser Arg Ile Arg Ser Val Asp Val
    50                  55                  60

Gly Thr Trp Ile Ala Gly Val Gly Tyr Arg Phe Gly Gly Ser Gly Ala
65              70                  75                  80

Thr Ser Thr Val Thr Gly Gly Tyr Ala Gln Ser Asp Ala Gln Gly Gln
            85                  90                  95

Met Asn Lys Met Gly Gly Phe Asn Leu Lys Tyr Arg Tyr Glu Glu Asp
            100                 105                 110

Asn Ser Pro Leu Gly Val Ile Gly Ser Phe Thr Tyr Thr Glu Lys Ser
        115                 120                 125

Arg Thr Ala Ser Ser Gly Asp Tyr Asn Lys Asn Gln Tyr Tyr Gly Ile
    130                 135                 140

Thr Ala Gly Pro Ala Tyr Arg Ile Asn Asp Trp Ala Ser Ile Tyr Gly
145                 150                 155                 160

Val Val Gly Val Gly Tyr Gly Lys Phe Gln Thr Thr Glu Tyr Gly Gly
            165                 170                 175

Ser Gly Gly Met Ala Ser Met Thr Gly Gly Gln Gln Met Gly
        180                 185                 190

<210> SEQ ID NO 123
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 123
atggcgagca tgaccggcgg ccagcagatg ggt                                33

<210> SEQ ID NO 124
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 124

Met Ala Ser Met Thr Gly Gly Gln Gln Met Gly
1               5                   10

<210> SEQ ID NO 125
<211> LENGTH: 45
<212> TYPE: PRT
<213> ORGANISM: Artificial Sequence
<220> FEATURE:
<223> OTHER INFORMATION: Synthetic Peptide

<400> SEQUENCE: 125

Ala Cys Cys Gly Thr Gly Cys Thr Gly Ala Thr Thr Gly Cys Ala
1               5                   10                  15

Thr Gly Ala Ala Cys Ala Thr Cys Thr Gly Thr Thr Gly Gly Ala Cys
            20                  25                  30

Gly Gly Gly Cys Gly Ala Ala Ala Cys Thr Cys Ala Gly
        35                  40                  45

<210> SEQ ID NO 126
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 126

Thr Val Leu Ile Cys Met Asn Ile Cys Trp Thr Gly Glu Thr Gln
1               5                   10                  15

<210> SEQ ID NO 127
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 127
ttcgagctcg gtacctttga ggtggtt                                       27

<210> SEQ ID NO 128
<211> LENGTH: 69
<212> TYPE: DNA
<213> ORGANISM: Artificial Sequence
<220> FEATURE:

<223> OTHER INFORMATION: Synthetic Oligonucleotide

<400> SEQUENCE: 128
atgaaaaaaa ttgcatgtct ttcagcactg gccgcagttc tggctttcac cgcaggtact    60
tccgtagct                                                            69

<210> SEQ ID NO 129
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 129

Met Lys Lys Ile Ala Cys Leu Ser Ala Leu Ala Ala Val Leu Ala Phe
1               5                   10                  15

Thr Ala Gly Thr Ser Val Ala
            20

<210> SEQ ID NO 130
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 130
ggccaaggtg gccaagcttg gctgtttt                                       28

<210> SEQ ID NO 131
<211> LENGTH: 60
<212> TYPE: DNA
<213> ORGANISM: Artificial Sequence
<220> FEATURE:
<223> OTHER INFORMATION: Synthetic Primer

<400> SEQUENCE: 131
ttcgagctcg gtacctttga ggtggttatg aaaaaaattg catgtctttc agcactggcc    60

<210> SEQ ID NO 132
<211> LENGTH: 60
<212> TYPE: DNA
<213> ORGANISM: Artificial Sequence
<220> FEATURE:
<223> OTHER INFORMATION: Synthetic Primer

<400> SEQUENCE: 132
tttcagcagt ggccgcagtt ctggctttca ccgcaggtac ttccgtagct atggcgagca    60

<210> SEQ ID NO 133
<211> LENGTH: 60
<212> TYPE: DNA
<213> ORGANISM: Artificial Sequence
<220> FEATURE:
<223> OTHER INFORMATION: Synthetic Primer

<400> SEQUENCE: 133
agctatggcg agcatgaccg gcggccagca gatgggtgga ggaagcggag gatctggtga    60

<210> SEQ ID NO 134
<211> LENGTH: 60
<212> TYPE: DNA
<213> ORGANISM: Artificial Sequence
<220> FEATURE:
<223> OTHER INFORMATION: Synthetic Primer

<400> SEQUENCE: 134
cggaggatct ggtgactaca acaaaaacca gtactacggc atcactgctg gtccggctta    60

<210> SEQ ID NO 135
<211> LENGTH: 60
<212> TYPE: DNA
<213> ORGANISM: Artificial Sequence
<220> FEATURE:
<223> OTHER INFORMATION: Synthetic Primer

<400> SEQUENCE: 135
gctggtccgg cttaccgcat taacgactgg gcaagcatct acggtgtagt gggtgtgggt    60

<210> SEQ ID NO 136
<211> LENGTH: 60
<212> TYPE: DNA
<213> ORGANISM: Artificial Sequence
<220> FEATURE:
<223> OTHER INFORMATION: Synthetic Primer

<400> SEQUENCE: 136
gtagtgggtg tgggttatgg taaattccag accactgaat acccgaccta caaacacgac    60

<210> SEQ ID NO 137
<211> LENGTH: 60
<212> TYPE: DNA
<213> ORGANISM: Artificial Sequence
<220> FEATURE:
<223> OTHER INFORMATION: Synthetic Primer

<400> SEQUENCE: 137
cgacctacaa acacgacacc agcgactacg gtttctccta cggtgcgggt ctgcagttca    60

<210> SEQ ID NO 138
<211> LENGTH: 60
<212> TYPE: DNA
<213> ORGANISM: Artificial Sequence
<220> FEATURE:
<223> OTHER INFORMATION: Synthetic Primer

<400> SEQUENCE: 138
cgggtctgca gttcaacccg atggaaaacg ttgctctgga cttctcttac gagcagagcc    60

<210> SEQ ID NO 139
<211> LENGTH: 60
<212> TYPE: DNA
<213> ORGANISM: Artificial Sequence
<220> FEATURE:
<223> OTHER INFORMATION: Synthetic Primer

<400> SEQUENCE: 139
cttacgagca gagccgtatt cgtagcgttg acgtaggcac ctggattgcc ggtgttggtt    60

<210> SEQ ID NO 140
<211> LENGTH: 60
<212> TYPE: DNA
<213> ORGANISM: Artificial Sequence
<220> FEATURE:
<223> OTHER INFORMATION: Synthetic Primer

<400> SEQUENCE: 140
tgccggtgtt ggttaccgct tcggaggaag cggagcgact tctactgtaa ctggcggtta    60

<210> SEQ ID NO 141

<211> LENGTH: 60
<212> TYPE: DNA
<213> ORGANISM: Artificial Sequence
<220> FEATURE:
<223> OTHER INFORMATION: Synthetic Primer

<400> SEQUENCE: 141
ctgtaactgg cggttacgca cagagcgacg ctcagggcca aatgaacaaa atgggcggtt    60

<210> SEQ ID NO 142
<211> LENGTH: 60
<212> TYPE: DNA
<213> ORGANISM: Artificial Sequence
<220> FEATURE:
<223> OTHER INFORMATION: Synthetic Primer

<400> SEQUENCE: 142
acaaaatggg cggtttcaac ctgaaatacc gctatgaaga agacaacagc ccgctgggtg    60

<210> SEQ ID NO 143
<211> LENGTH: 60
<212> TYPE: DNA
<213> ORGANISM: Artificial Sequence
<220> FEATURE:
<223> OTHER INFORMATION: Synthetic Primer

<400> SEQUENCE: 143
gcccgctggg tgtgatcggt tctttcactt acaccgagaa aagccgtact gcaagctaat    60

<210> SEQ ID NO 144
<211> LENGTH: 47
<212> TYPE: DNA
<213> ORGANISM: Artificial Sequence
<220> FEATURE:
<223> OTHER INFORMATION: Synthetic Primer

<400> SEQUENCE: 144
aaaacagcca agcttggcca ccttggcctt attagcttgc agtacgg                  47

<210> SEQ ID NO 145
<211> LENGTH: 96
<212> TYPE: DNA
<213> ORGANISM: Artificial Sequence
<220> FEATURE:
<223> OTHER INFORMATION: Synthetic Oligonucleotide

<400> SEQUENCE: 145
ttcgagctcg gtacctttga ggtggttatg aaaaaaattg catgtctttc agcactggcc    60
gcagttctgg ctttcaccgc aggtacttcc gtagct                              96

<210> SEQ ID NO 146
<211> LENGTH: 159
<212> TYPE: DNA
<213> ORGANISM: Artificial Sequence
<220> FEATURE:
<223> OTHER INFORMATION: Synthetic Oligonucleotide

<400> SEQUENCE: 146
gcgacttcta ctgtaactgg cggttacgca cagagcgacg ctcagggcca aatgaacaaa    60
atgggcggtt tcaacctgaa ataccgctat gaagaagaca acagcccgct gggtgtgatc   120
ggttctttca cttacaccga gaaaagccgt actgcaagc                          159

<210> SEQ ID NO 147
<211> LENGTH: 129

```
<212> TYPE: DNA
<213> ORGANISM: Artificial Sequence
<220> FEATURE:
<223> OTHER INFORMATION: Synthetic Oligonucleotide

<400> SEQUENCE: 147
tctggtgact acaacaaaaa ccagtactac ggcatcactg ctggtccggc ttaccgcatt    60
aacgactggg caagcatcta cggtgtagtg ggtgtgggtt atggtaaatt ccagaccact   120
gaatacccg                                                          129

<210> SEQ ID NO 148
<211> LENGTH: 162
<212> TYPE: DNA
<213> ORGANISM: Artificial Sequence
<220> FEATURE:
<223> OTHER INFORMATION: Synthetic Oligonucleotide

<400> SEQUENCE: 148
acctacaaac acgacaccag cgactacggt ttctcctacg gtgcgggtct gcagttcaac    60
ccgatggaaa acgttgctct ggacttctct tacgagcaga gccgtattcg tagcgttgac   120
gtaggcacct ggattgccgg tgttggttac cgcttctaat aa                     162

<210> SEQ ID NO 149
<211> LENGTH: 621
<212> TYPE: DNA
<213> ORGANISM: Artificial Sequence
<220> FEATURE:
<223> OTHER INFORMATION: Synthetic Polynucleotide

<400> SEQUENCE: 149
ttcgagctcg gtacctttga ggtggttatg aaaaaaattg catgtctttc agcactggcc    60
gcagttctgg ctttcaccgc aggtacttcc gtagctgcga cttctactat ggcgagcatg   120
accggcggcc agcagatggg tggaggccag tctggccagt ctggtgacta caacaaaaac   180
cagtactacg gcatcactgc tggtccggct taccgcatta acgactgggc aagcatctac   240
ggtgtagtgg gtgtgggtta tggtaaattc cagaccactg aatacccgac ctacaaacac   300
gacaccagcg actacggttt ctcctacggt gcgggtctgc agttcaaccc gatggaaaac   360
gttgctctgg acttctctta cgagcagagc cgtattcgta gcgttgacgt aggcacctgg   420
attgccggtg ttggttaccg cttcggagga agcggagcgc ttctactgt aactggcggt   480 tacgcacaga gcgacgctca gggccaaatg aacaaatgg gcggtttcaa cctgaaatac   540
cgctatgaag aagacaacag cccgctgggt gtgatcggtt ctttcactta caccgagaaa   600
agccgtactg caagctaata a                                            621

<210> SEQ ID NO 150
<211> LENGTH: 96
<212> TYPE: DNA
<213> ORGANISM: Artificial Sequence
<220> FEATURE:
<223> OTHER INFORMATION: Synthetic Oligonucleotide

<400> SEQUENCE: 150
ttcgagctcg gtacctttga ggtggttatg aaaaaaattg catgtctttc agcactggcc    60
gcagttctgg ctttcaccgc aggtacttcc gtagct                             96

<210> SEQ ID NO 151
<211> LENGTH: 159
<212> TYPE: DNA
```

<213> ORGANISM: Artificial Sequence
<220> FEATURE:
<223> OTHER INFORMATION: Synthetic Oligonucleotide

<400> SEQUENCE: 151
gcgacttcta ctgtaactgg cggttacgca cagagcgacg ctcagggcca aatgaacaaa        60
atgggcggtt tcaacctgaa ataccgctat gaagaagaca acagcccgct gggtgtgatc       120
ggttctttca cttacaccga gaaaagccgt actgcaagc                              159

<210> SEQ ID NO 152
<211> LENGTH: 126
<212> TYPE: DNA
<213> ORGANISM: Artificial Sequence
<220> FEATURE:
<223> OTHER INFORMATION: Synthetic Oligonucleotide

<400> SEQUENCE: 152
tctggtgact acaacaaaaa ccagtactac ggcatcactg ctggtccggc ttaccgcatt        60
aacgactggg caagcatcta cggtgtagtg ggtgtgggtt atggtaaatt ccagaccact       120
gaatac                                                                  126

<210> SEQ ID NO 153
<211> LENGTH: 162
<212> TYPE: DNA
<213> ORGANISM: Artificial Sequence
<220> FEATURE:
<223> OTHER INFORMATION: Synthetic Oligonucleotide

<400> SEQUENCE: 153
acctacaaac acgacaccag cgactacggt ttctcctacg gtgcgggtct gcagttcaac        60
ccgatggaaa acgttgctct ggacttctct tacgagcaga gccgtattcg tagcgttgac       120
gtaggcacct ggattgccgg tgttggttac cgcttctaat aa                          162

<210> SEQ ID NO 154
<211> LENGTH: 45
<212> TYPE: DNA
<213> ORGANISM: Artificial Sequence
<220> FEATURE:
<223> OTHER INFORMATION: Synthetic Primer

<400> SEQUENCE: 154
ttcgagctcg gtacctttga ggtggttatg aaaaaaattg catgt                        45

<210> SEQ ID NO 155
<211> LENGTH: 57
<212> TYPE: DNA
<213> ORGANISM: Artificial Sequence
<220> FEATURE:
<223> OTHER INFORMATION: Synthetic Primer

<400> SEQUENCE: 155
gcggtgaaag ccagaactgc ggccagtgct gaaagacatg caatttttt cataacc           57

<210> SEQ ID NO 156
<211> LENGTH: 57
<212> TYPE: DNA
<213> ORGANISM: Artificial Sequence
<220> FEATURE:
<223> OTHER INFORMATION: Synthetic Primer

<400> SEQUENCE: 156
tggctttcac cgcaggtact tccgtagcta cctacaaaca cgacaccagc gactacg          57

<210> SEQ ID NO 157
<211> LENGTH: 57
<212> TYPE: DNA
<213> ORGANISM: Artificial Sequence
<220> FEATURE:
<223> OTHER INFORMATION: Synthetic Primer

<400> SEQUENCE: 157
ttttccatcg ggttgaactg cagacccgca ccgtaggaga aaccgtagtc gctggtg    57

<210> SEQ ID NO 158
<211> LENGTH: 57
<212> TYPE: DNA
<213> ORGANISM: Artificial Sequence
<220> FEATURE:
<223> OTHER INFORMATION: Synthetic Primer

<400> SEQUENCE: 158
ttcaacccga tggaaaacgt tgctctggac ttctcttacg agcagagccg tattcgt    57

<210> SEQ ID NO 159
<211> LENGTH: 57
<212> TYPE: DNA
<213> ORGANISM: Artificial Sequence
<220> FEATURE:
<223> OTHER INFORMATION: Synthetic Primer

<400> SEQUENCE: 159
gcggtaacca acaccggcaa tccaggtgcc tacgtcaacg ctacgaatac ggctctg    57

<210> SEQ ID NO 160
<211> LENGTH: 57
<212> TYPE: DNA
<213> ORGANISM: Artificial Sequence
<220> FEATURE:
<223> OTHER INFORMATION: Synthetic Primer

<400> SEQUENCE: 160
ggtgttggtt accgcttcgg aggaagcgga gcgacttcta ctgtaactgg cggttac    57

<210> SEQ ID NO 161
<211> LENGTH: 57
<212> TYPE: DNA
<213> ORGANISM: Artificial Sequence
<220> FEATURE:
<223> OTHER INFORMATION: Synthetic Primer

<400> SEQUENCE: 161
ccgcccattt tgttcatttg gccctgagcg tcgctctgtg cgtaaccgcc agttaca    57

<210> SEQ ID NO 162
<211> LENGTH: 57
<212> TYPE: DNA
<213> ORGANISM: Artificial Sequence
<220> FEATURE:
<223> OTHER INFORMATION: Synthetic Primer

<400> SEQUENCE: 162
gaacaaaatg ggcggtttca acctgaaata ccgctatgaa gaagacaaca gcccgct    57

<210> SEQ ID NO 163
<211> LENGTH: 57
<212> TYPE: DNA
<213> ORGANISM: Artificial Sequence
<220> FEATURE:

<223> OTHER INFORMATION: Synthetic Primer

<400> SEQUENCE: 163
cagtacggct tttctcggtg taagtgaaag aaccgatcac acccagcggg ctgttgt        57

<210> SEQ ID NO 164
<211> LENGTH: 57
<212> TYPE: DNA
<213> ORGANISM: Artificial Sequence
<220> FEATURE:
<223> OTHER INFORMATION: Synthetic Primer

<400> SEQUENCE: 164
cgagaaaagc cgtactgcaa gctctggtga ctacaacaaa aaccagtact acggcat        57

<210> SEQ ID NO 165
<211> LENGTH: 57
<212> TYPE: DNA
<213> ORGANISM: Artificial Sequence
<220> FEATURE:
<223> OTHER INFORMATION: Synthetic Primer

<400> SEQUENCE: 165
tgcttgccca gtcgttaatg cggtaagccg gaccagcagt gatgccgtag tactggt        57

<210> SEQ ID NO 166
<211> LENGTH: 57
<212> TYPE: DNA
<213> ORGANISM: Artificial Sequence
<220> FEATURE:
<223> OTHER INFORMATION: Synthetic Primer

<400> SEQUENCE: 166
cgactgggca agcatctacg gtgtagtggg tgtgggttat ggtaaattcc agaccac        57

<210> SEQ ID NO 167
<211> LENGTH: 57
<212> TYPE: DNA
<213> ORGANISM: Artificial Sequence
<220> FEATURE:
<223> OTHER INFORMATION: Synthetic Primer

<400> SEQUENCE: 167
ccggtcatgc tcgccattcc tccgcttcct ccgtattcag tggtctggaa tttacca        57

<210> SEQ ID NO 168
<211> LENGTH: 57
<212> TYPE: DNA
<213> ORGANISM: Artificial Sequence
<220> FEATURE:
<223> OTHER INFORMATION: Synthetic Primer

<400> SEQUENCE: 168
cgagcatgac cggcggccag cagatgggtt aataaggcca aggtggccaa gcttggc        57

<210> SEQ ID NO 169
<211> LENGTH: 19
<212> TYPE: DNA
<213> ORGANISM: Artificial Sequence
<220> FEATURE:
<223> OTHER INFORMATION: Synthetic Primer

<400> SEQUENCE: 169
aaaacagcca agcttggcc        19

<210> SEQ ID NO 170
<211> LENGTH: 603
<212> TYPE: DNA
<213> ORGANISM: Artificial Sequence
<220> FEATURE:
<223> OTHER INFORMATION: Synthetic Polynucleotide

<400> SEQUENCE: 170

```
ttcgagctcg gtacctttga ggtggttatg aaaaaaattg catgtctttc agcactggcc      60
gcagttctgg ctttcaccgc aggtacttcc gtagctacct acaaacacga caccagcgac     120
tacggtttct cctacggtgc gggtctgcag ttcaacccga tggaaaacgt tgctctggac     180
ttctcttacg agcagagccg tattcgtagc gttgacgtag gcacctggat tgccggtgtt     240
ggttaccgct tcggaggaag cggagcgact tctactgtaa ctggcggtta cgcacagagc     300
gacgctcagg gccaaatgaa caaaatgggc ggtttcaacc tgaaataccg ctatgaagaa     360
gacaacagcc cgctgggtgt gatcggttct ttcacttaca ccgagaaaag ccgtactgca     420
agctctggtg actacaacaa aaaccagtac tacggcatca ctgctggtcc ggcttaccgc     480
attaacgact gggcaagcat ctacggtgta gtgggtgtgg gttatggtaa attccagacc     540
actgaatacg aggaagcgg aggaatggcg agcatgaccg cggccagca gatgggttaa      600
taa                                                                   603
```

<210> SEQ ID NO 171
<211> LENGTH: 20
<212> TYPE: DNA
<213> ORGANISM: Artificial Sequence
<220> FEATURE:
<223> OTHER INFORMATION: Synthetic Primer

<400> SEQUENCE: 171

```
tcgcaactct ctactgtttc                                                  20
```

<210> SEQ ID NO 172
<211> LENGTH: 18
<212> TYPE: DNA
<213> ORGANISM: Artificial Sequence
<220> FEATURE:
<223> OTHER INFORMATION: Synthetic Primer

<400> SEQUENCE: 172

```
ggctgaaaat cttctctc                                                    18
```

<210> SEQ ID NO 173
<211> LENGTH: 40
<212> TYPE: DNA
<213> ORGANISM: Artificial Sequence
<220> FEATURE:
<223> OTHER INFORMATION: Synthetic Primer

<400> SEQUENCE: 173

```
ttcgagctcg gtacctttga ggtggttatg aaaaaaattg                            40
```

<210> SEQ ID NO 174
<211> LENGTH: 45
<212> TYPE: DNA
<213> ORGANISM: Artificial Sequence
<220> FEATURE:
<223> OTHER INFORMATION: Synthetic Primer

<400> SEQUENCE: 174

```
cagtagaagt cgctccgctt cctccgaagc ggtaaccaac accgg                      45
```

<210> SEQ ID NO 175
<211> LENGTH: 45
<212> TYPE: DNA
<213> ORGANISM: Artificial Sequence
<220> FEATURE:
<223> OTHER INFORMATION: Synthetic Primer

<400> SEQUENCE: 175
ggaggaagcg gagcgacttc tactgtaact ggcggttacg cacag        45

<210> SEQ ID NO 176
<211> LENGTH: 56
<212> TYPE: DNA
<213> ORGANISM: Artificial Sequence
<220> FEATURE:
<223> OTHER INFORMATION: Synthetic Primer

<400> SEQUENCE: 176
aaaacagcca agcttggcca ccttggcctt attagcttgc agtacggctt ttctcg        56

<210> SEQ ID NO 177
<211> LENGTH: 60
<212> TYPE: DNA
<213> ORGANISM: Artificial Sequence
<220> FEATURE:
<223> OTHER INFORMATION: Synthetic Primer

<400> SEQUENCE: 177
gttatgaaaa aaattgcatg trtttcagca rttgccgcag ttrttgcttt caccgcaggt        60

<210> SEQ ID NO 178
<211> LENGTH: 48
<212> TYPE: DNA
<213> ORGANISM: Artificial Sequence
<220> FEATURE:
<223> OTHER INFORMATION: Synthetic Primer

<400> SEQUENCE: 178
tgttgtcttc ttcatagcgg tatttaaygt tgaaaccgcc cattttgt        48

<210> SEQ ID NO 179
<211> LENGTH: 48
<212> TYPE: DNA
<213> ORGANISM: Artificial Sequence
<220> FEATURE:
<223> OTHER INFORMATION: Synthetic Primer

<400> SEQUENCE: 179
ccgctatgaa gaagacaaca gcccgrttgg tgtgatcggt tctttcac        48

<210> SEQ ID NO 180
<211> LENGTH: 47
<212> TYPE: DNA
<213> ORGANISM: Artificial Sequence
<220> FEATURE:
<223> OTHER INFORMATION: Synthetic Primer

<400> SEQUENCE: 180
aacgttttcc atcgggttga actgaayacc cgcaccgtag gagaaac        47

<210> SEQ ID NO 181
<211> LENGTH: 47
<212> TYPE: DNA
<213> ORGANISM: Artificial Sequence
<220> FEATURE:
<223> OTHER INFORMATION: Synthetic Primer

<400> SEQUENCE: 181
ttcaacccga tggaaaacgt tgctrttgac ttctcttacg agcagag    47

<210> SEQ ID NO 182
<211> LENGTH: 51
<212> TYPE: DNA
<213> ORGANISM: Artificial Sequence
<220> FEATURE:
<223> OTHER INFORMATION: Synthetic Primer

<400> SEQUENCE: 182
ctgcccagac tgccctccct ggccagactg gccagctacg gaagtacctg c    51

<210> SEQ ID NO 183
<211> LENGTH: 36
<212> TYPE: DNA
<213> ORGANISM: Artificial Sequence
<220> FEATURE:
<223> OTHER INFORMATION: Synthetic Primer

<400> SEQUENCE: 183
ggagggcagt ctgggcagtc tggtgactac aacaaa    36

<210> SEQ ID NO 184
<211> LENGTH: 80
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (24)..(25)
<223> OTHER INFORMATION: n = A,T,C or G
<220> FEATURE:
<221> NAME/KEY: misc_feature
<222> LOCATION: (27)..(28)
<223> OTHER INFORMATION: n = A,T,C or G
<220> FEATURE:
<221> NAME/KEY: misc_feature
<222> LOCATION: (33)..(34)
<223> OTHER INFORMATION: n = A,T,C or G
<220> FEATURE:
<221> NAME/KEY: misc_feature
<222> LOCATION: (36)..(37)
<223> OTHER INFORMATION: n = A,T,C or G
<220> FEATURE:
<221> NAME/KEY: misc_feature
<222> LOCATION: (39)..(40)
<223> OTHER INFORMATION: n = A,T,C or G
<220> FEATURE:
<221> NAME/KEY: misc_feature
<222> LOCATION: (42)..(43)
<223> OTHER INFORMATION: n = A,T,C or G
<220> FEATURE:
<221> NAME/KEY: misc_feature
<222> LOCATION: (42)..(43)
<223> OTHER INFORMATION: n = A,T,C or G
<220> FEATURE:
<221> NAME/KEY: misc_feature
<222> LOCATION: (45)..(46)
<223> OTHER INFORMATION: n = A,T,C or G
<220> FEATURE:
<221> NAME/KEY: misc_feature
<222> LOCATION: (48)..(49)
<223> OTHER INFORMATION: n = A,T,C or G
<220> FEATURE:
<221> NAME/KEY: misc_feature
<222> LOCATION: (51)..(52)
<223> OTHER INFORMATION: n = A,T,C or G
<220> FEATURE:
<221> NAME/KEY: misc_feature
<222> LOCATION: (57)..(58)

<223> OTHER INFORMATION: n = A,T,C or G
<220> FEATURE:
<221> NAME/KEY: misc_feature
<222> LOCATION: (60)..(61)
<223> OTHER INFORMATION: n = A,T,C or G

<400> SEQUENCE: 184
ctgactgagg ccagtctggc cagnnsnnst gcnnsnnsnn snnsnnsnns nnstgcnnsn    60
nsggagggca gtctgggcag                                                80

<210> SEQ ID NO 185
<211> LENGTH: 40
<212> TYPE: DNA
<213> ORGANISM: Artificial Sequence
<220> FEATURE:
<223> OTHER INFORMATION: Synthetic Primer

<400> SEQUENCE: 185
gctttcaccg caggtacttc tgactgaggc cagtctggcc                          40

<210> SEQ ID NO 186
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 186

Thr Val Leu Ile Cys Met Asn Ile Cys Trp Thr Gly Glu Thr Gln
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 187

Leu Pro Val Trp Cys Val Met His Val Cys Leu Thr Ser Ser Arg
1               5                   10                  15

<210> SEQ ID NO 188
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 188

Trp Val Cys Thr Trp Asn Tyr Trp Thr Arg Val Thr Trp Cys Leu
1               5                   10                  15

<210> SEQ ID NO 189
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 189

Cys Trp Tyr Gln Trp Cys Gly Tyr Tyr Tyr Ser Tyr Asn Cys His
1               5                   10                  15

<210> SEQ ID NO 190
<211> LENGTH: 15

<212> TYPE: PRT
<213> ORGANISM: Artificial Sequence
<220> FEATURE:
<223> OTHER INFORMATION: Synthetic Peptide

<400> SEQUENCE: 190

Glu Trp Ala Cys Asn Asp Arg Gly Phe Asn Cys Gln Leu Gln Arg
1               5                   10                  15

<210> SEQ ID NO 191
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 191

Thr Thr Cys Lys Tyr Tyr Leu Ser Cys Arg Trp Arg Lys Asp Leu
1               5                   10                  15

<210> SEQ ID NO 192
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 192

Arg His Leu Tyr Cys Trp Thr Trp Arg Trp Cys His Phe Lys Asp
1               5                   10                  15

<210> SEQ ID NO 193
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 193

Asn Pro Phe Cys Ser Trp Tyr Arg Trp Arg Asn Trp Cys Thr Lys
1               5                   10                  15

<210> SEQ ID NO 194
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 194

Thr Glu Tyr Pro Thr Tyr Lys Asn
1               5

<210> SEQ ID NO 195
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 195

Ser Arg Thr Ala Ser Ser Gly
1               5

<210> SEQ ID NO 196
<211> LENGTH: 15
<212> TYPE: PRT

```
<213> ORGANISM: Artificial Sequence
<220> FEATURE:
<223> OTHER INFORMATION: Synthetic Peptide

<400> SEQUENCE: 196

Gln Gly Arg Val Met Gly Pro Gln Gln Leu Tyr Val Met Met Arg
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 197

Asn Ser Leu Ser Met Ala Pro Gln Gln Gly Trp Val Gln Thr Gly
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 198

Thr Asn Lys Leu Met Gly Pro Gln Gln Ser Lys Met Phe Tyr Trp
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 199

Gly Glu Gly Val Met Ser Pro Thr Gln Gln Arg Gly Pro Ala Arg
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 200

Ala Ile Val Val Ser Met Thr Pro Phe Gln Gln Trp Ser Leu Ser
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 201

Ala Val His Ala Arg His Tyr Thr Pro Trp Gln Gln Leu Tyr Ser
1               5                   10                  15

<210> SEQ ID NO 202
<211> LENGTH: 15
<212> TYPE: PRT
<213> ORGANISM: Artificial Sequence
```

```
<220> FEATURE:
<223> OTHER INFORMATION: Synthetic Peptide

<400> SEQUENCE: 202

Glu Arg Thr Gly Thr Tyr Ser Pro Trp Gln Gln Leu Arg Val Glu
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 203

Gln Gln Leu Ser Tyr Gly Pro Gln Gln His Ala His Met Gly
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 204

Pro Met Ala Ile Ile Gly Pro Gln Gln Met His Leu Val Leu His
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 205

Val Tyr Lys Ser Met Ala Pro Gln Gln Thr Asn Ala Trp Gln His
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 206

Leu Gln Tyr Ser Thr Ala Met Gly Pro Gln Gln Met Thr Ser Trp
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 207

Gly Ser Thr Ser Met Gly Pro Gln Gln Phe Ala Trp Gly Thr Leu
1               5                   10                  15

<210> SEQ ID NO 208
<211> LENGTH: 15
<212> TYPE: PRT
<213> ORGANISM: Artificial Sequence
<220> FEATURE:
```

<223> OTHER INFORMATION: Synthetic Peptide

<400> SEQUENCE: 208

Gln Lys Ser Thr Met Thr Gly Trp Gln Gln Met Gly Val Met Gly
1               5                   10                  15

<210> SEQ ID NO 209
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 209

Ser Ala Glu Cys His Pro Gln Gly Pro Pro Cys Ile Glu Gly Arg
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 210

Ala Tyr Met Ser Tyr Ser Gly Phe Gln Gln Thr Ala Arg Trp Arg
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 211

Ser Ser Ala Ser Tyr Ala Gly Trp Gln Gln Met Lys Thr Met Gly
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 212

Gly Thr Val Ser Tyr Ser Gly Tyr Gln Gln Trp Ala Gln Arg Ile
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 213

Ser Pro Ala Leu Met Ser Pro Trp Gln Val Ser Arg Ser Leu Cys
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 214

Pro Thr Arg Ala Met Ser Pro Leu Gln Ala Leu His Leu Glu Lys
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 215

Gln Gln Leu Ser Tyr Gly Pro Gln Gln His Ala His Met Gly
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 216

Pro Met Ala Ile Ile Gly Pro Gln Gln Met His Leu Val Leu His
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 217

Val Tyr Lys Ser Met Ala Pro Gln Gln Thr Asn Ala Trp Gln His
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 218

Leu Gln Tyr Ser Thr Ala Met Gly Pro Gln Gln Met Thr Ser Trp
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 219

Gly Ser Thr Ser Met Gly Pro Gln Gln Phe Ala Trp Gly Thr Leu
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: Synthetic Peptide

```
<400> SEQUENCE: 220

Thr Cys Leu Arg Gly Pro Gln Gln Thr Arg Trp Cys Ile Ser Arg
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 221

Ser Thr Tyr Arg Pro Met Ala Arg Gln Gln Thr Val Leu Phe Phe
1               5                   10                  15

<210> SEQ ID NO 222
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 222

Pro Gln Pro His Ser Leu Met Thr Pro Arg Gln Gln Met Pro Met Leu
1               5                   10                  15

Thr Glu Met

<210> SEQ ID NO 223
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 223

Gln Lys Ser Thr Met Thr Gly Trp Gln Gln Met Gly Val Met Gly
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 224

Ala Val His Ala Arg His Tyr Thr Pro Trp Gln Gln Leu Tyr Ser
1               5                   10                  15

<210> SEQ ID NO 225
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 225

Glu Arg Thr Gly Thr Tyr Ser Pro Trp Gln Gln Leu Arg Val Glu
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: Synthetic Peptide
```

```
<400> SEQUENCE: 226

Gln Gly Arg Val Met Gly Pro Gln Gln Leu Tyr Val Met Met Arg
1               5                   10                  15

<210> SEQ ID NO 227
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 227

Asn Ser Leu Ser Met Ala Pro Gln Gln Gly Trp Val Gln Thr Gly
1               5                   10                  15

<210> SEQ ID NO 228
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 228

Thr Asn Lys Leu Met Gly Pro Gln Gln Ser Lys Met Phe Tyr Trp
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 229

Gly Glu Gly Val Met Ser Pro Thr Gln Gln Arg Gly Pro Ala Arg
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 230

Ala Ile Val Val Ser Met Thr Pro Phe Gln Gln Trp Ser Leu Ser
1               5                   10                  15

<210> SEQ ID NO 231
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 231

Gly Ser Met Ala Ser Met Thr Gly Gly Gln Gln Met Gly Ser Gly
1               5                   10                  15

<210> SEQ ID NO 232
<211> LENGTH: 15
<212> TYPE: PRT
<213> ORGANISM: Artificial Sequence
<220> FEATURE:
<223> OTHER INFORMATION: Synthetic Peptide
```

<400> SEQUENCE: 232

Arg Leu Glu Ile Cys Gln Asn Val Cys Tyr Tyr Leu Gly Thr Leu
1               5                   10                  15

<210> SEQ ID NO 233
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 233

Thr Val Leu Ile Cys Met Asn Ile Cys Trp Thr Gly Glu Thr Gln
1               5                   10                  15

<210> SEQ ID NO 234
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 234

Ile Cys Ser Tyr Val Met Tyr Thr Thr Cys Phe Leu Arg Val Tyr
1               5                   10                  15

<210> SEQ ID NO 235
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 235

Arg Leu Glu Ile Cys Gln Asn Val Cys Tyr Tyr Leu Gly Thr Leu
1               5                   10                  15

<210> SEQ ID NO 236
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 236

Thr Val Leu Ile Cys Met Asn Ile Cys Trp Thr Gly Glu Thr Gln
1               5                   10                  15

<210> SEQ ID NO 237
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 237

Ile Cys Ser Tyr Val Met Tyr Thr Thr Cys Phe Leu Arg Val Tyr
1               5                   10                  15

<210> SEQ ID NO 238
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 238

```
Tyr Trp Val Cys Met Asn Val Cys Met Tyr Tyr Thr Ala Arg Gln
1               5                   10                  15

<210> SEQ ID NO 239
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 239

Leu Pro Val Trp Cys Val Met His Val Cys Leu Thr Ser Ser Arg
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 240

Val Thr Ser Leu Cys Met Asn Val Cys Tyr Ser Leu Thr Thr Tyr
1               5                   10                  15

<210> SEQ ID NO 241
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 241

Asn Glu Trp Tyr Cys Gln Asn Val Cys Glu Arg Met Pro His Ser
1               5                   10                  15

<210> SEQ ID NO 242
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 242

Thr Trp Val Gln Cys Thr Met Val Cys Tyr Gly Met Ser Thr Thr
1               5                   10                  15

<210> SEQ ID NO 243
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 243

Gln Val Lys Leu His Pro Met Ala Pro Val Val Pro Ser His Trp
1               5                   10                  15

<210> SEQ ID NO 244
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 244
```

```
Ala Asp Thr Ile Cys Trp Tyr Val Cys Thr Ile Ser Val His Ala
1               5                   10                  15
```

<210> SEQ ID NO 245
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 245

```
Ile Met Met Glu Cys Phe Tyr Val Cys Thr Ile Ala Asn Thr Gln
1               5                   10                  15
```

<210> SEQ ID NO 246
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 246

```
Thr Thr Cys Lys Tyr Tyr Leu Ser Cys Arg Trp Arg Lys Asp Leu
1               5                   10                  15
```

<210> SEQ ID NO 247
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 247

```
Tyr Pro Pro Arg Phe Gln Tyr Tyr Arg Phe Tyr Tyr Arg Gly Pro
1               5                   10                  15
```

<210> SEQ ID NO 248
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 248

```
Thr Asp Phe Leu Ser Tyr Tyr Arg Val Tyr Arg Thr Pro Leu Gln
1               5                   10                  15
```

<210> SEQ ID NO 249
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 249

```
Thr Phe Met Pro Ser Tyr Tyr Arg Ser Trp Gly Pro Pro Pro Thr
1               5                   10                  15
```

<210> SEQ ID NO 250
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 250

```
Arg Tyr Ile Met Asn His Arg Gly Phe Tyr Ile Phe Val Pro Arg
```

```
<210> SEQ ID NO 251
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 251

Leu Met Asn Trp Arg Gly Phe Met Val Pro Arg Glu Ser Pro Lys
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 252

Pro Tyr Leu Asn Ala Arg Gly Phe Ser Val Thr Arg Glu Gln Ile
1               5                   10                  15

<210> SEQ ID NO 253
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 253

Met Ile Phe Asn Ser Arg Gly Phe Leu Ser Leu Met Ser Ser Gly
1               5                   10                  15

<210> SEQ ID NO 254
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 254

Trp Thr Lys Leu Lys Asn Ser Arg Gly Phe Glu Leu Gln Leu Asp
1               5                   10                  15

<210> SEQ ID NO 255
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 255

Glu Trp Ala Cys Asn Asp Arg Gly Phe Asn Cys Gln Leu Gln Arg
1               5                   10                  15

<210> SEQ ID NO 256
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 256

Phe Pro Ile Tyr Asn Gln Arg Gly Phe Ile Thr Leu Ala Ser Pro
1               5                   10                  15
```

```
<210> SEQ ID NO 257
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 257

Ile Cys Val Asn Ile Lys Lys Ser Leu Trp Ala Cys Glu Ile Arg
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 258

Asn Cys Val Arg Ile Leu Met Thr Phe Leu Asp Cys Thr Ile Asp
1               5                   10                  15

<210> SEQ ID NO 259
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 259

Gly Cys Leu Gln Ile Leu Pro Thr Leu Ser Glu Cys Phe Gly Arg
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 260

Val Cys Arg Leu Met Arg Gly Arg Cys Leu Leu Tyr Ser Val Phe
1               5                   10                  15

<210> SEQ ID NO 261
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 261

Thr Cys Val Leu His Arg Gln Arg Cys Leu Met Phe Thr Leu Arg
1               5                   10                  15

<210> SEQ ID NO 262
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 262

Lys Gln Arg Gly Ala Thr Met Val Leu Arg Thr Tyr Thr Leu Arg
1               5                   10                  15
```

<210> SEQ ID NO 263
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 263

Tyr Glu Arg Arg Pro Thr Leu Val Leu Arg Thr Trp Arg Pro Trp
1               5                   10                  15

<210> SEQ ID NO 264
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 264

Tyr Cys Leu Ser Tyr Ser Asn Gly Arg Phe Phe His Cys Pro Ala
1               5                   10                  15

<210> SEQ ID NO 265
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 265

Arg Val Trp Trp Trp Met Ser Gly Arg Trp Arg Leu Ala Tyr Gln
1               5                   10                  15

<210> SEQ ID NO 266
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 266

Glu Ser Gly Phe Arg Leu Leu Ala Tyr Pro Gln Ser Leu Val Ser
1               5                   10                  15

<210> SEQ ID NO 267
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 267

Tyr Cys Cys His Pro Gln Val Cys Phe Leu Gly His Arg Ala Ala Cys
1               5                   10                  15

Pro

<210> SEQ ID NO 268
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 268

Trp Cys Cys His Pro Gln Val Cys Ser Leu Ser Leu Ala Tyr Lys Cys
1               5                   10                  15

Gln

<210> SEQ ID NO 269
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 269

Ile Cys Cys His Pro Gln Val Cys Ala Trp Asn Arg Val Phe Leu Cys
1               5                   10                  15

Lys

<210> SEQ ID NO 270
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 270

Ile Cys Cys His Pro Gln Val Cys Ser Gly Leu Asn Arg Phe Arg Cys
1               5                   10                  15

Gly

<210> SEQ ID NO 271
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 271

Trp Cys Cys His Pro Gln Val Cys His Arg Ala Met Val Arg Asn Cys
1               5                   10                  15

Ile

<210> SEQ ID NO 272
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 272

Ala Cys Cys His Pro Gln Val Cys Val Met Ala Leu Pro Tyr His Cys
1               5                   10                  15

Leu

<210> SEQ ID NO 273
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 273

Leu Cys Cys His Pro Gln Val Cys Ala Ser Ala Gly Tyr Tyr Ala Cys
1               5                   10                  15

Tyr

```
<210> SEQ ID NO 274
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 274

Leu Cys Cys His Pro Gln Asn Cys Val Ser Phe Arg His Val Glu Cys
1               5                   10                  15
Arg

<210> SEQ ID NO 275
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 275

Ile Cys Cys His Pro Gln Trp Cys Gly Leu Thr Val Trp Trp Pro Cys
1               5                   10                  15
Lys

<210> SEQ ID NO 276
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 276

Gln Ser Leu Val Cys Gln Asn Val Cys Trp Met Arg Glu
1               5                   10

<210> SEQ ID NO 277
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 277

Cys Met Ile Ile Cys Gln Asn Val Cys Tyr Arg Lys Cys
1               5                   10

<210> SEQ ID NO 278
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 278

Lys Ala Leu Val Cys Gln Asn Val Cys Tyr Thr Met Ser
1               5                   10

<210> SEQ ID NO 279
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 279

Ser Lys Trp Ile Cys Gln Asn Val Cys Tyr Pro Gly Leu
```

```
1               5                   10
```

<210> SEQ ID NO 280
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 280

```
Gly Thr Leu Val Cys Met Asn Phe Cys Tyr Leu Ser Lys
1               5                   10
```

<210> SEQ ID NO 281
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 281

```
Pro Thr Leu Ile Cys Met Asn Val Cys Phe Tyr Asp Gln
1               5                   10
```

<210> SEQ ID NO 282
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 282

```
Ser His Trp Phe Cys Val Asn Val Cys Phe Arg Ile Gln
1               5                   10
```

<210> SEQ ID NO 283
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 283

```
Thr Tyr Ser Trp Cys Ala Asn Val Cys Met His Tyr Ser
1               5                   10
```

<210> SEQ ID NO 284
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 284

```
Thr Arg Leu Ile Cys Ala Asn Leu Cys Trp Tyr Ala Glu
1               5                   10
```

<210> SEQ ID NO 285
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 285

```
Gln Ala Gly Leu Thr Trp Tyr Trp Trp Tyr Ser Cys Arg Gln Ile
1               5                   10                  15
```

<210> SEQ ID NO 286
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 286

Met Asn Tyr Trp Ile Tyr Phe Cys Gly Val Trp Met Gln Ala His
1               5                   10                  15

<210> SEQ ID NO 287
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 287

Ser Tyr Trp Val Tyr His Cys Tyr Tyr Gly Trp Tyr Ser Gln Trp
1               5                   10                  15

<210> SEQ ID NO 288
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 288

Cys Trp Tyr Gln Trp Cys Gly Tyr Tyr Ser Tyr Asn Cys His
1               5                   10                  15

<210> SEQ ID NO 289
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 289

Gln Thr Ala Thr Val Ser Tyr Trp Cys Tyr Trp Trp Trp Lys Val
1               5                   10                  15

<210> SEQ ID NO 290
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 290

His Pro Lys Ser Pro Tyr Arg Tyr Trp Asp Trp Thr Ala His Arg Tyr
1               5                   10                  15

Tyr Ser Tyr Gln Leu Cys Asn Leu Ser Ser
            20                  25

<210> SEQ ID NO 291
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 291

Met Val Trp Thr Lys Trp Ser Trp Cys Ala Phe Tyr Arg Arg Ile
1               5                   10                  15

<210> SEQ ID NO 292
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 292

Gln Glu Trp Arg Gln Leu Thr Arg Trp Cys Trp Val Gln Ile Lys
1               5                   10                  15

<210> SEQ ID NO 293
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 293

Pro Trp Cys Trp Met Trp Thr Lys Gly Arg Trp Tyr Tyr Val Ala
1               5                   10                  15

<210> SEQ ID NO 294
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 294

Thr Trp Thr Trp Cys Trp Arg Asn Tyr Trp Ile Gln Leu Ser Thr
1               5                   10                  15

<210> SEQ ID NO 295
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 295

Trp Val Ala Gly Tyr Trp Trp Cys Trp Ser Val Met Tyr Arg Ser
1               5                   10                  15

<210> SEQ ID NO 296
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 296

Gly Asp Thr Trp Val Trp Tyr Cys Trp Tyr Trp Thr Arg Ser Ile
1               5                   10                  15

<210> SEQ ID NO 297
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 297

Trp Val Cys Thr Trp Asn Tyr Trp Thr Arg Val Thr Trp Cys Leu

<210> SEQ ID NO 298
<211> LENGTH: 40
<212> TYPE: DNA
<213> ORGANISM: Artificial Sequence
<220> FEATURE:
<223> OTHER INFORMATION: Synthetic Primer

<400> SEQUENCE: 298
ttcgagctcg gtacctttga ggtggttatg aaaaaaattg                     40

<210> SEQ ID NO 299
<211> LENGTH: 60
<212> TYPE: DNA
<213> ORGANISM: Artificial Sequence
<220> FEATURE:
<223> OTHER INFORMATION: Synthetic Primer

<400> SEQUENCE: 299
ctggcctcca cccatctgct ggccgccggt catgctcgcc atagtagaag tcgcagctac    60

<210> SEQ ID NO 300
<211> LENGTH: 60
<212> TYPE: DNA
<213> ORGANISM: Artificial Sequence
<220> FEATURE:
<223> OTHER INFORMATION: Synthetic Primer

<400> SEQUENCE: 300
ggccagcaga tgggtggagg ccagtctggc cagtctggtg actacaacaa aaaccagtac    60

<210> SEQ ID NO 301
<211> LENGTH: 45
<212> TYPE: DNA
<213> ORGANISM: Artificial Sequence
<220> FEATURE:
<223> OTHER INFORMATION: Synthetic Primer

<400> SEQUENCE: 301
cagtagaagt cgctccgctt cctccgaagc ggtaaccaac accgg               45

<210> SEQ ID NO 302
<211> LENGTH: 45
<212> TYPE: DNA
<213> ORGANISM: Artificial Sequence
<220> FEATURE:
<223> OTHER INFORMATION: Synthetic Primer

<400> SEQUENCE: 302
ggaggaagcg gagcgacttc tactgtaact ggcggttacg cacag               45

<210> SEQ ID NO 303
<211> LENGTH: 56
<212> TYPE: DNA
<213> ORGANISM: Artificial Sequence
<220> FEATURE:
<223> OTHER INFORMATION: Synthetic Primer

<400> SEQUENCE: 303
aaaacagcca agcttggcca ccttggcctt attagcttgc agtacggctt ttctcg        56

<210> SEQ ID NO 304
<211> LENGTH: 40
<212> TYPE: DNA
<213> ORGANISM: Artificial Sequence

```
<220> FEATURE:
<223> OTHER INFORMATION: Synthetic Primer

<400> SEQUENCE: 304
ttcgagctcg gtacctttga ggtggttatg aaaaaaattg                              40

<210> SEQ ID NO 305
<211> LENGTH: 60
<212> TYPE: DNA
<213> ORGANISM: Artificial Sequence
<220> FEATURE:
<223> OTHER INFORMATION: Synthetic Primer

<400> SEQUENCE: 305
ctggcctcca cccatctgct ggccgccggt catgctcgcc atagtagaag tcgcagctac        60

<210> SEQ ID NO 306
<211> LENGTH: 59
<212> TYPE: DNA
<213> ORGANISM: Artificial Sequence
<220> FEATURE:
<223> OTHER INFORMATION: Synthetic Primer

<400> SEQUENCE: 306
gccagcagat gggtggaggc cagtctggcc agtctggtga ctacaacaaa aaccagtac        59

<210> SEQ ID NO 307
<211> LENGTH: 45
<212> TYPE: DNA
<213> ORGANISM: Artificial Sequence
<220> FEATURE:
<223> OTHER INFORMATION: Synthetic Primer

<400> SEQUENCE: 307
cagtagaagt cgctccgctt cctccgaagc ggtaaccaac accgg                        45

<210> SEQ ID NO 308
<211> LENGTH: 45
<212> TYPE: DNA
<213> ORGANISM: Artificial Sequence
<220> FEATURE:
<223> OTHER INFORMATION: Synthetic Primer

<400> SEQUENCE: 308
ggaggaagcg gagcgacttc tactgtaact ggcggttacg cacag                        45

<210> SEQ ID NO 309
<211> LENGTH: 60
<212> TYPE: DNA
<213> ORGANISM: Artificial Sequence
<220> FEATURE:
<223> OTHER INFORMATION: Synthetic Primer

<400> SEQUENCE: 309
tgctggccgc cggtcatgct cgccatctgg ccagactggc ctccgtattc agtggtctgg        60

<210> SEQ ID NO 310
<211> LENGTH: 60
<212> TYPE: DNA
<213> ORGANISM: Artificial Sequence
<220> FEATURE:
<223> OTHER INFORMATION: Synthetic Primer

<400> SEQUENCE: 310
aaaacagcca agcttggcca ccttggcctt attaacccat ctgctggcgc ccggtcatgc        60
```

```
<210> SEQ ID NO 311
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 311

Tyr Cys Leu Ser Tyr Ser Asn Gly Arg Phe Phe His Cys Pro Ala
1               5                   10                  15

<210> SEQ ID NO 312
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 312

Met Ala Ser Met Thr Gly Gly Gln Gln Met Gly
1               5                   10

<210> SEQ ID NO 313
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 313

Tyr His Asp Thr Gly Phe Ile Asn Asn Asn Gly Pro Thr His Glu Asn
1               5                   10                  15

<210> SEQ ID NO 314
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (10)..(10)
<223> OTHER INFORMATION: Xaa=Any Amino Acid
<220> FEATURE:
<221> NAME/KEY: VARIANT
<222> LOCATION: (10)..(10)
<223> OTHER INFORMATION: Xaa can be any number of amino acids

<400> SEQUENCE: 314

Tyr His Asp Thr Gly Leu Ile Gly Gln Xaa Asn Gly Pro Thr His Glu
1               5                   10                  15

Asn

<210> SEQ ID NO 315
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (2)..(2)
<223> OTHER INFORMATION: Xaa= Any Amino Acid

<400> SEQUENCE: 315

Asn Xaa Arg Gly Phe
1               5
```

<210> SEQ ID NO 316
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (2)..(4)
<223> OTHER INFORMATION: Xaa= Any Amino Acid

<400> SEQUENCE: 316

Met Xaa Pro Xaa Gln Gln
1               5

<210> SEQ ID NO 317
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (2)..(2)
<223> OTHER INFORMATION: Xaa= Any Amino Acid

<400> SEQUENCE: 317

Met Xaa Pro Gln Gln
1               5

<210> SEQ ID NO 318
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(1)
<223> OTHER INFORMATION: XAA = any amino acid
<220> FEATURE:
<221> NAME/KEY: VARIANT
<222> LOCATION: (4)..(7)
<223> OTHER INFORMATION: XAA = any amino acid
<220> FEATURE:
<221> NAME/KEY: VARIANT
<222> LOCATION: (9)..(15)
<223> OTHER INFORMATION: XAA = any amino acid
<220> FEATURE:
<221> NAME/KEY: VARIANT
<222> LOCATION: (17)..(17)
<223> OTHER INFORMATION: XAA = any amino acid

<400> SEQUENCE: 318

Xaa Cys Cys Xaa Xaa Xaa Xaa Cys Xaa Xaa Xaa Xaa Xaa Xaa Xaa Cys
1               5                   10                  15

Xaa

<210> SEQ ID NO 319
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(4)
<223> OTHER INFORMATION: XAA = any amino acid
<220> FEATURE:
<221> NAME/KEY: VARIANT
<222> LOCATION: (6)..(8)

```
<223> OTHER INFORMATION: XAA = any amino acid
<220> FEATURE:
<221> NAME/KEY: VARIANT
<222> LOCATION: (10)..(13)
<223> OTHER INFORMATION: XAA = any amino acid

<400> SEQUENCE: 319

Xaa Xaa Xaa Xaa Cys Xaa Xaa Xaa Cys Xaa Xaa Xaa Xaa
1               5                   10

<210> SEQ ID NO 320
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)..(3)
<223> OTHER INFORMATION: XAA = any amino acid

<400> SEQUENCE: 320

Cys Xaa Xaa Val Cys
1               5

<210> SEQ ID NO 321
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)..(4)
<223> OTHER INFORMATION: XAA = any amino acid

<400> SEQUENCE: 321

Cys Xaa Xaa Xaa Cys
1               5
```

POLYPEPTIDE DISPLAY LIBRARIES AND METHODS OF MAKING AND USING THEREOF

CROSS REFERENCE TO RELATED APPLICATIONS

This application is a continuation of U.S. patent application Ser. No. 14/821,580, filed on 7 Aug. 2015, which is a continuation of U.S. patent application Ser. No. 13/722,915, filed on 20 Dec. 2012, now U.S. Pat. No. 9,134,309, which is a continuation of U.S. patent application Ser. No. 12/563,897 filed on 21 Sep. 2009, now U.S. Pat. No. 8,361,933, which is a continuation of U.S. patent application Ser. No. 11/612,757, filed 19 Dec. 2006, now U.S. Pat. No. 7,612,019, which is a divisional of U.S. patent application Ser. No. 10/920,244, filed 18 Aug. 2004, now U.S. Pat. No. 7,256,038, which claims the benefit of U.S. Provisional Patent Application No. 60/495,698, filed 18 Aug. 2003, listing Patrick S. Daugherty, Paul H. Bessette, and Jeffrey Rice, as joint inventors, all of which are herein incorporated by reference in their entirety.

BACKGROUND OF THE INVENTION

1. Field of the Invention

The present invention generally relates to bacterial polypeptide display libraries and methods of making and using thereof.

DESCRIPTION OF THE RELATED ART

Polypeptide display technologies have substantially impacted basic and applied research applications ranging from drug discovery to materials synthesis. See Clackson, T. and J. A. Wells (1994) Trends In Biotech. 12(5):173-184; and Shusta, E. V., et al. (1999) Curr. Opin. Biotechnol. 10(2): 117-122; and Kodadek, T., (2001) Chem. Biol. 8(2): 105-158; Lee, S. W., et al. (2002) Science 296 (5569):892-859; and Nixon, A. E. (2002) Curr. Pharm. Biotechnol. 3(1):1-12. The strength of these methods derives from the ability to generate libraries containing billions of diverse molecules using the biosynthetic machinery of the cell, and subsequently, to identify rare desired polypeptides using selection or high-throughput screening methods. Display libraries have been applied extensively to isolate and engineer peptides and antibodies for molecular recognition applications. In particular, display of peptides on the surface of filamentous bacteriophage, or phage display, has proven a versatile and effective methodology for the isolation of peptide ligands binding to a diverse range of targets. See Scott, J. K. and G. P. Smith (1990) Science 249(4967):386-904; Norris, J. D., et al. (1999) Science 285(5428):744-765; Arap, W., et al. (1998) Science 279(5349):377-806; and Whaley, S. R., et al. (2000) Nature 405(6787):665-668.

Polypeptide display systems include mRNA and ribosome display, eukaryotic virus display, and bacterial and yeast cell surface display. See Wilson, D. S., et al. 2001 PNAS USA 98(7):3750-3511; Muller, O. J., et al. (2003) Nat. Biotechnol. 3:312; Bupp, K. and M. J. Roth (2002) Mol. Ther. 5(3):329-3513; Georgiou, G., et al., (1997) Nat. Biotechnol. 15(1):29-3414; and Boder, E. T. and K. D. Wittrup (1997) Nature Biotech. 15(6):553-557. Surface display methods are attractive since they enable application of fluorescence-activated cell sorting (FACS) for library analysis and screening See Daugherty, P. S., et al. (2000) J. Immunol. Methods 243(1-2):211-2716; Georgiou, G. (2000) Adv. Protein Chem. 55:293-315; Daugherty, P. S., et al. (2000) PNAS USA 97(5):2029-3418; Olsen, M. J., et al. (2003) Methods Mol. Biol. 230:329-342; and Boder, E. T. et al. (2000) PNAS USA 97(20):10701-10705.

Phage display involves the localization of peptides as terminal fusions to the coat proteins, e.g., pIII, pIV of bacteriophage particles. See Scott, J. K. and G. P. Smith (1990) Science 249(4967):386-390; and Lowman, H. B., et al. (1991) Biochem. 30(45):10832-10838. Generally, polypeptides with a specific function of binding are isolated by incubating with a target, washing away non-binding phage, eluting the bound phage, and then re-amplifying the phage population by infecting a fresh culture of bacteria. Unfortunately, phage display presents a few undesirable properties. See Zahn, G. (1999) Protein Eng. 12(12): 1031-1034. For example, phage display is limited to about a few thousand copies of the displayed polypeptide per phage or less, thereby precluding the use of sensitive fluorescence-activated cell sorting (FACS) methodologies for isolating the desired sequences. Phage are also difficult to elute or recover from an immobilized target ligand, thereby resulting in clonal loss. Phage display also requires an infection step wherein viruses that do not bind and enter a cell are lost early in the process, thereby resulting in lower quality results overall, e.g., affinity of isolated binding molecules. Further, phage display selections are time consuming requiring typically about two to about three weeks for the isolation of phage display polypeptides that bind a given target.

Most notably, phage display requires that the investigator be familiar with routine phage manipulation methods including infections, phage amplifications, titering, phage ELISA, and others. Second, phage display methods can lead to Darwinian outgrowth of particular clones owing to their relative infectivity, assembly efficiency, and toxicity to the host cell. Third, the rate at which desired binding clones can be enriched is slowed by relatively low enrichment ratios.

Other display formats and methodologies include mRNA display, ribosome or polysome display, eukaryotic virus display, and bacterial, yeast, and mammalian cell surface display. See Matthcakis, L. C., et al. (1994) PNAS USA 91(19): 9022-9026; Wilson, D. S., et al. (2001) PNAS USA 98(7):3750-3755; Shusta, E. V., et al. (1999) Curr. Opin. Biotech. 10(2): 117-122; and Boder, E. T. and K. D. Wittrup (1997) Nature Biotech. 15(6):553-557. A variety of alternative display technologies have been developed and reported for display on the surface of a microorganism and pursued as a general strategy for isolating protein binding peptides without reported successes. See Maurer, J., et al. (1997) J. Bacteriol. 179(3):794-804; Samuelson, P., et al. (1995) J. Bacteriol. 177(6):1470-1476; Robert, A., et al. (1996) FEBS Letters 390(3): 327-333; Stathopoulos, C., et al. (1996) Appl. Microbiol. & Biotech. 45(1-2): 112-119; Georgiou, G., et al., (1996) Protein Engineering 9(2): 239-247; Haddad, D., et al., (1995) FEMS Immunol. & Medical Microbiol. 12(3-4):175-186; Pallesen, L., et al., (1995) Microbiol. 141(Pt 11): 2839-2848, Xu, Z. and S. Y. Lee (1999) Appl. Environ. Microbiol. 65(11):5142-5147; Wernerus, H. and S. Stahl (2002) FEMS Microbiol. Lett. 212(1): 47-54; and Westerlund-Wikstrom, B. (2000) Int. J. Med. Microbiol. 290(3):223-230. Some of these prior art display systems have been tested for library screening without success for isolation of high affinity protein binding peptides. See Brown, S. (1992) PNAS USA 89(18):8651-8655; Lang, H., et al. (2000) Eur. J. Biochem. 267(1):163-170; Klemm, P. and M. A. Schembri (2000) Int. J. Med. Microbiol. 290(3): 215-221; Klemm, P. and M. A. Schembri (2000) Microbiol.

146(Pt 12):3025-3032; Kjaergaard, K., et al. (2000) Appl. Environ. Microbiol. 66(1):10-14; Schembri, M. A., (1999) FEMS Microbiol. Lett. 170(2):363-371; Benhar, I., et al. (2000) J. Mol. Biol. 301(4):893-904; and Lang, H., et al. (2000) Adv. Exp. Med. Biol. 485:133-136.

Prior art expression vectors for polypeptide display libraries using host cells suffer from a variety of problems. The problems of the prior art methods include (1) only small peptides may be expressed, (2) large libraries cannot be selected, (3) the polypeptides are not expressed on the outer membrane surface, but are instead expressed in the periplasmic space between the inner and the outer membranes, (4) polypeptides that are displayed on the outer membrane surface do not properly bind or interact with large molecules and certain targets, and (5) analyzing expression on fimbrial or flagella results in loss of some desired polypeptides due to mechanical shearing.

Protein display on the surface of bacterial cells holds the potential to simplify and accelerate the process of ligand isolation since experimental procedures with bacteria are efficient and screening can be performed using FACS. See Daugherty, P. S., et al. (2000) J. Immunol. Methods 243(1-2):211-2720; Brown, S. (1992) PNAS USA 89(8):8651-8521; and Francisco, J. A., et al. (1993) PNAS USA 90(22):10444-10448; Taschner, S., et al. (2002) Biochem. J. 367(Pt 2):393-402; Etz, H., et al. (2001) J. Bacteriol. 183(23):6924-6935; and Camaj, P., et al. (2001) Biol. Chem. 382(12):1669-1677. Though several different bacterial display systems have been reported, their usefulness has been restricted by technical limitations including accessibility on the cell surface, inability to display highly diverse sequences, and adverse effects on cell growth and viability. See Francisco, J. A., et al. (1993) PNAS USA 90(22):10444-10822; Lu, Z., et al. (1995) Biotechnology (NY) 13(4):366-7223; Klemm, P. and M. A. Schembri, (2000) Microbiology 146(Pt 12):3025-3224; Christmann, A., et al. (1999) Protein Eng. 12(9):797-80625; Lee, S. Y., et al. (2003) Trends Biotechnol. 21(1):45-52; Lu, Z., et al. (1995) Biotechnology (NY) 13(4):366-7225; Lee, S. Y., et al. (2003) Trends Biotechnol. 21(1):45-5226; Camaj, P., et al. (2001) Biol. Chem. 382(12):1669-1677; and Schembri, M. A., et al. (2000) Infect. Immun. 68(5):2638-2646.

Consequently, these techniques do not enable isolation of high affinity peptide ligands. Additionally, these techniques do not provide peptide exposure on the cell surface suitable for binding to analytes including antibodies, proteins, viruses, cells, macromolecules. Thus, these display formats are not compatible with certain isolation methods, since the peptides produced do not bind to large molecules and other surfaces, e.g., magnetic particles. The prior art process also reduces cell viability and alters membrane permeability, thereby reducing process efficiency. Thus far, routine isolation of high affinity peptide ligands for arbitrary protein targets has not been demonstrated. See Camaj, P., et al., (2001) Biol. Chem. 382(12):1669-7727; and Tripp, B. C., et al., (2001) Protein Eng. 14(5):367-377; Lang, H., et al. (2000) Eur. J. Biochem. 267(1):163-170; Lang, H., et al. (2000) Adv. Exp. Med. Biol. 485:133-136; Klemm, P. and M. A. Schembri (2000) Int. J. Med. Microbiol. 290(3):215-221; Klemm, P. and M. A. Schembri (2000) Microbiol. 146(Pt 12):3025-302; Kjaergaard, K., et al. (2000) Appl. Environ. Microbiol. 66(1):10-14; Schembri, M. A., et al. (1999) FEMS Microbiol. Lett. 170(2):363-371; Benhar, I., et al. (2000) Mol. Biol. 301(4):893-904; Kjaergaard, K., et al. (2001) Appl. Environ. Microbiol. 67(12):5467-5473; and Lang, H., et al. (2000) Exp. Med. Biol. 485:133-136.

Also, polypeptides in the prior art are most often displayed on cell surfaces either as insertional fusions or "sandwich fusions" into outer membrane or extracellular appendage, e.g., fimbria, flagella proteins, or less frequently, as fusions to truncated or hybrid proteins thought to be localized on the cell surface. See Pallesen, L., et al. (1995) Microbiol. 141(Pt 11):2839-48; and Etz, H., et al. (2001) J. Bacteriol. 183(23):6924-6935. Examples of the latter include the LppOmpA system and the ice nucleation protein (InP). See Georgiou, G., et al. (1997) Nat. Biotechnol. 15(1):29-34. The outer membrane proteins OmpA, OmpC, OmpF, FhuA, and LamB, have enabled the display of polypeptides as relative short insertional fusions into OMP loops exposed on the extracellular side of the outer membrane. See Xu, Z. and S. Y. Lee (1999) Appl. Environ. Microbiol. 65(11):5142-5147; Taschner, S., et al. (2002) Biochem. J. 367(Pt 2):393-402.

However, the C and N-termini of these "carrier" proteins are not naturally located on the cell surface which precludes the ability to display polypeptides as terminal fusions. As a result, proteins which are not capable of folding in the insertional fusion context, when their C and N termini are fused to the "carrier" protein sequence, as well as those for which the C and N termini are physically separated in space, e.g., single chain Fv antibody fragments, cannot be displayed effectively as insertions. Similarly, the restriction to the use of insertional fusions, interferes with the display of a large number of proteins encoded by cDNA libraries on the cell surface.

Prior art methods have attempted to address the problems of insertional fusion displays by truncating outer membrane protein sequences such that the resulting new termini might be displayed on the cell surface. See Lee, et al. (2003) Trends in Biotech. 23(1):45-52; Georgiou, et al. (1997) Nat. Biotech. 15(1):29-34. These prior art approaches were used to create the LppOmpA system which allows for the targeting of peptides and polypeptides to the outer membrane of bacteria. See Francisco, et al. (1992) PNAS USA 89(7):2913. For example, expression vectors for which use LppOmpA', araBAD promoter, chloramphenicol resistance, and a p15A origin (LppOmpA expression vector). See Daugherty et al. (1999) Protein Engineer. 12(7):613-621. The LppOmpA expression vector encodes a fusion protein that results in a truncation of the OmpA protein at amino acid residue 159. Unfortunately, the performance of LppOmpA expression vector as a general process for isolating and expressing polypeptides from large libraries is significantly restricted by i) the reduced structural stability of the modified OmpA protein, ii) intolerance to expression at high temperatures, iii) reduced viability, and iv) most importantly, its inability to display polypeptides on the cell surface in a manner compatible with binding to large proteins without compromising viability and/or growth rate See Christman, A. et al., 1999. Prot. Eng. 12 (9):797.

In addition, expression vectors in the prior art are problematic because (1) the polypeptides produced by the expression vectors are not capable of binding externally added proteins, cells, or surfaces to the host cells, (2) the expression vectors does not allow surface presentation of large polypeptides, and (3) the expressed polypeptides are only expressed in the periplasmic region (between the inner and outer membrane) and not on the outer surface of the host cell, and therefore any expressed protein can only interact with small molecules that pass through the outer membrane and into the periplasmic space. These problems have prevented the application of this technology as a general process for isolating high affinity binding polypeptides. See e.g., Stathopoulos, C. (1996) Applied Microbiol. Biotech. 45 (1-2) 112. Earhart C F. (2000) Methods Enzymol. (326): 506-16; Francisco, J. (1994) Annal. NY Acad. Sci. 745:372; and Bessette, P. H., et al. (2004) Prot. Eng. (In Press).

Thus, a need exists for a more robust display methodology which requires minimal technical expertise, is less labor intensive, and speeds the process of ligand isolation from weeks to days as compared to the prior art methods.

SUMMARY OF THE INVENTION

The present invention relates to expression vectors for displaying polypeptides on an outer surface of a biological entity within a carrier protein loop.

In some embodiments, the present invention provides an expression vector capable of expressing and displaying a given passenger polypeptide on an outer surface of a biological entity within a carrier protein loop that is capable of interacting with a given ligand.

In some embodiments, the carrier protein loop is opened resulting in an N-terminus exposed on the outer surface, a C-terminus exposed on the outer surface, or both. In some embodiments, the native C-terminus and the native N-terminus are fused together via a peptide linker. In some embodiments, the N-terminus and the C-terminus exposed to the outer surface are accessible by the ligand. In some embodiments, the C terminus of the passenger polypeptide is fused to the N terminus of the carrier protein. In some embodiments, the N terminus of the passenger polypeptide is fused to the C terminus of the carrier protein. In some preferred embodiments, the carrier protein is OmpX.

In some embodiments, the carrier protein is a bacterial outer membrane protein. In some preferred embodiments, the bacterial outer membrane protein is OmpA or OmpX. In some preferred embodiments, the polypeptide is expressed in the first extracellular loop of OmpA. In some preferred embodiments, the polypeptide is expressed in the second extracellular loop of OmpX. In some preferred embodiments, the polypeptide is expressed in the third extracellular loop of OmpX.

In some embodiments, the polypeptide is streptavidin or a T7 binding peptide.

In some embodiments, the biological entity is a bacterial cell, a yeast cell or a mammalian cell. In some preferred embodiments, the biological entity is a bacterial cell. In some preferred embodiments, the bacterial cell is *Escherichia coli, Shigella sonnei, Shigella dysenteriae, Shingella flexneri, Salmonella typhimurium, Salmonella enterica, Enterobacter aerogenes, Serratia marcescens, Yersinia pestis,* or *Klebsiella pneumoniae.*

In some embodiments, the expression vector further comprises a low copy origin of replication, such as a p15A origin of replication.

In some embodiments, the expression vector further comprises a bacteriocidal antibiotic resistance protein encoding gene. In some embodiments, the bacteriocidal antibiotic resistance protein encoding gene encodes chloramphenicol acetyltransferase.

In some embodiments, the expression vector further comprises at least one SfiI endonuclease restriction enzyme site.

In some embodiments, the expression vector further comprises an arabinose araBAD *E. coli* operon promoter. In some embodiments, expression is induced with the addition of L-arabinose and stopped by the removal of arabinose and the addition of glucose.

In some embodiments, the present invention provides a host cell which comprises an expression vector as provided herein.

In some embodiments, the present invention provides a method of making a polypeptide display library which comprises creating a plurality of expression vectors capable of expressing a plurality of polypeptides according to that described herein and inducing expression.

In some embodiments, the present invention provides a polypeptide expressed on the outer surface of a biological entity by inducing expression of an expression vector described herein. In some embodiments, the polypeptide is expressed in the first extracellular loop of OmpA. In some embodiments, the polypeptide is expressed in the second extracellular loop of OmpX. In some embodiments, the polypeptide is expressed in the third extracellular loop of OmpX.

In some embodiments, the present invention provides a polypeptide expressed on the outer surface of a biological entity by inducing expression of an expression vector having a carrier protein loop opened and an N-terminus exposed on the outer surface, a C-terminus exposed on the outer surface, or both exposed to the outer surface, as described herein. In some embodiments, the polypeptide is expressed in OmpX.

In some embodiments, the present invention provides a polypeptide display library which comprises a polypeptide expressed and displayed by an expression vector described herein.

In some embodiments, the present invention provides an assay method for detecting, monitoring, or measuring a given ligand in a sample which comprises inducing an expression vector described herein to express the polypeptide and then contacting the polypeptide with the sample and observing whether the polypeptide interacts with the ligand.

In some embodiments, the carrier polypeptide of the expression vector of the present invention is encoded by a nucleic acid molecule which comprises at least one codon that encodes a given amino acid that is replaced with a replacement codon which encodes an alternate amino acid that is structurally similar to the given amino acid. In some embodiments, all the codons that encode the given amino acid are replaced. In some embodiments, the biological entity incorporates at least one non-canonical amino acid analog into the displayed polypeptide. In some embodiments, the given amino acid is leucine. In some embodiments, the alternate amino acid is valine, isoleucine, or trifluorleucine.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

This invention is further understood by reference to the drawings wherein:

FIG. 19 shows CRP binding peptides possessing two distinct consensus sequences. The sequence identifiers from top to bottom are SEQ ID NOs:246-256.

FIG. 20 shows peptide sequences isolated from a 15-mer library in OmpA binding to ZR-75-1 human breast cancer tumor cells. The sequence identifiers from top to bottom are SEQ ID NOs:257-266.

FIG. 26 shows HIV-1 gp120 binding peptides isolated using two cycles of MACS, and one cycle of FACS. The sequence identifiers from top to bottom are SEQ ID NOs: 285-297.

FIG. 27 shows the order and genetic elements required for C-terminal display of the T7 peptide epitope in Loop 2 of OmpX T7 beginning with residue 97 and ending with 95 (P96 deleted). The linker sequence shown is SEQ ID NO:78.

In FIG. 28, the oligonucleotide primers represented by #1, #2, #4, and #5 are as follows:

Primer (5'->3') 1:
Length 60 Melting Tm 48 Sense strand
(SEQ ID NO: 131)
ttcgagctcggtacctttgaggtggttatgaaaaaaattgcatgtctttc agcactggcc Primer (5'->3') 2:
Length 60 Melting Tm 49 Sense strand
(SEQ ID NO: 132)
tttcagcagtggccgcagttctggctttcaccgcaggtacttccgtagct atggcgagca Primer (5'->3') 4:
Length 60 Melting Tm 50 Sense strand
(SEQ ID NO: 134)
cggaggatctggtgactacaacaaaaaccagtactacggcatcactgctg gtccggctta Primer (5'->3') 5:
Length 60 Melting Tm 49 Sense strand
(SEQ ID NO: 135)
gctggtccggcttaccgcattaacgactgggcaagcatctacggtgtagt gggtgtgggt

Primer 1 = Sense
(SEQ ID NO: 298)
ttcgagctcggtacctttgaggtggttatgaaaaaaattg (PD515)

Figure 31:
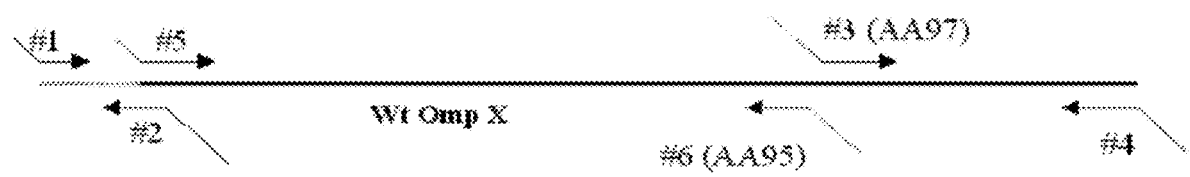
Figure 30:
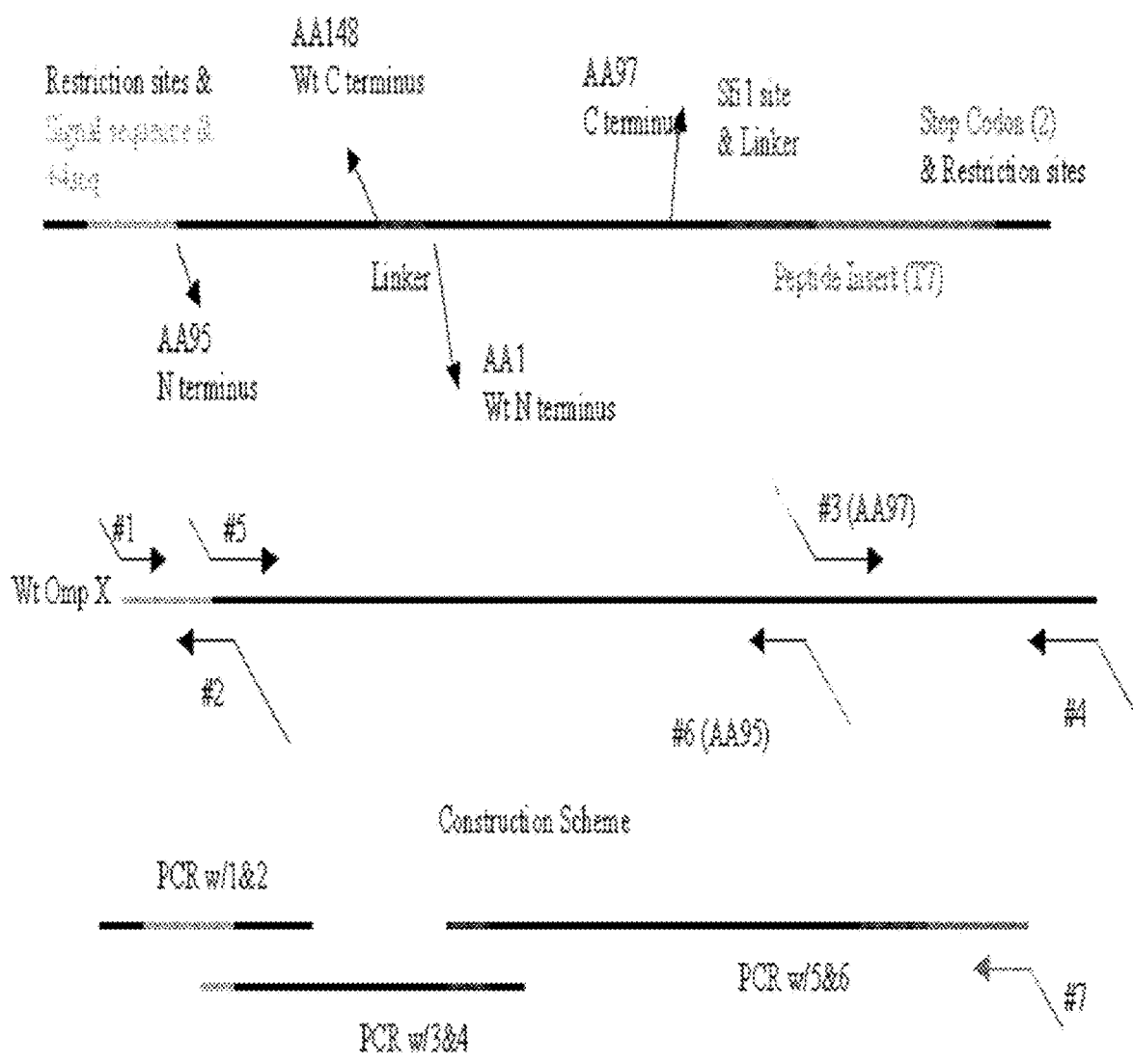

Primer 2 = Anti-Sense
(SEQ ID NO: 299)
ctggcctccacccatctgctggccgccggtcatgctcgccatagtagaag tcgcagctac Primer 3 = Sense
(SEQ ID NO: 300)
ggccagcagatgggtggaggccagtctggccagtctggtgactacaacaa aaaccagtac Primer 4 = Anti-Sense
(SEQ ID NO: 301)
cagtagaagtcgctccgcttcctccgaagcggtaaccaacaccgg Primer 5 = Sense
(SEQ ID NO: 302)
ggaggaagcggagcgacttctactgtaactggcggttacgcacag Primer 6 =
(SEQ ID NO: 303)
aaaacagccaagcttggccaccttggccttattagcttgcagtacggctt ttctcg FIG. 30 shows the arrangement of OmpX fragments needed to enable C-terminal display of a passenger polypeptide. Oligonucleotide primers needed to amplify and assemble the OmpX fragments resulting in C-terminal display are pictorially represented along with the resulting DNA products from application of the polymerase chain reaction. In FIG. 30, the oligonucleotide primers represented by #1, #2, #4, and #5 are defined as follows:

Primer (5'->3') 1:
Length 45 Melting Tm 49 Sense strand:
(SEQ ID NO: 154)
ttcgagctcggtacctttgaggtggttatgaaaaaaattgcatgt Primer (5'->3') 2:
Length 57 Melting Tm 48 Antisense strand:
(SEQ ID NO: 155)
gcggtgaaagccagaactgcggccagtgctgaaagacatgcaattttttt cataacc Primer (5'->3') 4:
Length 57 Melting Tm 49 Antisense strand:
(SEQ ID NO: 157)
ttttccatcgggttgaactgcagacccgcaccgtaggagaaaccgtagtc gctggtg Primer (5'->3') 5:
Length 57 Melting Tm 48 Sense strand:
(SEQ ID NO: 158)
ttcaacccgatggaaaacgttgctctggacttctcttacgagcagagccg tattcgt FIG. 31 shows the annealing locations of oligonucleotide primers that can be used to construct, via overlap PCR, a C-terminal display vector using OmpX. The primers are:

Primer 1 = Sense
(SEQ ID NO: 304)
ttcgagctcggtacctttgaggtggttatgaaaaaaattg (PD515);

Primer 2 = Anti-Sense
(SEQ ID NO: 305)
ctggcctccacccatctgctcggccgccggtcatgctcgccatagtagaa gtcgcagctac;

Primer 3 = Sense
(SEQ ID NO: 306)
gccagcagatgggtggaggccagtctggccagtctggtgactacaacaaa aaccagtac;

Primer 4 = Anti-Sense
(SEQ ID NO: 307)
cagtagaagtcgctccgcttcctccgaagcggtaaccaacaccgg;

Primer 5 = Sense
(SEQ ID NO: 308)
ggaggaagcggagcgacttctactgtaactggcggttacgcacag;

Primer 6 = Anti-Sense
(SEQ ID NO: 309)
tgctggccgccggtcatgctcgccatctggccagactggcctccgtattc agtggtctgg.

Figure 28:
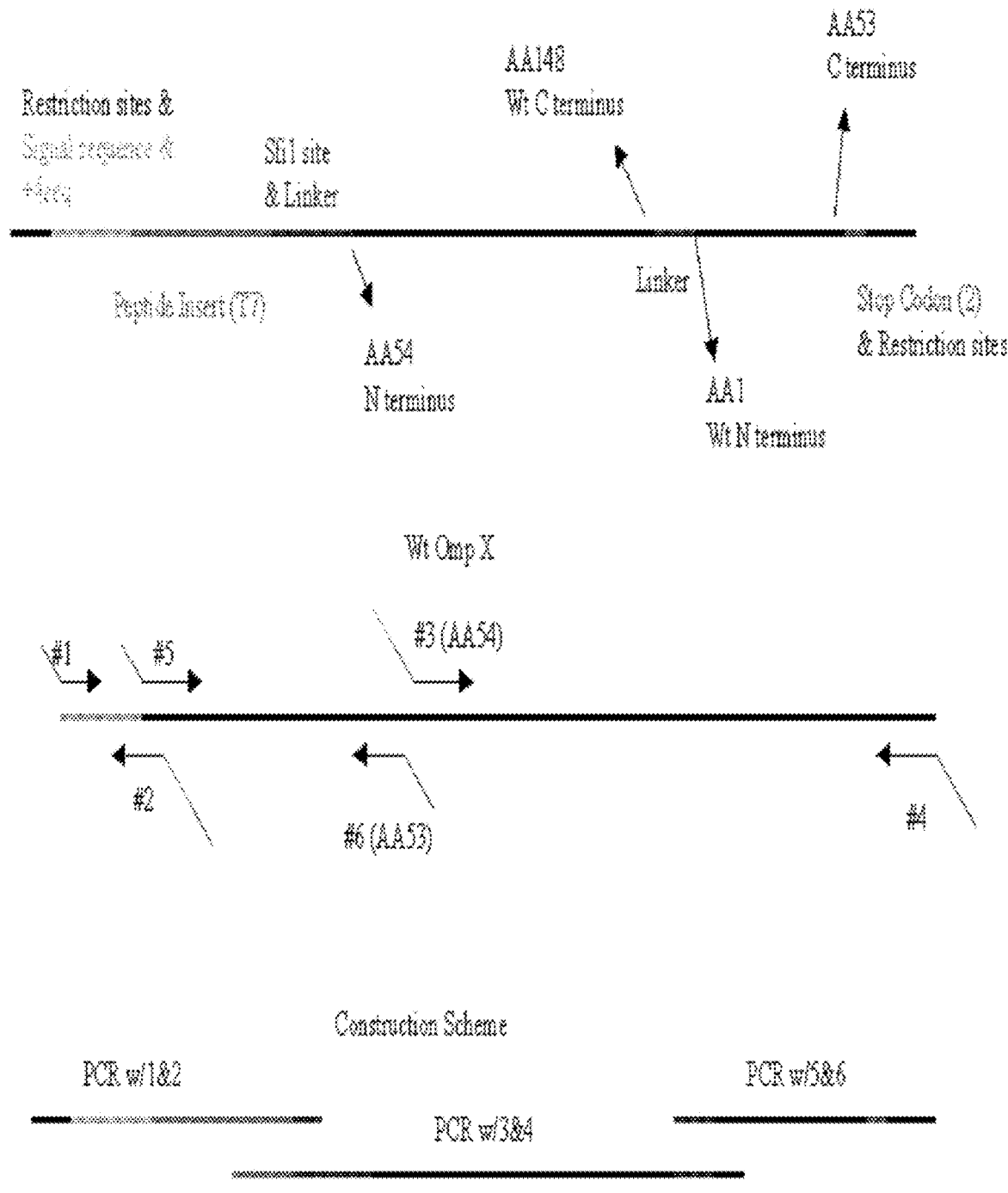
FIG. 28 shows an example methodology for construction of N-terminal fusion display using circular permutation, and loop opening between OmpX residues 53/54. The displayed polypeptide is fused to residue 95, and the leader peptide is genetically fused upstream to aa 97.
Figure 32:
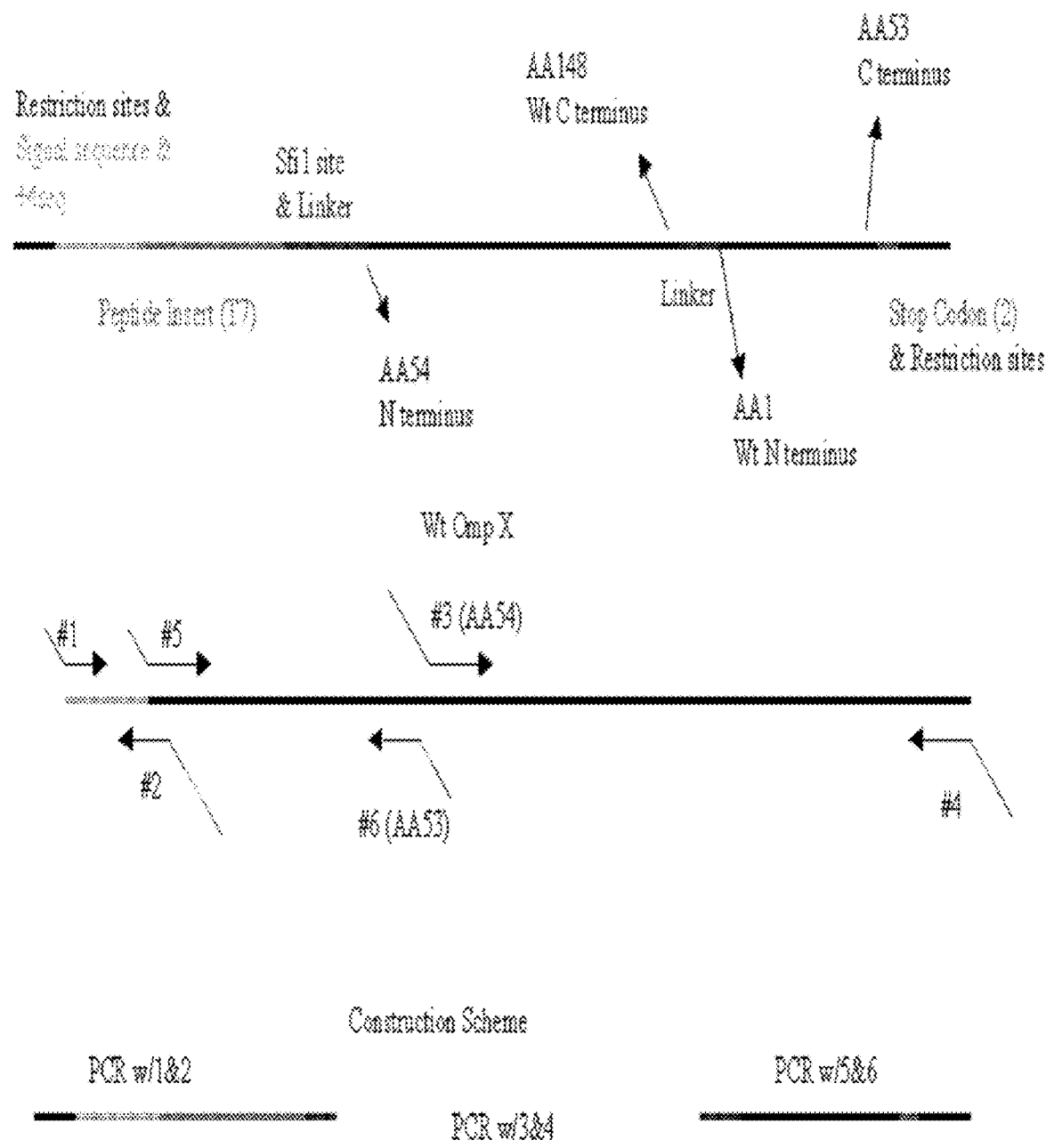

FIG. 32 is substantively duplicate of FIG. 28 and the primers are the same as in FIG. 28.

Figure 33:
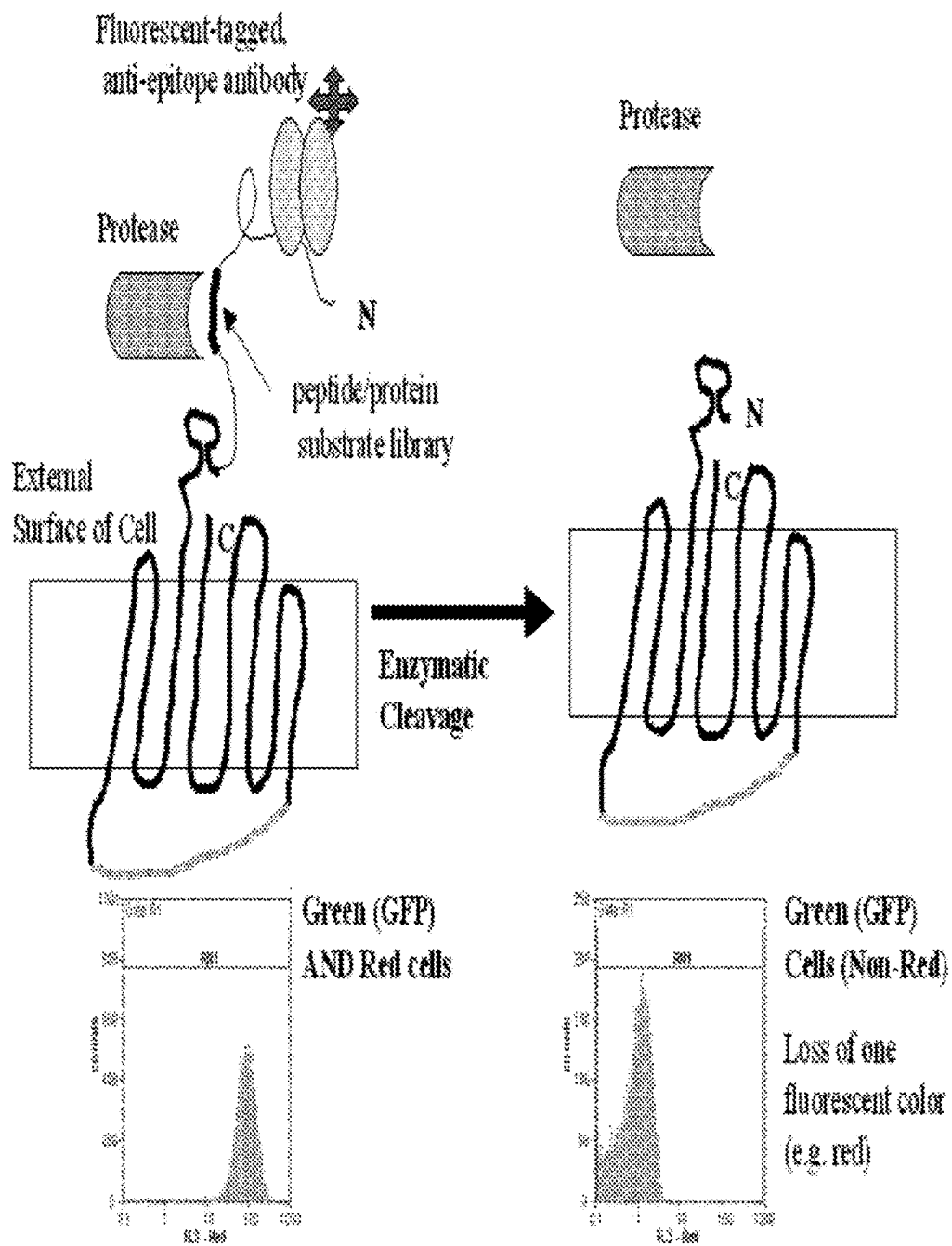

FIG. 33 shows the display of polypeptide enzyme substrates using an N-terminal fusion display vector (N-CPX) for the selection, identification, and engineering of enzyme protease and peptide substrates, displaying the substrate and internally expressing a green fluorescent protein are green and red fluorescent. Cells treated with a given protease which cleaves the surface substrate lose red fluorescence but remain green fluorescent. Isolation of fluorescent green (not red) cells allows the identification of substrates that can be cleaved or lysed by a given protease.

FIG. 34 shows flow cytometric analysis of cells displaying of peptides in an Omp encoding gene modified to possess no leucine codons, thus enabling display of peptides that incorporate a variety of synthetic leucine analogs. Display of a non-canonical amino acid is exemplified using trifluoroleucine (Tfl) and OmpX. This figure also shows a comparison of the level of display of the T7tag peptide (that does not contain any leucine residues) using either unmodified wild-type (top) or NoLeu-OmpX (bottom) scaffolds in the presence of (left) 19 amino acids (deficient in Leu), (middle) 19 amino acids+trifluoroleucine (No Leu), or (right) 20 standard amino acids. These were labeled with an anti-T7tag biotinylated antibody, washed once in PBS, and labeled with streptavidin-phycoerythrin (Molecular Probes, Eugene, Oreg.). The increase in green fluorescence for the 19+Tfl samples (middle) from about 5.6 to about 63.7 allows for the screening of bacterial display libraries for peptides that incorporate Tfl.

DETAILED DESCRIPTION OF THE INVENTION

The present invention provides an expression vector that expresses efficiently on the outer surface of a replicable biological entity a given polypeptide, a "passenger" polypeptide, linked to a surface localized polypeptide, herein referred to as a "carrier" polypeptide, that is otherwise deficient in a surface accessible C or N terminus.

As used herein, a "replicable biological entity" refers to self-replicating biological cells, including bacterial, yeast, protozoal, and mammalian cells, and various viruses capable of infecting these cells known in the art, and the like.

As used herein, the terms "protein", "polypeptide" and "peptide" are used interchangeably to refer to two or more amino acids linked together.

Polypeptides presented according to the present invention (1) alleviate disruption of the energetic structural stability of the carrier polypeptide thus allowing presentation the preferred number of copies of the passenger polypeptide without a loss of viability, (2) are capable of interacting physically with arbitrary compositions of matter (biological or non-biological), and (3) exhibit a biological activity (e.g., affinity, specificity, catalysis, assembly etc.) substantially similar to the corresponding free polypeptide in solution. In other words, the displayed polypeptide interacts with or binds a given target molecule in a manner that is substantially similar to that when the polypeptide is in its native environment and not attached to the biological entity.

As used herein, a "fusion protein" refers to the expression product of two or more nucleic acid molecules that are not natively expressed together as one expression product. For example, a native protein X comprising subunit A and subunit B, which are not natively expressed together as one expression product, is not a fusion protein. However, recombinant DNA methods known in the art may be used to express subunits A and B together as one expression product to yield a fusion protein comprising subunit A fused to subunit B. A fusion protein may comprise amino acid sequences that are heterologous, e.g., not of the same origin, not of the same protein family, not functionally similar, and the like.

The polypeptides expressed and displayed according to the present invention may be large polypeptides yet still retain the ability to bind or interact with given ligands in a manner similar to the native polypeptide or the polypeptide in solution. As provided herein, the expression vectors of the present invention use utilize a low copy origin of replication and a regulatable promoter in order to minimize the metabolic burden of the biological entity and the clonal representation of the polypeptide library is not affected by growth competition during library propagation. The expression vectors of the present invention utilize a antibacterial resistance gene to a bacteriocidal antibiotic which prevents plasmid loss and outgrowth of cells resistant to the antibiotic. Additionally, the expression vectors of the present invention lack a dual system, such as β-lactamase, which results in a smaller expression vector which imposes a smaller burden on cell growth and improves library screening. The expression vectors of the present invention also utilize a SfiI restriction site which allows digestion by a particular enzyme to generate overhangs that cannot react with incorrect DNA substrates.

As used herein, a "ligand" refers to a molecule(s) that binds to another molecule(s), e.g., an antigen binding to an antibody, a hormone or neurotransmitter binding to a receptor, or a substrate or allosteric effector binding to an enzyme and include natural and synthetic biomolecules, such as proteins, polypeptides, peptides, nucleic acid molecules, carbohydrates, sugars, lipids, lipoproteins, small molecules, natural and synthetic organic and inorganic materials, synthetic polymers, and the like.

As used herein, a "receptor" refers to a molecular structure within a cell or on the surface characterized by (1) selective binding of a specific substance and (2) a specific physiologic effect that accompanies the binding, e.g., membrane receptors for peptide hormones, neurotransmitters, antigens, complement fragments, and immunoglobulins and nuclear receptors for steroid hormones and include natural and synthetic biomolecules, such as proteins, polypeptides, peptides, nucleic acid molecules, carbohydrates, sugars, lipids, lipoproteins, small molecules, natural and synthetic organic and inorganic materials, synthetic polymers, and the like.

As used herein, "specifically binds" refers to the character of a receptor which recognizes and interacts with a ligand but does not substantially recognize and interact with other molecules in a sample under given conditions.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids", which comprise naturally-occurring or modified nucleic acid bases attached to a polyamide backbone. Nucleic acids can be either single stranded or double stranded.

An "isolated" nucleic acid molecule or polypeptide refers to a nucleic acid molecule or polypeptide that is in an environment that is different from its native environment in which the nucleic acid molecule or polypeptide naturally occurs. Isolated nucleic acid molecules or polypeptides includes those having nucleotides or amino acids flanking at least one end that is not native to the given nucleic acid molecule or polypeptide. For example, a promoter P for a protein X is inserted at the 5' end of a protein Y which does not natively have P at its 5' end. Protein Y is thus considered to be "isolated".

As provided herein, the expression vectors and libraries of the present invention incorporate (1) the use of a regulatable expression vector that allows on-off control of carrier polypeptide production, (2) efficient restriction sites immediately adjacent to the randomized site to facilitate high-efficiency cloning, (3) random polypeptides inserted into non-conserved sites of carrier polypeptide extracellular loops that efficiently presents a passenger polypeptide to an given ligand, (4) time and temperature-controlled induction periods to obtain optimal display level that result in higher quality results, (5) the use of a bacterial strain having a high plasmid transformation efficiency for transformation, the use of optimized library construction protocols to construct the largest libraries, (6) the use of multiple-plasmid transformation to yield a larger number of unique passenger polypeptides for a given number of host cells, (7) the use of cell concentration to enable complete processing of larger numbers of sequences ($10^{11}$), (8) the use of gene encoding the carrier polypeptide deficient in one or more amino acids, or (9) a combination thereof.

The present invention may be broadly applied to methods to isolate, improve or otherwise alter, peptide and polypeptide sequences that perform useful or desired functions including binding, catalysis, assembly, transport, and the like. For example, the expression vectors of the present invention may be used to isolate peptide molecular transformation catalysts, develop whole-cell reagents, discover peptides that promote self assembly, discover in vivo targeting peptides for drug and gene delivery, discover and improve peptides binding to materials surfaces, e.g., semiconductors, mapping proteins such as protein contacts, and biomolecular networks, identifying enzyme substrates/inhibitors, identifying receptor agonists/antagonists, isolating inhibitors of bacterial or viral pathogenesis, discovering peptides that mediate endocytosis and cellular entry, mapping antibody and protein epitopes including multiplex mapping, identifying peptide mimics of non-peptide ligands, and isolating metal binding peptides, e.g., for bioremediation, nano-wire synthesis, according to methods known in the art. See Georgiou, G., et al. (1997) Nat. Biotechnol. 15(1):29-34; Pasqualini, R. and E. Ruoslahti (1996) Nature 380(6572):364-366; Whaley, S. R., et al. (2000) Nature 405(6787):665-668; Fields, S. and R. Sternglanz (1994) Trends in Genetics 10(8):286-292; Kim, W. C., et al. (2000) J. Biomol. Screen. 5(6):435-440; Yang, W. P., et al. (1995) J. Mol. Biol. 254(3): 392-403; Poul, M. A., et al. (2000) J. Mol. Biol. 301(5):1149-1161; James, L. C., et al. (2003) Science 299(5611): 1362-1367; Feldhaus, M. J., et al. (2003) Nat. Biotechnol. 21(2):163-170; Kjaergaard, K., et al. (2001) Appl. Environ. Microbiol. 67(12):5467-5473, and Shusta, E. V., et al. (1999) Curr. Opin. Biotechnol. 10(2): 117-122, which are herein incorporated by reference.

As provided herein, the expression vectors of the present invention may be used to elucidate consensus sequences while maintaining diversity in selected populations according to methods known in the art. See Smith, G. P. and A. M.

Fernandez (2004) Biotechniques 36(4):610-614, 616, 618; and Lowman, H. B. (1997) Ann Rev. Biophys. Biomol. Struct. 26:401-424, which are herein incorporated by reference.

The present invention provides library sizes (about $5 \times 10^{10}$) that are about 10-fold larger than typical phage display peptide libraries, with some exceptions. See Deshayes, K., et al. (2002) Chem. Biol. 9(4):495-505; and Fisch, I., et al. (1996) PNAS USA 93(15):7761-7766, which are herein incorporated by reference.

As provided herein, the relatively long 15-mer passenger polypeptides may increase the frequency at which high affinity binders occur relative to the prior art which enables longer consensus motifs and secondary structures to be determined. See Nakamura, G. R., et al. (2002) PNAS USA 99(3): 1303-1308, which is herein incorporated by reference.

The expression vectors of the present invention used in conjunction with FACS provides fine discrimination of clonal affinity, and quantitative separations that take advantage of this sensitivity. See Van Antwerp, J. J. and K. D. Wittrup (2000) Biotechnol. Prog. 16(1):31-37; and Daugherty, P. S., et al. (1998) Protein Eng. 11(9):825-832, which are herein incorporated by reference. Specifically, the fine affinity discrimination provided by FACS allowed isolation of the best sequences binding to streptavidin, CRP, and anti-T7•tag Mab. Further, the display systems herein routinely enabled identification of beneficial cysteine placements to form putative disulfide constrained loops conferring high binding affinity without explicit library design, which alleviates the need to construct and screen twenty or more different libraries, and removes critical assumptions that have limited the affinities of isolated ligands in earlier studies. See Giebel, L. B., et al. (1995) Biochemistry 34(47): 15430-15435; Deshayes, K., et al. (2002) Chem. Biol. 9(4):495-505; and Nakamura, G. R., et al. (2002) PNAS USA 99(3):1303-1308, which are herein incorporated by reference.

Figure 1:
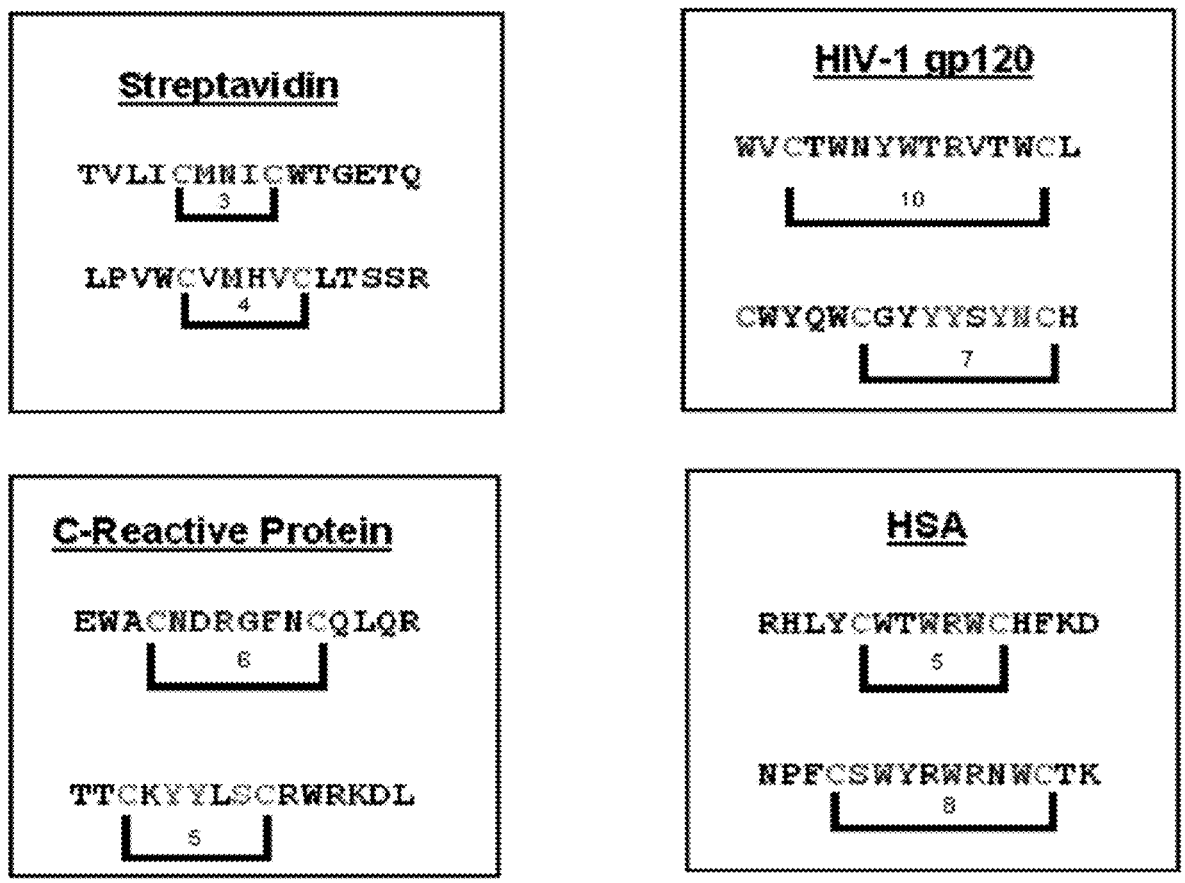
FIG. 1 shows disulphide loops identified de novo, enabling high affinity binding to target proteins. The first sequence in the upper left box is SEQ ID NO:186, the second sequence in the upper left box is SEQ ID NO:187, the first sequence in the upper right box is SEQ ID NO:188, the second sequence in the upper right box is SEQ ID NO:189, the first sequence in the lower left box is SEQ ID NO: 190, the second sequence in the lower left box is SEQ ID NO: 191, the first sequence in the lower right box is SEQ ID NO:192, the second sequence in the lower right box is SEQ ID NO:193.

For example, bacterial display selections for binding to streptavidin yielded a strong preference for CxxVC ligands in all rounds of selection. Yet, only a single report has described the generation and screening of a CxxxC type library using phage display technology. Putative disulfide loops were present in peptides binding to all five of the targets tested despite about a 1000-fold reduced probability of occurring randomly. See FIG. 1. FIG. 1 shows isolated sequences possessing putative disulfide constrained loops. While a strong consensus sequence of NxRGF (SEQ ID NO:315) was present in clones from the selection for CRP binding, FACS screening of the enriched pool resulted in the isolation of a peptide (CRP-1) having the identical consensus, but flanked by two cysteines (EWA-CNDRGFNC-QLQR (SEQ ID NO: 1)). Though a handful of previous studies have reported the identification of peptides with non-designed disulfide bridges, linear libraries most often result in non-cyclic peptides. See Sahu, A., et al. (1996) J. Immunol. 157(2):884-891; and Lu, D., et al. (2003) J. Biol. Chem. 12:12, which are herein incorporated by reference.

Figure 7A:
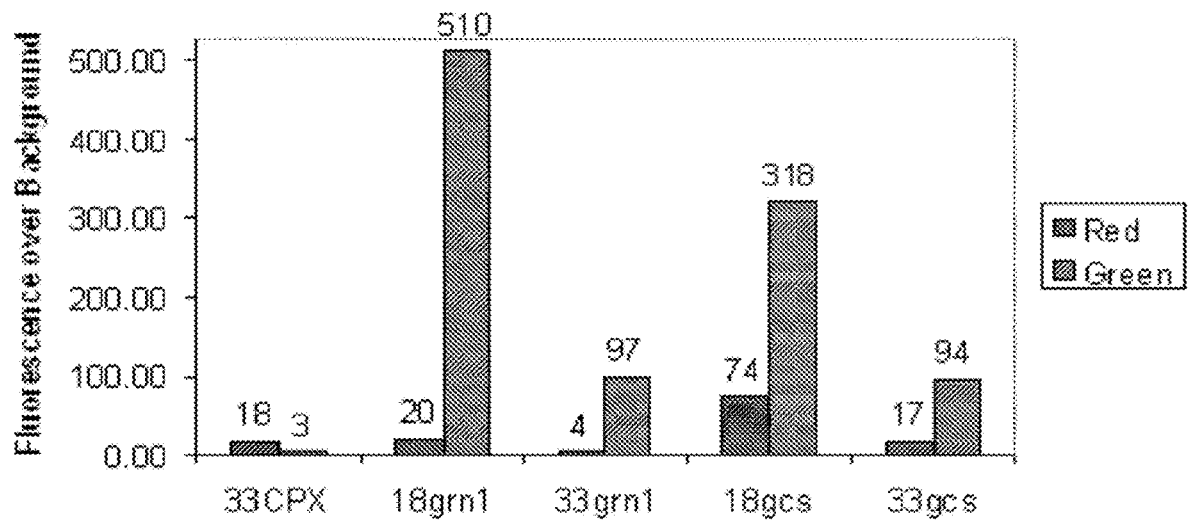
FIG. 7A shows the fluorescence intensity of E. coli cells (MC1061) containing expression plasmids: pBAD33CPX (expressing N-terminal CPX without any passenger protein), pBAD18Grn (expressing GFP from a ColE1 origin), pBAD33Grn expressing GFP from a plasmid with a p15A origin, pBAD18GCS co-expressing alajGFP (G) and SA-1 (Table 2) within the N-terminal CPX scaffold, and pBAD33GCS expressing AlajGFP (G) and SA-1 within the N-terminal CPX scaffold, as measured using flow cytometry.
Figure 7B:
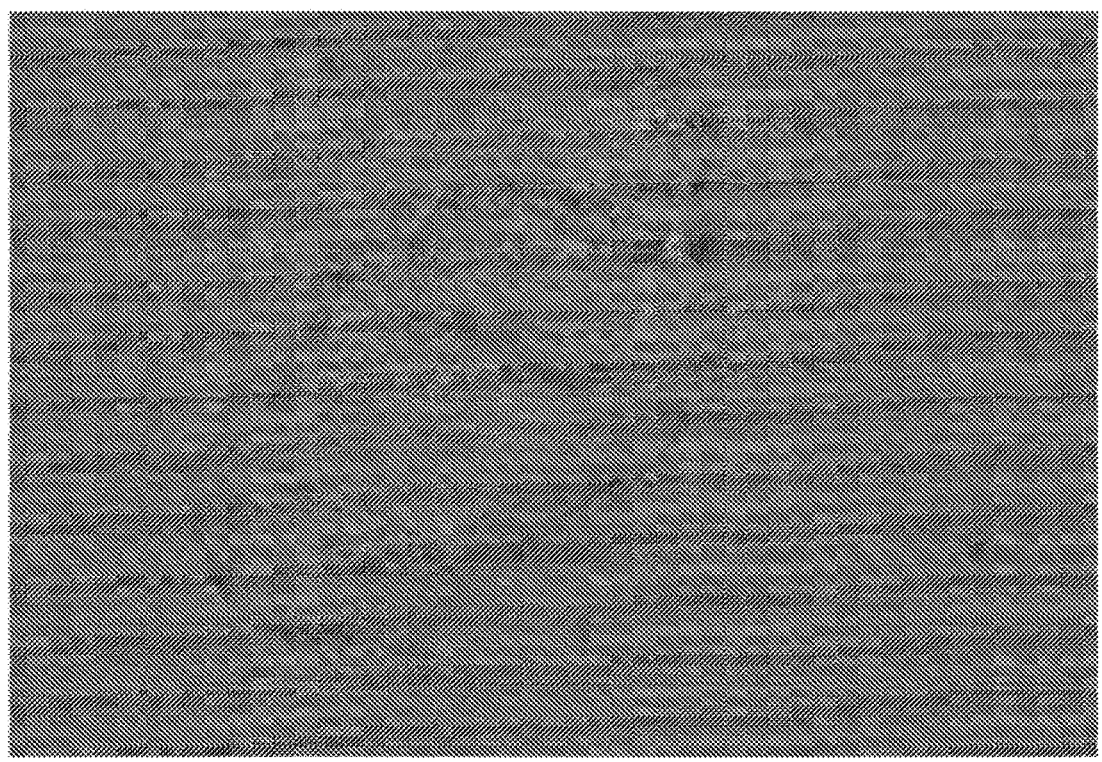
FIG. 7B shows fluorescence microscopy analysis of tumor cells incubated with bacterial cells MC1061/pBAD33 OmpA, which overexpress OmpA without a targeting peptide. Bacteria co-express an autofluorescent protein (e.g. alajGFP) internally, and a selected tumor binding/invading peptide externally.
Figure 7C:
FIG. 7C shows fluorescence microscopy analysis of bacterial cells that target human breast cancer cells. MC1061 bacteria express an autofluorescent protein internally (e.g. AlajGFP), and a selected tumor binding/invading peptide (YCLSYSNGRFFHCPA (SEQ ID NO:311)) externally from plasmid pBAD33OmpA15.

The fact that cyclic peptides were found among the highest affinity clones for all of the ligands tested herein further underscores the importance of ligand rigidity in high affinity binding. Thus, the present invention provides construction of a single library of sufficient size and quality enables routine isolation of high affinity cyclic peptides. For the construction of intrinsically fluorescent libraries, a ribosomal binding site (RBS) known in the art may be introduced downstream of the carrier protein, e.g., OmpX, OmpA, and the like, followed by a suitable fluorescent protein, e.g., alajGFP. See Bessette, P. H. and P. S. Daugherty (2004) Biotechnology Progress 20 (1), which is herein incorporated by reference. The resulting bacteria, when expression is induced by the addition of 0.2% arabinose, are both intrinsically green and display passenger polypeptides as N or C terminal fusion proteins. See FIG. 7. Alternatively, the order may be reversed such that the fluorescent protein is expressed first, followed by the RBS and the permuted OMP sequence.

Sequences with about 10 to about 100 fold higher affinity may be obtained by randomization of non-consensus residues and kinetic FACS selection (using biotin as a competitor). Streptavidin binding peptides may be used as genetically encoded biotin mimics to eliminate the need for chemical labeling of proteins with biotin. Thus, a streptavidin binding peptide selected and affinity matured using this process could be fused, using recombinant methods known in the art, to either the C or N terminus of at least one given nucleic acid molecule. Expression of the nucleic acid molecule would produce a polypeptide having a C or N-terminal peptide tag capable of binding to the commonly used affinity reagent, streptavidin, which may be eluted from the reagent by the simple addition of biotin.

The polypeptide display systems of the present invention allow the creation of renewable whole cell binding reagents in non-specialized laboratories since this method is technically accessible and libraries are reusable. This approach has already proven useful for selecting cell-specific binding peptides, and for performing diagnostic assays using flow cytometry and fluorescence microscopy (unpublished data). Furthermore, the surface displayed polypeptides can be used for parallel or multiplex ligand isolation, and clones can be processed with efficient single-cell deposition units present on many cell sorters. See Feldhaus, M. J., et al. (2003) Nat. Biotechnol. 21(2): 163-170, which is herein incorporated by reference. Consequently, the expression vectors of the present invention may be used in proteomic applications including proteome-wide ligand screens for protein-detecting array development. See Kodadek, T. (2001) Chem. Biol. 8(2):105-115, which is herein incorporated by reference.

A. OmpA Loop 1 Expression Vector

While a purpose of "cell surface display" systems is to present polypeptides on living cells to extracellular targets of any size and molecular composition, LppOmpA', periplasmic display (PECS), and anchored periplasmic expression (APEx) systems, in the prior art do not enable this objective. See Stathopoulos, C., et al. (1996) Appl. Microbiol. & Biotech. 45(1-2): 112-119; Lang, H. (2000) Int. J. Med. Microbiol. 290(7):579-585; Lang, H., et al. (2000) Eur. J. Biochem. 267(1):163-170; Lang, H., et al. (2000) Adv. Exp. Med. Biol. 485:133-136; and Chen, G., et al. (2001) Nat. Biotechnol. 19(6):537-542; Harvey, B. et al. (2004). PNAS. 101(25) 9193-9198, which are herein incorporated by reference. Surface display with LppOmpA' refers to the use of a genetic fusion to localize a polypeptide to the outer membrane of *E. coli*, though not necessarily in a manner that enables binding to arbitrary extracellular targets. Periplasmic display and outer membrane localization with LppOmpA' do not present the displayed protein in a manner compatible with binding to extracellular macromolecules except in rare examples. See Francisco, J. A., et al. (1992) PNAS USA 89(7):2713-2717; Stathopoulos, C., et al. (1996) Appl. Microbiol. & Biotech. 45(1-2):112-119; Francisco, J. A., et al. (1993) PNAS USA 90(22): 10444-10448; Francisco, J. A., et al. (1993) Bio/Technology 11(4):491-495; Francisco, J. A. and G. Georgiou (1994) Annals NY Acad. Sci. 745:372-382; and Georgiou, G., et al. (1993) Trends In Biotechnology 11(1):6-10, which are herein incorporated by reference.

In both of these prior art systems, the displayed protein can interact only with molecules that penetrate the outer membrane, e.g., small and typically hydrophobic molecules, and not with any known protein or macromolecule. This precludes application of the prior art display systems in a wide range of commercially and medically important applications, e.g., protein diagnostics, sensing, and proteomics, cellular array construction, cellular targeting, materials science and materials surface functionalization with whole cells, and the like. Surface localization via a membrane targeting sequence, e.g., the signal sequence and amino acids 1-9 of Lpp, results in membrane disruption and consequently reduced cell growth rates and viability. Application of periplasmic expression (PECS) or anchored periplasmic expression (APex) for protein library screening would require that the cell membrane is removed prior to addition of the target ligand causing cell death. Polypeptide encoding genes on plasmids contained within the cells must then be isolated, PCR amplified to recover genes encoding the corresponding polypeptide, and sub-cloned into an expression vector for library enrichment and repeat screening or selection. Consequently, this approach is much slower, most costly, and less effective than the present system.

In contrast, the OmpA loop 1 expression vector, MC1061/pBAD33L1, of the present invention exemplified herein presents polypeptides at about the outermost point of the first loop of OmpA which increases distance from the lipopolysaccharide surface of E. coli, thereby reducing electrostatic repulsion and steric hindrance between the target element, e.g., protein, and the displayed polypeptide and provides efficient recognition of macromolecules, inorganic surfaces, and cell surfaces. MC1061/pBAD33L1 differs from the previously reported vector utilizing LMG19/pB3OD in several important aspects that change the function of this system. See Daugherty, P. S., et al. (1998) Protein Eng. 11(9):825-832; Daugherty, P. S., et al. (1999) Protein Eng. 12(7):613-621; Daugherty, P. S., et al. (2000) J. Immunol. Methods 243(1-2):211-227; and Daugherty, P. S., et al. (2000) PNAS USA 97(5):2029-2034, which are herein incorporated by reference.

Figure 2:
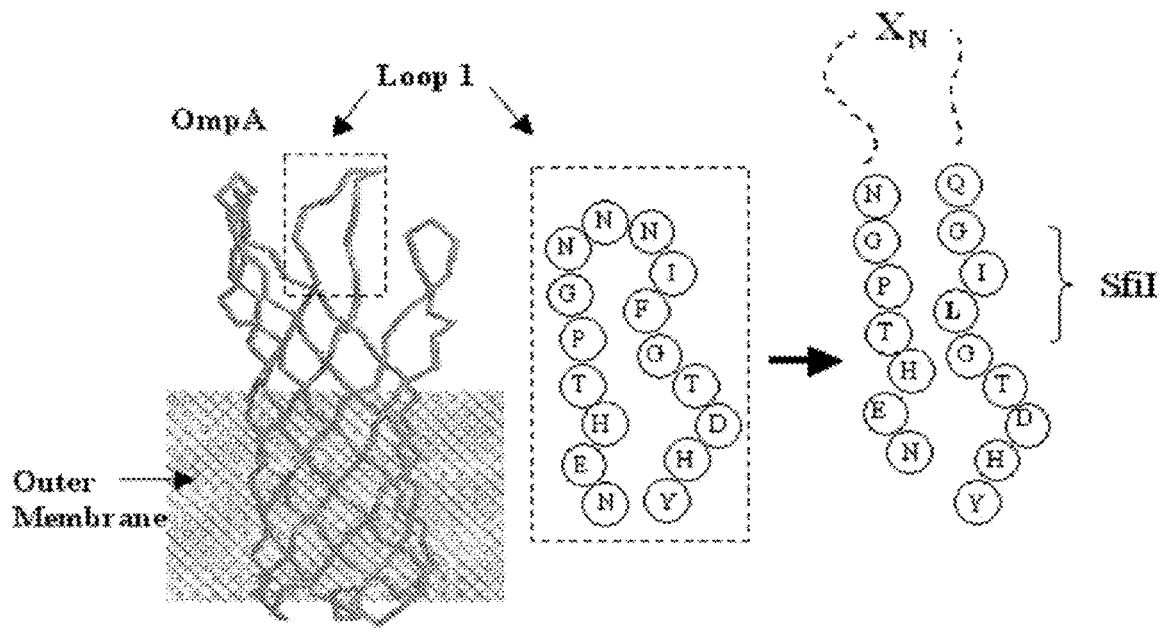
FIG. 2 is an illustration of the location of OmpA loop 1 insertions mediating high level display of oligopeptides, and location of SfiI cloning sites enabling high efficiency cloning. The sequences from left to right are YHDTGFINNNGPTHEN (SEQ ID NO: 313) and YHDTGLIGQXnNGPTHEN (SEQ ID NO: 314), respectively.

The present expression vectors and libraries utilize an extracellular loop of monomeric outer membrane protein (e.g., OmpA & OmpX), which is accessible to arbitrary compositions of matter, capable of being produced at high levels in the outer membrane to enable to best and preferred modes of selection and screening. Polypeptide encoding DNA sequences are inserted genetically within the Omp gene corresponding to the outermost point of loop exposure to the extracellular environment. In some preferred embodiments, this is in the first extracellular loop of OmpA between LIGQ-(X)$_n$-NGPT (SEQ ID NO:2) wherein X is an amino acid and n is any positive integer, as shown in FIG. 2. In contrast, LppOmpA46-159 (LppOmpA'), utilizes a fusion to the newly generated C-terminus resulting from truncation of the OmpA protein at amino acid 159. The benefit of the insertional fusion of the present invention is that it preserves the stability of the overall topological structure of outer membrane protein. Structure is preserved in the construct of the present invention, since adjacent beta-strands maintain molecular interactions that confer stability to the Omp barrel structure. Also, the insertion sites in OmpA are designed by consideration of non-conserved sequences in loops indicating tolerance to substitution and thus insertion.

Figure 3A:
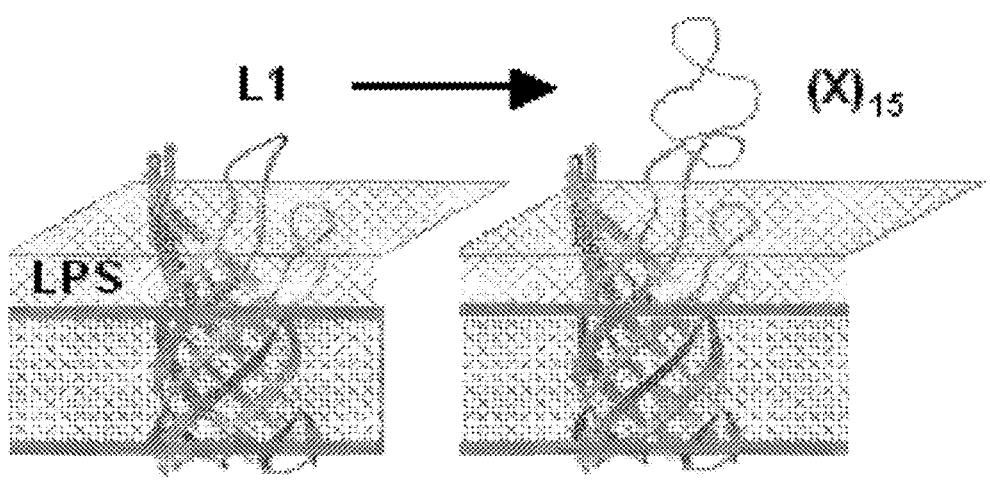
FIG. 3A shows a schematic representation of display of peptides on the surface of E. coli using insertions into the first extracellular loop (L1) of outer membrane (OM) protein A (OmpA). LPS=lipopolysaccharide.
Figure 3B:
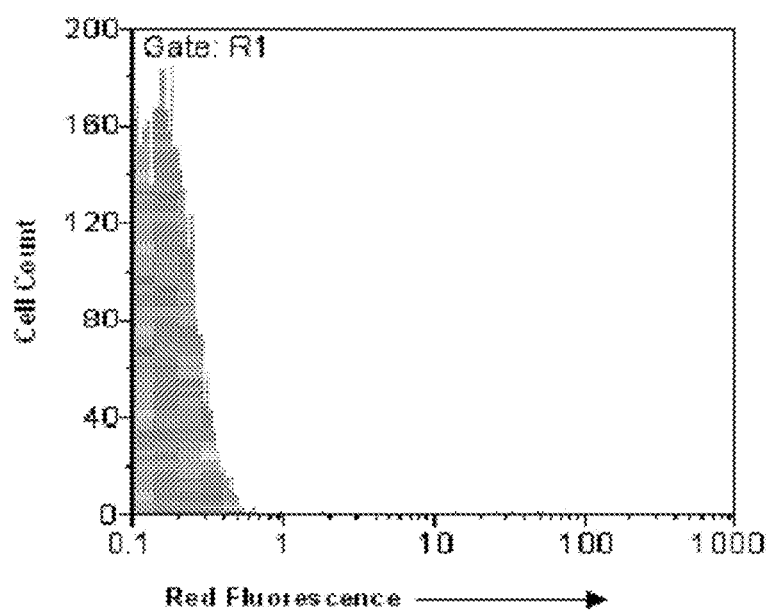
FIG. 3B shows a histogram of flow cytometric analysis of clonal population of cells containing plasmid pB33OmpA overexpressing OmpA without any insertions. Cells were induced for 2 hours and labeled with 10 nM biotinylated-anti-T7•tag mAb and phycoerythrin-conjugated streptavidin.
Figure 3C:
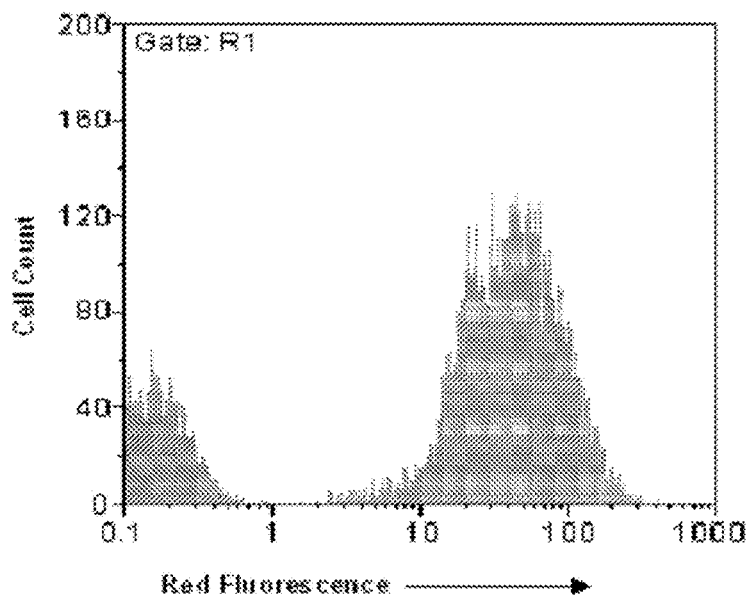
FIG. 3C shows cells containing the plasmid pB33OT1 displaying the T7•tag peptide in OmpA loop 1, induced and labeled as in Figure AB.

To enable construction of a highly diverse polypeptide display library, two mobile loops of OmpA were compared for their ability to display a 15-amino acid epitope. See FIG. 3. E. coli OmpA was chosen as a display scaffold since (1) it is monomeric and can be produced at high levels in the outer membrane under certain conditions; (2) the structures determined using x-ray crystallography and NMR indicate the presence of flexible extracellular loops, and (3) it has been shown to accept loop insertions. See Pautsch, A. and G. E. Schulz (2000) J. Mol. Biol. 298(2):273-8229; Arora, A., et al. (2001) Nat. Struct. Biol. 8(4): 334-830; Freudl, R. (1989) Gene 82(2):229-3631; Mejare, M., (1998) Protein Eng. 11(6):489-9432; Etz, H., et al. (2001) J. Bacteriol. 183(23):6924-6935, which are herein incorporated by reference.

The site of insertion of the display systems of the present invention does not hinder the export of a diverse range of protein and peptide sequences yet retain structural stability. Since loops 1 and 4 are thought to be relatively flexible, it was reasoned that they would be less likely to adversely impact structural stability. Consequently, a 15-mer insertional fusion containing the 11 amino acid epitope of T7 gene 10 (T7•tag) (MASMTGGQQMG) (SEQ ID NO:3) was made in each loop at positions maximally distant from the cell surface within a sequence region poorly-conserved among OmpA homologs. Labeling of whole cells with a biotinylated anti-T7•tag monoclonal antibody (mAb) followed by secondary labeling with streptavidin-phycoerythrin (SAPE) demonstrated that both loops were capable of displaying the T7 epitope with different efficiencies.

Insertions into loop 4 after residue 150 resulted in relatively low level display, since fluorescence signals were only about 2-fold greater than background cellular autofluorescence. On the other hand, loop 1 epitope insertions after residue 26 (FIG. 3) resulted in efficient T7•tag display, with cells exhibiting 300-fold increased fluorescence above background control cells as measured by flow cytometry. Though these experiments were carried out in strain MC1061, which is ompA⁺, the over-expression of the engineered OmpA was easily detectable and did not improve in an otherwise isogenic ompA⁻ host.

As provided in Example 1, one of the important features of the OmpA loop 1 expression vector of the present invention is that a given polypeptide is located in the first extracellular loop of OmpA which is important as (1) the stability of the overall topological structure of OmpA is preserved since the adjacent β-strands are required to maintain the overall stability of the OmpA barrel structure, (2) the polypeptides are properly expressed on the outer surface of the host cell membrane, and (3) large polypeptides may be expressed. Expression and display of a polypeptide using the OmpA loop 1 expression vector exhibits reduced (wild-type-like) membrane permeability to toxic agents which improves viability and growth rates.

In the OmpA loop 1 expression vector exemplified herein, the DNA sequence encoding the polypeptide to be expressed is inserted between the native OmpA sequences that encode amino acid residues N25 and N27 (with numbering with respect to the mature protein); however, it should be noted that OmpA loop 1 expression vectors having other insertion sites within loop 1 are contemplated and may be constructed according to the present invention. See Table 1.

TABLE 1

Loop 1 OmpA homologs from other species suitable for polypeptide display (preferred insertion locations in bold)

| Organism | First Extracellular Loop Sequence |
|---|---|
| Esherichia coli | AKLGWSQYHDTGFNNN-----GPTHENQLGAGA (SEQ ID NO: 4) |
| Esherichia coli | AKLGWSQYHDTGLINNN-----GPTHENQLGAGA (SEQ ID NO: 5) |
| Shigella sonnei | AKLGWSQYHDTGFINNN-----GPTHENQLGAGA (SEQ ID NO: 6) |
| Shigella dysenteriae | AKLGWSQYHDTGFIDNN-----GPTHENQLGAGA (SEQ ID NO: 7) |
| Shigella flexneri | AKLGWSQYHDTGFIPNN-----GPTHENQLGAGA (SEQ ID NO: 8) |
| Salmonella typhimuriurm | AKLGWSQYHDTGFIHND-----GPTHENQLGAGA (SEQ ID NO: 9) |
| Salmonella enterica | AKLGWSQYHDTGFIHND-----GPTHENQLGAGA (SEQ ID NO: 10) |
| Enterobacter aerogenes | AKLGWSQFHDTGWYNSNLNNN-GPTHESQLGAGA (SEQ ID NO: 11) |
| Yersinia Pestis | AKLGWSQYQDTGSIINND----GPTHKDQLGAGA (SEQ ID NO: 12) |
| Klebsiella pneumoniae | AKLGWSQYHDTGFYGNGFQNNNGPTRNDQLGAGA (SEQ ID NO: 13) |

In preferred embodiments of the present invention, the OmpA loop 1 expression vector displays polypeptides on about the outermost point of the first loop of OmpA which increases distance from the lipopolysaccharide surface of the host cell and consequently reduced electrostatic repulsion and steric hindrance between the target element, e.g. protein, and the displayed polypeptide. In some embodiments of the present invention, the nucleic acid sequence of the expression vector was changed to N25Q (to introduce SfiI with a conservative amino acid replacement) and the nucleic acid sequence for N26 was deleted.

Some preferred sites insertion of a given polypeptide may be determined using methods known in the art including analysis of crystal structure, sequence, NMR structure, and then tested using peptide epitopes known to be recognized using common anti-peptide antibodies, e.g., the T7 antibody, anti-c-myc, anti-HA, anti-FLAG. An example of an ideal site for gene insertion is the first extracellular loop of Escherichia coli OmpA between residues Asn-Asn-Asn (SEQ ID NO: 14).

Alternative insertion sites include loop 1 OmpA homologs, which may be identified by multiple sequence alignment to identified non-conserved regions and is preferably chosen such that the displayed protein is located more than about 1 nM from the outer membrane of the cell. See e.g. Table 1.

Other features of the expression vector of the present invention include (1) the use of the OmpA signal sequence, (2) two SfiI restriction sites with one located in OmpA loop 1 immediately adjacent to the insertion site and a second asymmetric SfiI located at an arbitrary distance, but opposite of the insertion site relative to the first SfiI, (3) a single resistance gene for a bacteriocidal antibiotic such as chloramphenicol acetyltransferase, (4) a low copy origin of replication such as p15A for low level expression, and (5) a regulatable promoter, such as araBAD promoter, for controlled transcription.

1. OmpA Signal Sequence pBAD33L1 utilizes the OmpA signal sequence, rather than the Lpp leader sequence employed in LppOmpA, thus providing optimal secretion through the inner membrane.

2. Restriction Enzyme (SfiI) Cleavage Sites

As provided herein, the vector design incorporates two SfiI sites directly into the Omp reading frame and provides a minimized size which permits libraries of a preferred size, about $10^8$ to about $10^{12}$, to be efficiently constructed and used. Specifically, pBAD33L1 contains SfiI restriction sites engineered directly into OmpA loop 1 and 4, thereby enabling high efficiency insertion of cloned genes and large library construction.

The SfiI restriction sites allow the introduction of a nucleic acid molecule which can be digested by a particular enzyme but generates overhangs which cannot react with incorrect DNA substrates, e.g., GGCCXXXXXGGCC (SEQ ID NO: 15), which is recognized by the restriction endonuclease, SfiI, about 1 to about 50 bp upstream of the site where the display molecules will be introduced (the insertion site), and the site GGCCXXXXXGGCC (SEQ ID NO:15) at a distance of about 300 to about 1500 bp downstream of the insertion site. This method permits use of synthetic randomized oligonucleotides that incorporate the same SfiI sequence to be used in a polymerase chain reaction to create sufficient numbers of random DNA fragments.

3. Bacteriocidal Resistance Gene pBAD33L1 contains only a single resistance gene encoding chloramphenicol acetyltransferase, rather the both cat and beta lactamase. The plasmid, pBAD33L1, is therefore smaller, thereby providing greater transformation efficiency than pB30D. Importantly, owing to size and absence of beta-lactamase expression pBAD33L1 imposes a smaller burden upon cell growth than previous vectors, thereby improving library screening. Further the ability to use a bacteriocidal antibiotic for selection is preferred in order to prevent plasmid loss and the outgrowth of bacterial cells commonly resistant to the antibiotic.

4. Low Copy Origin of Replication

The use of a low copy plasmid utilizing the p15A origin of replication enabled expression without a significant reduction of cell viability. See FIG. 4. In contrast, an analogous display vector having a pMB1 origin provided high level expression but resulted in rapid arrest of cell growth shortly after induction (data not shown). In some embodiments, expression of the displayed protein does not hinder cell growth in order to prevent clonal competition that reduces library diversity and interferes with selection. As an alternative to using a low copy plasmid, a higher copy plasmid, e.g., plasmid containing the pMB1 origin of replication, could be used in combination with a promoter having reduced transcriptional activity.

5. Regulatable Promoter

The expression vectors of the present invention incorporate a tightly controlled promoter for regulated transcription. As exemplified herein, the promoter used is from the arabinose araBAD operon of E. coli. See Guzman, L., et al. (1995) J. Bacteriol. 177(14):4121-4130; Johnson, C. M. and R. F. Schleif (1995) J. Bacteriol. 177(12):3438-3442; Khlebnikov, A., et al. (2000) J. Bacteriol. 182(24):7029-7034; and Lutz, R. and H. Bujard (1997) Nucleic Acids Res. 25(6): 1203-1210, which are herein incorporated by reference. Protein production is initiated by addition of the sugar L-arabinose, and stopped by the removal of arabinose and addition of glucose. Regulation prevents unwanted changes in the representation frequency of the rare desired target cells during growth before and after the selection or screening step.

The use of a tightly regulatable promoter prevents loss of mildly toxic sequences during growth, maintain full library diversity, and improve single round enrichment efficiency. See Daugherty, P. S., et al. (1999) Protein Eng. 12(7):613-621, which is herein incorporated by reference. Use of the arabinose inducible promoter from the araBAD operon enabled tight repression in the absence of arabinose during library propagation and reproducible induction of surface display of peptide insertions under saturating inducer conditions. High level display with minimal cell death or growth inhibition (data not shown) was obtained about 1 to about 4 hours after induction. In subsequent experiments, an induction period of about 2 hours was typically used before selection or screening to minimize potential toxicity.

Any promoter could be used according to the present invention that (1) provides tight repression of expression during library propagation before and after screening, and (2) provides adequate levels of expression to enable binding magnetic particles and or be detected using flow cytometry instrumentation. In alternative embodiments, a modulatable promoter may be used, which enables "rheostat" control of expression over a range of potentially desirable expression levels. Examples of such promoters include, the araBAD system, with co-expression of a constitutive arabinose transporter protein. See Khlebnikov, A., et al. (2000) J. Bacteriol. 182(24):7029-7034, which is herein incorporated by reference.

As disclosed in Example 1, for library construction of the OmpA loop 1 expression vector, inserts were chosen to have a length of about 15 codons while allowing all possible amino acids (using NNS degenerate codons) at each position. In addition to increasing the physical distance from the cell surface, longer length insert libraries, e.g., 15-mer, offer the advantage of providing more copies of short sequences while allowing for longer binding motifs to emerge. The resulting library of about $5 \times 10^{10}$ independent transformants provides a sparse sampling of the sequence space available to a 15-mer (0.0000002%), but is expected to contain all possible 7-mer sequences (greater than about 99% confidence).

In some embodiments of the present invention, a DNA library is constructed containing preferably greater than about $10^8$ sequences, and preferably more than about $10^{10}$ unique sequence members, using methods known in the art. This library size is preferred since library size has been shown to correlate with the quality (affinity and specificity) of the selected sequences. See Griffiths, A. D. and D. S. Tawfik (2000) Curr. Opin. Biotechnol. 11(4):338-53, which is herein incorporated by reference.

In some embodiments, a polypeptide library may be prepared by introduction and expression of nucleic acid sequences which encode polypeptides having about 1 to about 1000, preferably about 2 to about 30 amino acids in length. As provided herein, the present invention uses high DNA concentrations of more than about 0.1 µg per µl during transformation which resulted in one or more independent plasmid molecules in each host cell. This multiple-plasmid transformation step, yields a larger number of unique peptides in the same volume of liquid, providing the overall results better than prior art methods which provide only one molecule per cell. In some embodiments, a mixture of a plurality of different expression vectors and/or plasmids may be employed to provide cooperative binding two different displayed peptides on the same surface, to present a protein having multiple subunits, and the like.

A desired number of polypeptides may be displayed on the surface for different purposes. As exemplified herein, the method of the present invention utilizes an induction period of about 10 minutes to 6 hours to control total expression levels of the display polypeptide and the mode of the subsequent screen or selection such that the level of expression has no measurable effect upon the cell growth rate. See FIG. 4. In some embodiments, shorter time periods may be used to reduce avidity effects in order to allow selection of high affinity monovalent interactions. As provided herein, the ability to control display speeds the process and yields higher quality results, e.g., sequences that bind to a target with higher affinity.

Figure 5:
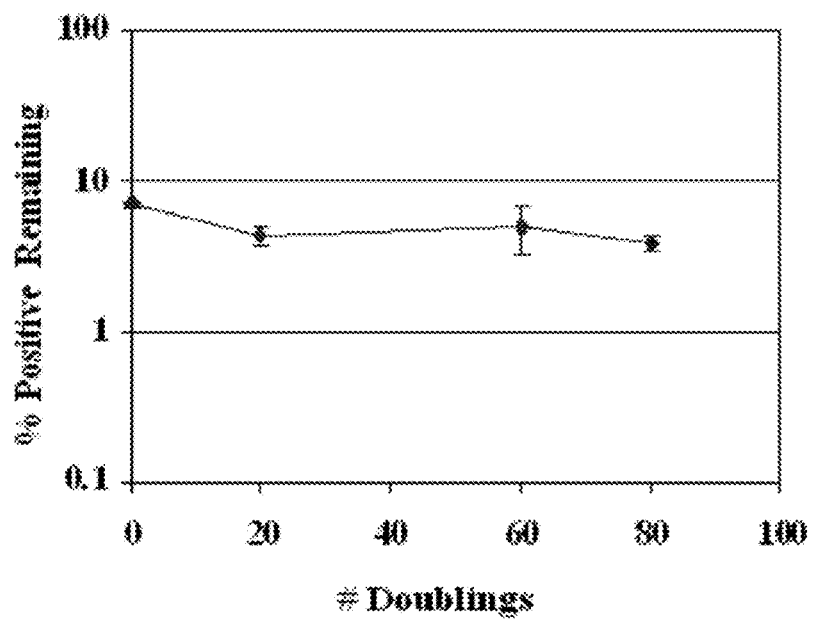
FIG. 5 shows maintenance of library diversity through 80 doublings indicating that library can be expanded indefinitely for reuse.

In some embodiments, a cell concentration by a factor of about 10 may be used to enable complete processing of the entire pool of diversity in a volume of about 10 to about 100 ml. The library may be expanded by propagation by a factor of more than about 100-fold under conditions which prevent synthesis of the library elements, for example, with glucose to repress the araBAD or lac promoters, and aliquots of the library may be prepared to represent a number of clones which is more than about three fold greater than the total number of library members. See FIG. 5.

For library selection, a subset of the total library, either randomly divided, or chosen for specific properties could be used as a starting point for screening. Either MACS or FACS methods known in the art may be used, in place of sequence application of MACS and then FACS. As an alternative to FACS, methods known in the art that enable physical retention of desired clones and dilution or removal of undesired clones may be used. For example, the library may be grown in a chemostat providing continuous growth, diluting out only those cells that do not bind to a capture agent retained in the vessel. Alternatively, hosts may be cultured with medium having ingredients that promote growth of desired clones.

Instead of using random synthetic peptides to provide genetic diversity, fragment genomic DNA of varying lengths, cDNA of varying lengths, shuffled DNAs, and consensus generated sequences may be employed in accordance with the present invention.

Non-natural amino acids having functionality not represented among natural amino acids, e.g., metal binding, photoactivity, chemical functionality, and the like, may be displayed on the surface using a suitable host. In this case, the library or an equivalent library may be transformed into strains engineered to produced non-natural amino acids. See Kiick, K. L. et al. (2001) FEBS Lett. 502(1-2):25-30; Kiick, K. L., et al. (2002) PNAS USA 99(1):19-24; Kirshenbaum, K., et al. (2002) Chembiochem. 3(2-3):235-237; and Sharma, N., et al. (2000) FEBS Lett. 467(1):37-40, which are herein incorporated by reference. Peptides incorporating non-natural amino acids are isolated by selection or screening for functions which require inclusion of the non-natural monomers into the displayed polypeptide.

Displayed polypeptides may be made to include post-translation modifications, including glycosylation, phosphorylation, hydroxylation, amidation, and the like, by introduction of a gene or set of genes performing the desired modifications into the strain used for screening and selection, e.g., MC1061 or comparable host strain. Genes performing such post-translational modifications may be isolated from cDNA or genomic libraries by cotransformation with the library and screening for the desired function using FACS or another suitable method. For example, post-translational glycosylation activities (enzymes) can be found co-transforming.

The polypeptides displayed by a carrier protein preferably possess a length that preserves the folding and export of the carrier protein, such as OmpA, OmpX, or the like, while presenting significant sequence and structural diversity. In some embodiments, the carrier protein, such as an outer membrane protein (Omp), may be modified by rational redesign or directed evolution methods known in the art to increase levels of display or improve polypeptide presentation. For example, the carrier protein may be optimized by random point or cassette mutagenesis and screening for improved presentation. Sequences not required for display, such as the C-terminal domain of OmpA, may be removed from the display carrier protein in order to minimize metabolic burden and improve total display levels.

In some embodiments, an alternative Omp, such as OmpX, OmpF, LamB, OmpC, OmpT, OmpS, FhuA, FepA, FecA, PhoA, and TolC, may be used as the carrier protein. Epitope insertion assays known in the art, and here exemplified by the insertion of the T7tag peptide into OmpA, OmpX, and CPX polypeptides, may be used to identify suitable passenger insertion sites conferring display at the surface. Growth assays known in the art, may be used to identify insertion sites which do not alter growth rates or viability as a result of display. See FIG. 4.

Figure 6A:
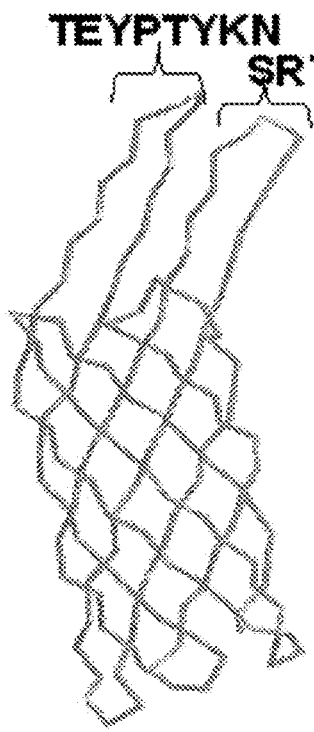
FIG. 6A shows two permissive sites for polypeptide display in OmpX identified by multiple sequence alignment. The first sequence is SEQ ID NO: 194 and the second sequence is SEQ ID NO: 195. Sites are suitable since they (1) are located more than about 1 nM from the cell surface, (2) they are non-conserved across different species, (3) they exhibit conformational flexibility, and (4) they are located in a relatively small monomeric Omp protein.
Figure 6B:
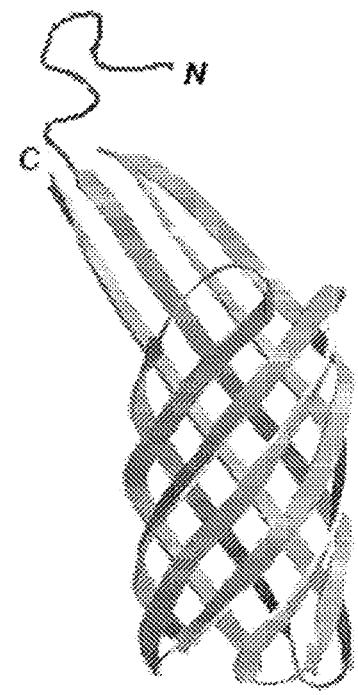
FIG. 6B shows bacterial display libraries as N-terminal fusions to a circularly permuted variant of OmpX.

Multimeric membrane proteins could be used, either in native form for polyvalent display, e.g., three peptide on trimeric OmpF, or could be engineered to be monomeric, thereby mimicking OmpA, OmpX, or OmpT. See FIG. 2 and FIG. 6. However, in preferred embodiments, display is via a monomeric protein, e.g., OmpA, OmpX, or catalytically inactive mutant of OmpT, present at the cell surface in excess of 10,000 copies per cell.

In some embodiments, an alternative protein scaffold protein may be used to present the passenger polypeptide, e.g., random peptide, to be displayed. For example the green fluorescent protein or an alpha helix bundle protein, knottin, acyclic permutant of a cyclic peptide (e.g., Kalata-B1) may be used as a spacer and scaffold element, or to provide multiple additive or synergistic functions, e.g., fluorescence & binding, binding, and catalytic transformation, binding and assembly, and the like. See FIG. 7.

As exemplified herein, the present invention utilizes a bacterial strain, MC1061 which exhibits (1) high plasmid transformation efficiency of greater than about $5 \times 10^9$ per microgram of DNA, (2) a short doubling time, i.e., 40 minutes or less, during exponential growth phase, (3) high level display of the given polypeptide, and (4) effective maintenance of the expression ON and OFF states. See FIG. 3, FIG. 4, and FIG. 5. In some embodiments, alternative biological entities known in the art may be used. In preferred embodiments, the biological entity is deficient in proteolytic machinery in order to prevent protein degradation. See Meerman, H. J., Nature Biotechnol. 12(11): 1107-1110, which is herein incorporated by reference. In some embodiments, a biological entity that makes truncated or otherwise modified lipopolysaccharides on its surface may be used to minimize steric effects upon binding to large biomolecules including proteins, viruses, cells, and the like. In some preferred embodiments, the biological entity has a genotype that aids the expression vector in regulating more tightly the production of the polypeptide to be displayed. The biological entity may be modified using methods known in the art, including random mutagenesis, DNA shuffling, genome shuffling, gene addition libraries, and the like.

As provided herein, expression and display of the polypeptide may be accomplished by induction of protein expression by contacting with arabinose, preferably about 10 to about 60 minutes, and more preferably about 10 to about 20 minutes at 25° C. Controlling expression and display minimizes potential avidity effects that can result from excessive surface concentration of the displayed peptide. Cells were grown in LB media overnight or for about 1 to about 3 hours, induced for about 5 minutes to about 5 hours at about 4 to about 37° C., and preferably for about 10 to about 20 minutes at about 25° C. Cells were washed once in phosphate buffered saline (PBS) and resuspended in PBS with biotin conjugated target protein. The cells were then washed once to remove unwanted unbound proteins and other debris, and incubated with a fluorescent, biotin binding reagent, preferably streptavidin-phycoerythrin (Molecular Probes, Eugene, Oreg.), or the like. Unbound fluorescent reagent was then removed by washing and cells were analyzed by flow cytometry. Cells displaying the foreign protein or peptide possess a fluorescence intensity of about 8 to about 200 fold greater than non-peptide display cells, i.e., cellular autofluorescence, and preferably about 8 to about 20 fold, indicating a moderate level of display that will not result in avidity effects (about 1000 to about 10,000 copies).

As provided herein, use of MC1061/pBAD33L1 allowed the identification of optimal disulphide bond placements in selected peptides directly from large random libraries which increases the affinity of the selected ligands, and provides utility for applications requiring stability, e.g., serum stability in vivo. The display systems of the present invention allow the use of magnetic selection which provides relatively simple and fast, e.g., about 2 days, isolation of peptides that bind to a target ligand with high binding affinity.

As provided in Example 1, the ability of the displayed polypeptides to bind given ligands was tested. Five unrelated target proteins were chosen: a monoclonal IgG antibody binding to a known epitope (anti-T7•tag mAb), human serum albumin (HSA), human C-reactive protein (CRP), streptavidin, and HIV-1 GP120. For each of five protein targets tested, magnetic selection enabled enrichment of clones displaying protein binding peptides from non-binding clones. Abundant streptavidin binding peptides were first depleted from the library using one round of magnetic selection with streptavidin functionalized magnetic particles. The remaining cells were incubated with biotinylated target proteins, and subsequently with biotin-binding magnetic particles to capture cells with bound target protein. Each cycle of magnetic selection was followed by overnight growth to amplify the selected population.

Figure 9:
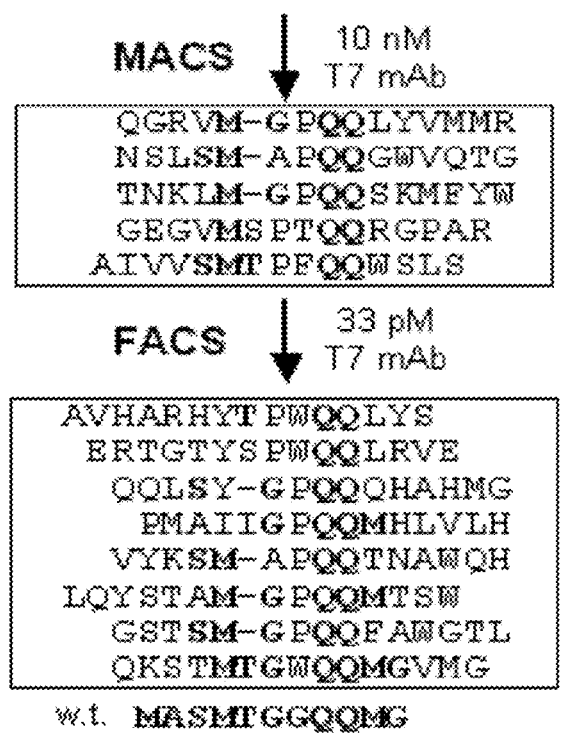
FIG. 9 shows representative sequences of surface displayed high-affinity anti-T7tag mAb binding peptides isolated using magnetic selection and FACS with differing target ligand concentrations. Two rounds of MACS were performed at 10 nM antibody concentration, followed by FACS using 33 pM antibody. Bold residues indicate positions of identity with the wild-type T7•tag epitope, shown at the bottom, against which the antibody was raised. From top to bottom the sequence identifiers are SEQ ID NOs: 196-208. The sequence identifier for the wild type sequence at the bottom is SEQ ID NO:312.

Flow cytometry was used to monitor the progress of magnetic selection using as fluorescent probes either streptavidin-phycoerythrin or fluorescently conjugated anti-biotin antibodies. See FIG. 9. One or two rounds of magnetic selection were sufficient to enrich a population containing a significant fraction of binders for each of the five targets tested. In the case of selection for anti-T7•tag mAb binding, one cycle was sufficient to enrich binding peptides to nearly about 50% of the population from an initial frequency of about 1 in 50,000—a single round enrichment of about 25,000-fold. The initial frequency of T7•tag mAb binding clones indicated that roughly about $2 \times 10^5$ unique peptide sequences were capable of binding when using a target concentration of 10 nM.

The frequency of target protein binding peptides within the library population was found to vary significantly among different targets, suggesting that the library was more "fit" for binding some antigens. The highest frequency of target binding cells was observed with the anti-T7•tag mAb. Similarly, a high initial frequency of positive cells was observed when using streptavidin and CRP as targets. On the other hand, a reduced frequency (less than about $1:10^6$) of GP120 binding clones was observed in the unselected library, possibly reflecting the heavily glycosylated surface of this target. The frequency of target binding clones in the library was consistent with the probability of occurrence of certain critical motifs involved in molecular recognition. In the anti-T7•tag mAb selection, for example, the initial frequency binding clones ($2:10^5$) is consistent with the expected frequency of the identified "core" motif MxP(x/-)QQ (SEQ ID NO:316 and SEQ ID NO:317) of about $2:10^5$. Similarly, for the CRP selection, the consensus motif, NxRGF (SEQ ID NO:315), is expected to occur at a frequency of roughly about $5:10^5$. Thus, cytometric analysis of the library populations prior to screening provided useful statistical information regarding the expected frequency of target protein-binding peptides.

Cell sorting instrumentation was applied as a quantitative library screening tool to isolate the highest affinity clones from the magnetically enriched populations (FIG. 3), estimated to represent about $10^5$ to about $10^7$ unique sequences. Two fundamentally different approaches were applied for quantitative screening, as previously described, on the basis of either equilibrium binding affinity (Equilibrium Screen) or dissociation rate constants (Kinetic Screen). See Daugherty, P. S., et al. (2000) J. Immunol. Methods 243(1-2):211-227; and Boder, E. T. and K. D. Wittrup (1998) Biotechnology Progress 14(1):55-62, which are herein incorporated by reference. In most cases, appropriate antigen concentrations for equilibrium screening were determined by flow cytometric analysis of about $10^6$ clones after labeling with a range of different target protein concentrations.

Figure 8A:
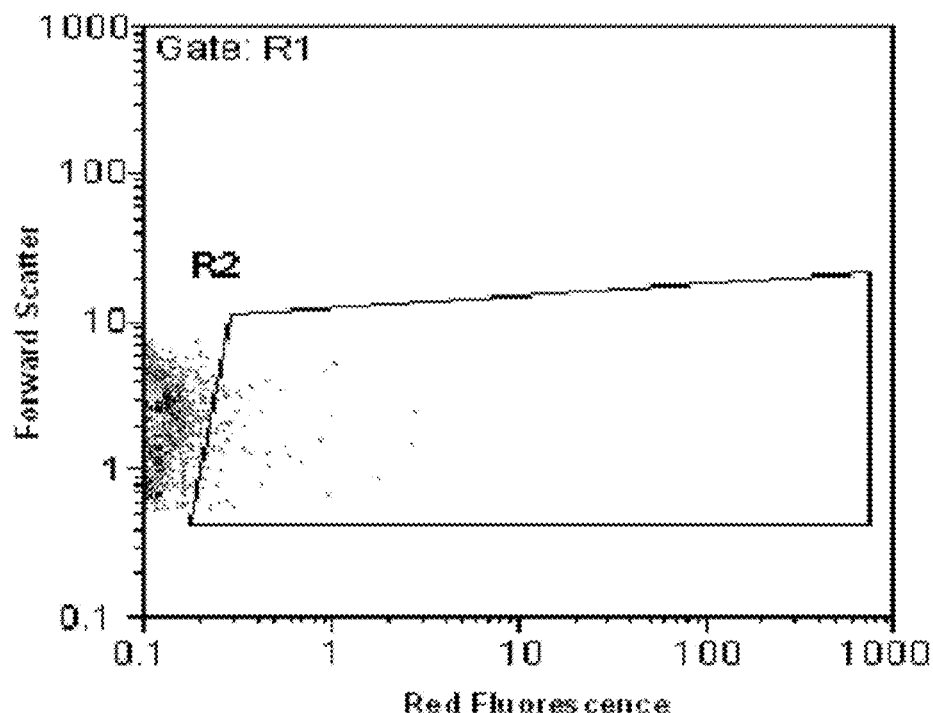
FIG. 8A shows enrichment of C-reactive protein binding peptides as measured using flow cytometry. Induced cells were labeled with 10 nM biotin-CRP and 6 nM SAPE in an unselected library population.
Figure 8B:
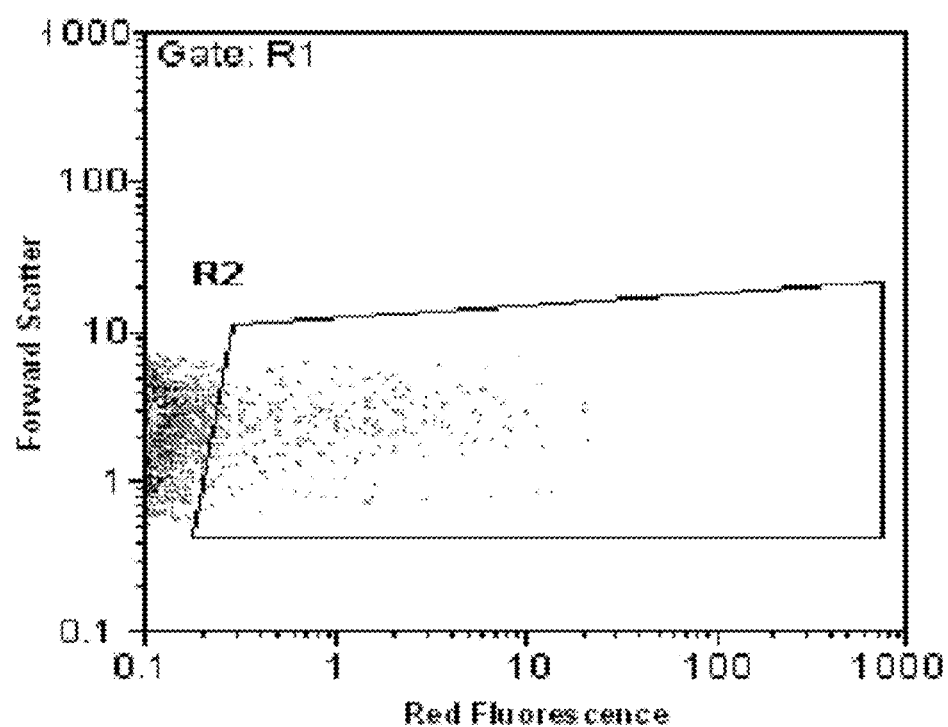
FIG. 8B shows enrichment of C-reactive protein binding peptides as measured using flow cytometry. Induced cells were labeled with 10 nM biotin-CRP and 6 nM SAPE following two rounds of magnetic selection.
Figure 8C:
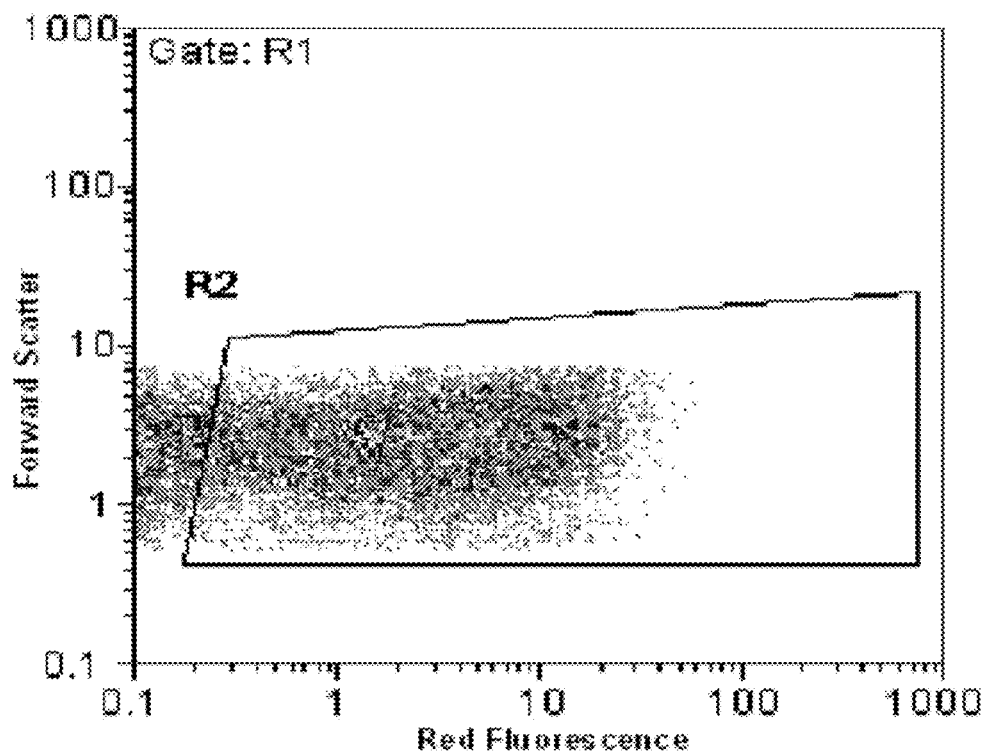
FIG. 8C shows enrichment of C-reactive protein binding peptides as measured using flow cytometry. Induced cells were labeled with 10 nM biotin-CRP and 6 nM SAPE following two rounds of magnetic selection and one round of FACS.

For equilibrium screening, cell populations were labeled with limiting concentrations of the target proteins, and all cells exhibiting fluorescence intensities above background autofluorescence were collected. See FIG. 8. Thus, the ligand concentration, and not the lower intensity limit of the sort window, was used to as the criteria for acceptance. In the case of the streptavidin selection, kinetic screening was performed using free biotin as a competitor. In the absence of biotin, streptavidin binding peptides exhibited substantially slower dissociation rates, likely due to rebinding effects. The apparent binding affinities of isolated clones were generally predictable from the antigen concentrations used for screening Typically, the apparent dissociation constants were roughly ten-fold higher than the ligand concentration used for screening. See Table 2.

TABLE 2

| Clone ($K_D$) | Sequence | | Target Conc. (nM)[a] |
|---|---|---|---|
| C-Reactive Protein | | | |
| CRP-1 (1 nM) | EWACNDRGFNCQLQR | SEQ ID NO: 16 | 0.1 |
| CRP-2 (3 nM) | FPIYNQRGFITLASP | SEQ ID NO: 17 | 0.1 |
| CRP-3 | HMRWNTRGFLYPAMS | SEQ ID NO: 18 | 1.0[b] |
| CRP-4 | RYIMNHRGFYIFVPR | SEQ ID NO: 19 | 1.0[b] |

TABLE 2-continued

| Clone ($K_D$) | Sequence | | Target Conc. (nM)[a] |
|---|---|---|---|
| CRP-5 | VRTWNDRGFQQSVDR | SEQ ID NO: 20 | 1.0[b] |
| CRP-6 (8 nM) | MIFNSRGFLSLMSSG | SEQ ID NO: 21 | 10.0 |
| CRP-7 | LMNWRGFMVPRESPK | SEQ ID NO: 22 | 10.0 |
| CRP-8 | WTKLKNSRGFELQLD | SEQ ID NO: 23 | 10.0 |
| CRP-9 | PYLNARGFSVTREQI | SEQ ID NO: 24 | 10.0 |
| Consensus | IXNXRGF | SEQ ID NO: 25 | |
| CRP-10 (5 nM) | YPPRFQYYRFYYRGP | SEQ ID NO: 26 | 0.1 |
| CRP-11 | TDFLSYYRVYRTPLQ | SEQ ID NO: 27 | 1.0[b] |
| CRP-12 | TFMPSYYRSWGPPPT | SEQ ID NO: 28 | 1.0[b] |
| CRP-13 | TTCKYYLSCRWRKDL | SEQ ID NO: 29 | 10.0 |
| Consensus | SYYRSY | SEQ ID NO: 30 | |
| Streptavidin | | | |
| SA-1 (10 nM) | RLEICQNVCYYLGTL | SEQ ID NO: 31 | 6.0[c] |
| SA-2 (8 nM) | ICSYVMYTTCFLRVY | SEQ ID NO: 32 | 6.0[d] |
| SA-3 (4 nM) | TVLICMNICWTGETQ | SEQ ID NO: 33 | 6.0[d] |
| SA-4 | VTSLCMNVCYSLTTY | SEQ ID NO: 34 | 6.0[d] |
| SA-5 | YWVCMNVCMYYTARQ | SEQ ID NO: 35 | 6.0[d] |
| SA-6 | LPVWCVMHVCLTSSR | SEQ ID NO: 36 | 6.0[d] |
| SA-7 | NEWYCQNVCERMPHS | SEQ ID NO: 37 | 6.0 |
| SA-8 | IMMECFYVCTIANTQ | SEQ ID NO: 38 | 6.0 |
| SA-9 | TKVQCTMVCYGMSTT | SEQ ID NO: 39 | 6.0 |
| SA-10 | SITICWYTCMVQKTA | SEQ ID NO: 40 | 6.0 |
| SA-11 | ADTICWYVCTISVHA | SEQ ID NO: 41 | 6.0 |
| Consensus | ICMNVC | SEQ ID NO: 42 | |
| Serum Albumin | | | |
| HSA-1 | NPFCSWYRWRNWCTK | SEQ ID NO: 43 | 100.0 |
| HSA-2 | RHLYC-WT-WR-WCHFKD | SEQ ID NO: 44 | 100.0 |
| | CXWXXWRXW | SEQ ID NO: 45 | |
| HSA-3 | SYISTWLNFLFCGQS | SEQ ID NO: 46 | 100.0 |
| HSA-4 | NNYSAWLRCLLRAYS | SEQ ID NO: 47 | 100.0 |
| Consensus | SXWLXXLXXXXS | SEQ ID NO: 48 | |
| HIV-1 GP120 | | | |
| GP120-1 | GDTWVWYCWYWTRSI | SEQ ID NO: 49 | 15.0 |
| GP120-2 | WVCTWNYWTRVTWCL | SEQ ID NO: 50 | 15.0 |
| Consensus | WVXXXXYWTR | SEQ ID NO: 51 | |
| GP120-3 | PWCWMWTKGRWYYVA | SEQ ID NO: 52 | 0.6 |
| GP120-4 | QIQWCWVNHRWSPVV | SEQ ID NO: 53 | 0.6 |
| GP120-5 | WVAGYWWCWSVMYRS | SEQ ID NO: 54 | 15.0 |

TABLE 2-continued

| Clone ($K_D$) | Sequence | | Target Conc. (nM)[a] |
|---|---|---|---|
| GP120-6 | TWTWCWRNYIWQLST | SEQ ID NO: 55 | 15.0 |
| GP120-7 | QEWRQLTRWCWVQIK | SEQ ID NO: 56 | 15.0 |
| GP120-8 | QTATVSYWCYWWWKV | SEQ ID NO: 57 | 15.0 |
| Consensus | WCWXXXK | SEQ ID NO: 58 | |

[a]The concentration used for the final selection.
[b]Dissociation in presence of 100 nM unbiotinylated CRP for 20 minutes.
[c]Dissociation in presence of 1 µM biotin for 2.5 hours.
[d]Dissociation in presence of 1 µM biotin for 6 minutes.

Table 2 shows peptide sequences of isolated clones binding to streptavidin, CRP, HSA, and GP120. Sequences were aligned using the Clustal W algorithm, and consensus residues are shown below each group. For selected clones, the apparent whole cell $K_D$ as measured by flow cytometry is indicated.

Figure 10A:
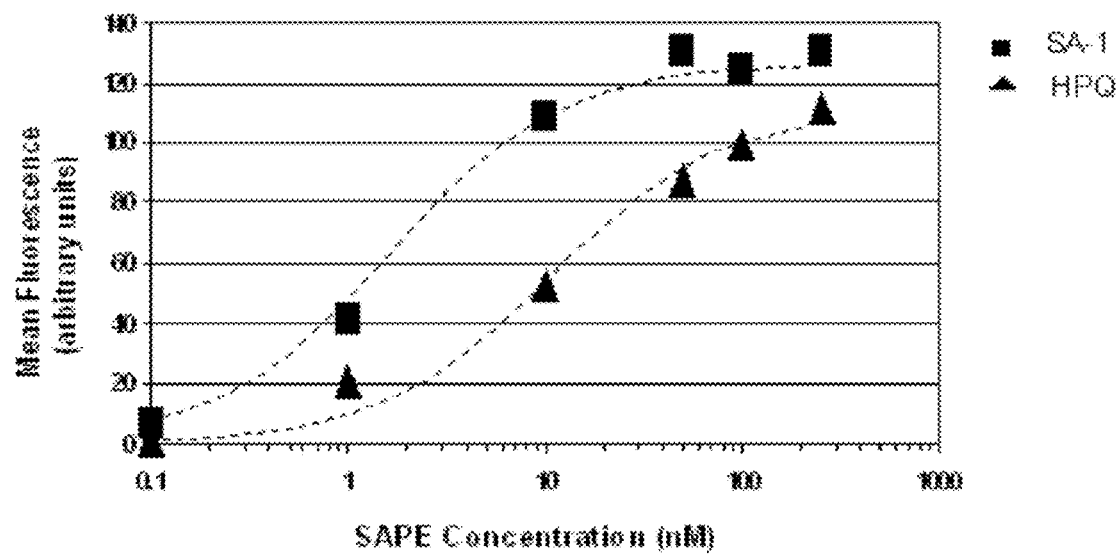
FIG. 10A is a measurement of the binding affinities of cell surface displayed streptavidin binding peptides using flow cytometry and biotin as a competitor as described herein.
Figure 10B:
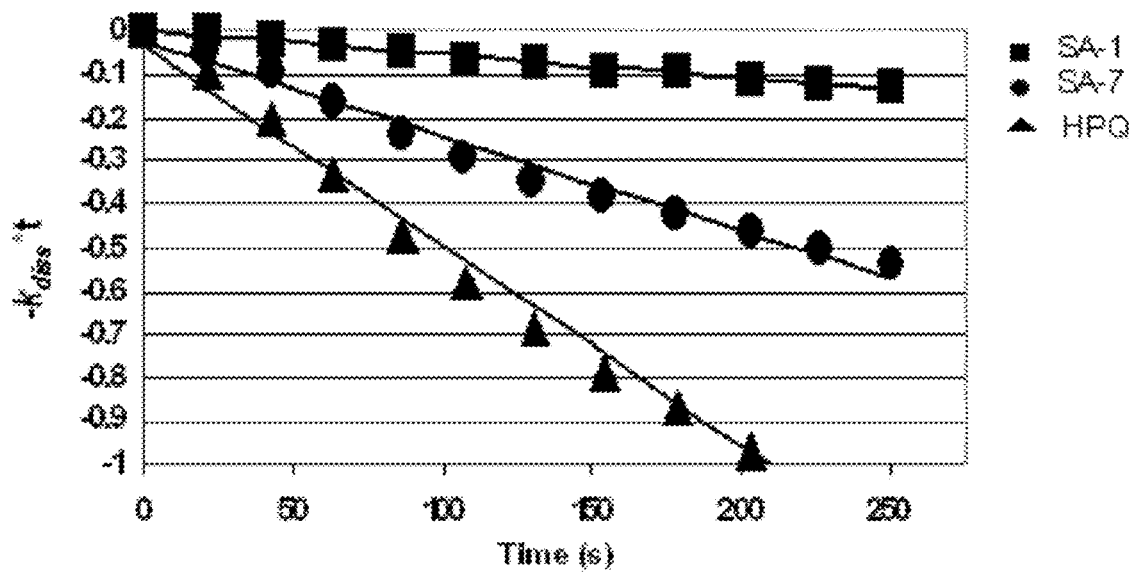
FIG. 10B is a measurement of the binding affinities of cell surface displayed streptavidin binding peptides using flow cytometry and biotin as a competitor as described herein. Determination of dissociation rate constants ($k_{diss}$) of cell surface displayed peptides. Peptide sequences of clones SA-1 and SA-7 are listed in Table 2. Clone HPQ contains the sequence SAECHPQGPPCIEGR (SEQ ID NO:209) inserted into OmpA loop 1 for comparison.

Consensus sequences were readily apparent for each of the target proteins after two to three rounds of magnetic selection and one or two rounds of FACS. See Table 2, FIG. 9. The strongest consensus sequence for anti-T7•tag mAb binding in a single clone was lengthened to seven residues SMGPQQM (SEQ ID NO:59), despite the low frequency of such clones in the library, i.e., about $1:10^{10}$. One anti-T7•tag mAb binder, (FIG. 9) possessed seven identities and one similarity with the wild-type T7•tag sequence. Considering codon usage, such a clone would be expected to occur at a frequency of less than about one in $10^{10}$. Consensus sequences for HSA and for HIV-1 GP120 binding included several hydrophobic residues, and a high frequency of clones with one or two cysteine residues. In some cases, FACS resulted in enrichment and isolation of putatively cyclic peptides incorporating the consensus sequence. For example, the highest affinity CRP binding clone (CRP-1, Table 2) from stringent FACS screening possessed the consensus NxRGF (SEQ ID NO: 315) flanked by cysteines—CNDRGFNC (SEQ ID NO:60). Residues outside of the cyclic constrained consensus also contributed to improved function since two streptavidin binding clones with identical disulfide loops (CQNVC (SEQ ID NO:61)) possessed dissociation rate constants differing by four-fold. See FIG. 10B. The overall length of the visible consensus sequences spanned as many as about ten or about eleven residues for anti-T7•tag mAb (SMGPQQMXAW (SEQ ID NO:62) or SMGPQQMAW (SEQ ID NO:63)) or CRP (IXNXRGFXXXV (SEQ ID NO:64)), suggesting that libraries with shorter inserts would not have yielded peptides with comparable affinities, or provided equivalent epitope mapping information.

The apparent binding affinities of a subset of the selected peptides were determined using flow cytometric analysis. This method has been shown to enable reliable estimation of both $K_D$ and $k_{diss}$ values. See Daugherty, P. S., et al. (1998) Protein Eng. 11(9):825-832, which is herein incorporated by reference. And importantly, the relative affinity ranking of selected clones obtained using flow cytometry has been shown to be equivalent to that determined using Surface Plasmon Resonance. See Daugherty, P. S., et al. (1998) Protein Eng. 11(9):825-832; and Feldhaus, M. J., et al. (2003) Nat. Biotechnol. 21(2): 163-170, which are herein incorporated by reference. Apparent equilibrium dissociation constants (FIG. 10A) were typically in the low nanomolar range ($K_D$=1-10 nM) (Table A), as determined using fluorescently conjugated CRP and SA. Similarly, the best GP120 binding clones exhibited high fluorescence after incubation with 10 nM GP120, indicating that the $K_D$ is less than about 10 nM (data not shown). Apparent dissociation rate constants ($k_{diss}$) were determined for streptavidin, using about 1 to about 2 µM biotin as a competitor to prevent re-binding.

Rate constants were found to range from about 0.01 $s^{-1}$ after two cycles of MACS and one cycle of FACS (clones SA-7 to SA-11) to about 0.001 $s^{-1}$ after an additional round of screening (clones SA-1 to SA-6). Although the potential avidity effects for surface displayed peptides binding to multimeric target proteins were not ruled out, the dissociation kinetics show excellent agreement with a single exponential decay (FIG. 10B), suggesting about a 1:1 binding stoichiometry. Furthermore, the apparent equilibrium dissociation constant of the best clone ($K_D$=4 nM) is in qualitative agreement with the observed $k_{diss}$ of 0.001 $s^{-1}$, assuming a $k_{assoc}$ value about $5 \times 10^5$ $M^{-1} \cdot s^{-1}$ See Giebel, L. B., et al. (1995) Biochemistry 34(47):15430-15435, which is herein incorporated by reference.

Figure 11:
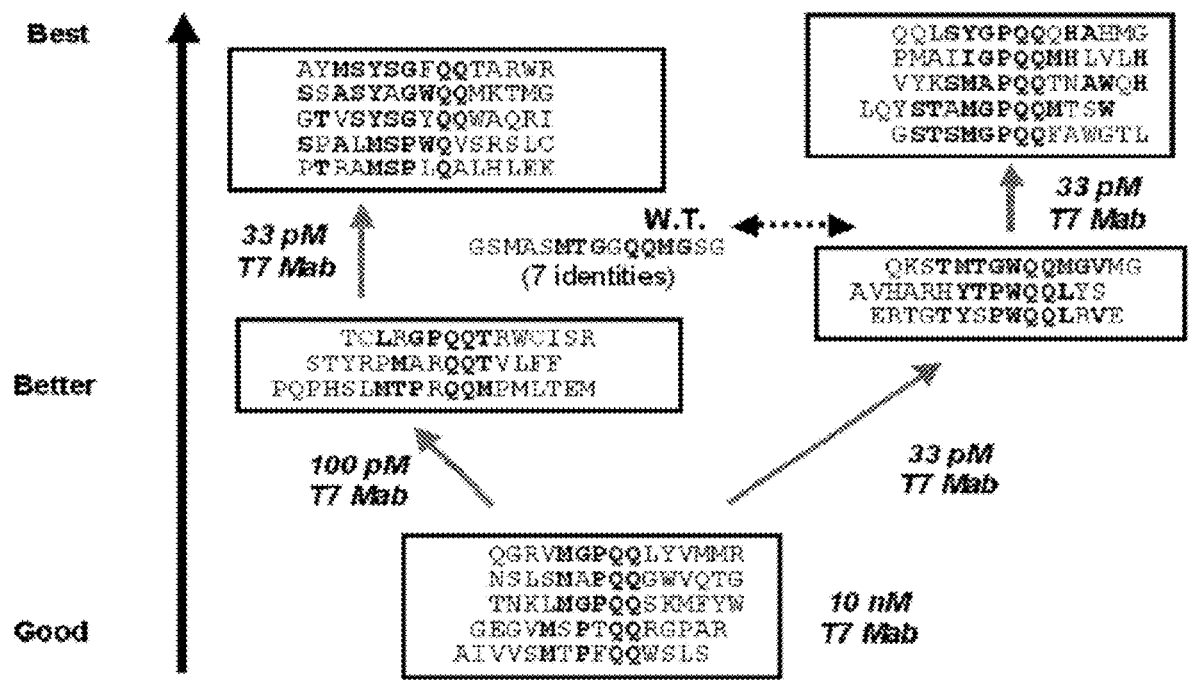
FIG. 11 shows antibody epitope mapping of the antiT7tag antibody. Concentrations indicated are those used for screening using FACS. The sequence identifiers for the top left box are: SEQ ID NO:210, SEQ ID NO:211, SEQ ID NO:212, SEQ ID NO:213, and SEQ ID NO:214; for the top right box are: SEQ ID NO:215, SEQ ID NO:216, SEQ ID NO:217, SEQ ID NO:218, and SEQ ID NO:219; for the middle left box are: SEQ ID NO:220, SEQ ID NO:221, and SEQ ID NO:222; for the middle right box are: SEQ ID NO:223, SEQ ID NO:224, and SEQ ID NO:225; and for the bottom box: SEQ ID NO:226, SEQ ID NO:227, SEQ ID NO:228, SEQ ID NO:229, and SEQ ID NO:230 and the w.t. is SEQ ID NO:231.

Interesting features were observed including (1) a potential disulphide stabilized clone, (2) an extension of the consensus to very rare clones, i.e. the probability of a randomly selected clone having the seven amino acids identical the wild-type is 1 in 5.7 billion. The data also suggest that another round of sorting will further improve the average affinity. The affinity of these clones is higher than wild-type. The highest affinity clones obtained using only 33 pM antigen had up to 7 consensus residues, and an affinity for the T7 antibody 10-fold higher than the wild-type peptide. Thus, the present invention may be used to further optimize antibody peptide interactions. Binding affinities were statistically predictable based upon the antigen concentration used for screening. See FIG. 11. These improved T7 binding peptides may be used as affinity tags for purification and protein detection, and improved epitope detection.

Figure 12A:
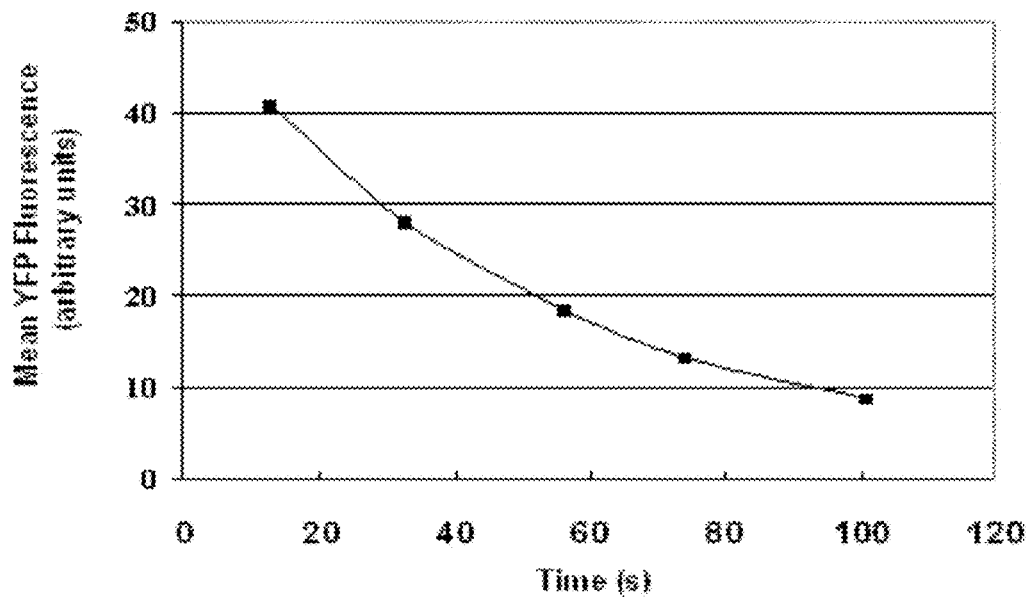
FIGS. 12A and 12B show the measurement of the dissociation rate of streptavidin binding peptide SA-1 grafted into a loop of YFP, on a linear plot (FIG. 12A) or on a semi-log plot (FIG. 12B). Flow cytometry was used to measure the fluorescence of YFP bound to streptavidin coated 1 m beads after the addition of biotin as a competitor.
Figure 12B:
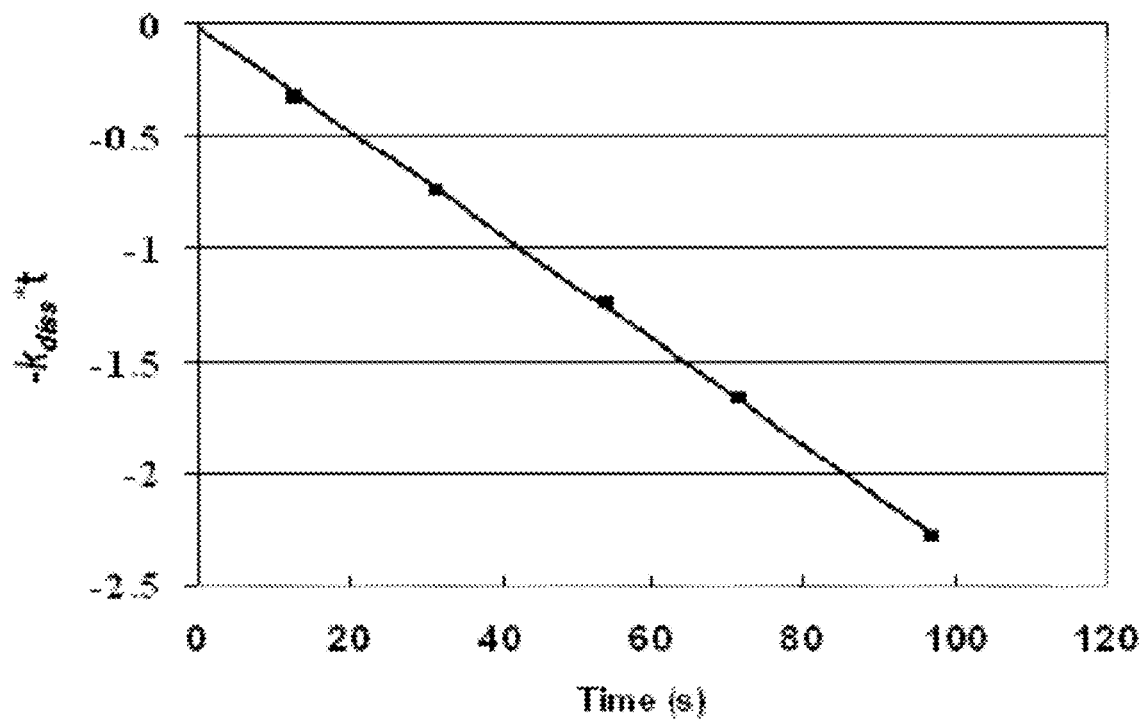

As provided herein, to assess the functional contribution of the OmpA scaffold to high affinity binding, the 15-residue streptavidin binding peptide (SA-1) was genetically inserted into the yellow fluorescent protein immediately following residue Y145. See Baird, G. S. et al. (1999) PNAS USA 96(20): 11241-11246, which is herein incorporated by reference. The fluorescent protein-peptide fusion protein was expressed in soluble form in an engineered *Escherichia coli* strain possessing an oxidizing cytoplasm, for affinity studies. See Bessette, P. H., et al. (1999) PNAS USA 96(24): 13703-13708, which is herein incorporated by reference. This fusion protein retained strong yellow fluorescence comparable to wild-type YFP, and exhibited strong binding to streptavidin-coated polymeric microbeads. Using flow cytometry, the dissociation rate constant of the streptavidin binding fluorescent protein was determined to be 0.02 $s^1$. See FIG. 12. Collectively, these data show that the polypeptides displayed according to the present invention possess high binding affinity, even in the context of scaffolds unrelated to that used for screening.

Since peptides that include a simple consensus motif of the amino acids HPQ have been identified in multiple phage display and mRNA display selections against streptavidin, whether these lower affinity sequences previously identified using phage display would provide detectable affinity in the display systems of the present invention was determined. To enable comparison of the phage and bacterial display peptides, a bacterial display clone was constructed with the insertion, SAECHPQGPPCIEGR (SEQ ID NO:65), and the $K_D$ and $k_{diss}$ were measured in whole cell assays. See FIG. 10A and FIG. 10B. The phage display-derived peptide containing the disulfide constrained HPQ motif was efficiently displayed on bacteria and possessed a dissociation rate ($k_{diss}$) 20-fold faster than that of best peptides isolated using bacterial display (clone SA-1, FIG. 10B). In qualitative agreement with this result, the apparent $K_D$ of the cyclic HPQ clone was five-fold higher than that of the streptavidin binding clone SA-1, confirming the improved affinities of peptides isolated using bacterial display relative to those isolated using phage display.

B. OmpX Expression Vectors

An OmpX loop 2 expression vector and an OmpX loop 3 expression vector similar to the OmpA loop 1 expression vector was constructed. See Example 2 and FIG. 6.

Table 3 provides examples of alternative insertion sites in OmpX and OmpX homologs.

TABLE 3

Sequences suitable for polypeptide display in Gram negative bacteria using E. coli OmpX (FIG. 6) and homologs in other species (preferred insertion locations in bold)

| Organism | Loop 2 Sequence | Loop 3 Sequence |
| --- | --- | --- |
| Escherichia coli | EKSRTASSGDYNKNQY (SEQ ID NO: 66) | KFQTTE--YPTYKNDTSD (SEQ ID NO: 72) |
| Shigella flexneri | EKSRTASSGDYNKNQY (SEQ ID NO: 67) | KFQTTE--YPTYKNDTSD (SEQ ID NO: 73) |
| Salmonella enterica | EKDRTNGAGDYNKGQY (SEQ ID NO: 68) | KFQTTD--YPTYKHDTSD (SEQ ID NO: 74) |
| Klebsiella pneumoniae | EKDNN-SNGTYNKGQY (SEQ ID NO: 69) | KFQNNN--YP-HKSDMSD (SEQ ID NO: 75) |
| Serratia marcescens | EKD-GSQDGFYNKAQY (SEQ ID NO: 70) | KFTTNA-QNGTSRHDTAD (SEQ ID NO: 76) |
| Yersinia pestis | EKSGFGDEAVYNKAQY (SEQ ID NO: 71) | RFTQNESAFVGDKHSTSD (SEQ ID NO: 77) |

Suitable alternative insertion sites may be identified by multiple sequence alignment to identify non-conserved regions and are preferably chosen such that the displayed protein is located more than about 1 nM from the outer membrane of the cell, allowing the displayed polypeptides to interact with arbitrary compositions of matter. See e.g. Table 3.

Other features of the OmpX expression vectors of the present invention are similar or the same as those of the OmpA expression vector above and include (1) the use of the Omp signal sequence, (2) SfiI restriction sites (3) a single resistance gene for a bacteriocidal antibiotic such as chloramphenicol acetyltransferase, (4) a low copy origin of replication such as p15A for low level expression, and (5) a regulatable promoter, such as araBAD promoter, for controlled transcription.

Likewise, the same or substantially similar experiments conducted on the OmpA expression vector described herein were conducted on the OmpX expression vectors with similar results.

C. N/C Terminal Fusion Expression Vectors

Prior to the present invention, polypeptides were most often displayed on cell surfaces either as insertional fusions or "sandwich fusions" into outer membranes or extracellular appendages, e.g., fimbria and flagella fusion proteins or less frequently, as fusions to truncated or hybrid proteins thought to be localized on the cell surface. See Lee, et al. (2003) Trends in Biotech 23(1):45-52; Pallesen, et al., (1995) Microbiology 141:2839; and Etz, et al. (2001) J. Bacteriol. 183(23):6924, which are herein incorporated by reference. Examples of the latter include the Lpp(OmpAaa46-159) system and the ice nucleation protein (InP). See Georgiou, et al. (1997) Nat. Biotech. 15(1):29-34; and Shimazu, et al. (2001) Biotech. Prog. 17(1):76-80, which are herein incorporated by reference.

The outer membrane proteins OmpA, OmpC, OmpF, FhuA, and LamB, have enabled the display of polypeptides as relative short insertional fusions into Omp loops exposed on the extracellular side of the outer membrane. However, the C and N-termini of these carrier proteins are not naturally located on the cell surface which precludes the ability to display polypeptides as terminal fusions. As a result, proteins which are not capable of folding in the insertional fusion context (wherein their C and N termini are fused to the carrier protein sequence), as well as those for which the C and N termini are physically separated in space (e.g., single chain Fv antibody fragments) cannot be displayed effectively as insertions. Similarly, the restriction to the use of insertional fusions, interferes with the display of a large number of proteins from cDNA libraries on the cell surface.

As provided in Example 3 below, the present invention also provides an expression vector for expressing a given polypeptide as an N-terminal fusion protein, a C-terminal fusion protein, or both, i.e., linked or fused directly to a carrier protein present on the external surface of a biological entity, and methods of making and using thereof. As used herein, these expression vectors are referred to as "N/C terminal expression vectors" and include the circularly permuted OmpX (CPX) expression vector exemplified in Example 3.

The N/C terminal fusion expression vectors allow longer polypeptide chains to be displayed on a surface since both termini of the displayed protein are not constrained by insertion. The N/C terminal fusion expression vectors of the present invention enable folding of the carrier protein independently of the passenger polypeptide, since both termini are not constrained. Thus, the N/C terminal fusion expression vectors of the present invention enable surface display of peptides and polypeptides which require a free N or C terminus to fold efficiently, e.g. knottins, and topologically "threaded" folds. See Skerra, A. (2000) J. Mol. Recog. (13):167, which is herein incorporated by reference.

N/C terminal expression vectors of the present invention allow the enhancement of conformational diversity and surface mobility of surface anchored polypeptides. Specifically, the increased mobility of the polypeptide due to its expression as a terminal fusion (as opposed to an insertional fusion), results in a polypeptide having binding affinities and interactions to ligands that is substantially similar to that of the free polypeptide, i.e., the polypeptide in solution. The present invention provides methods for retaining an energetically stable outer membrane protein structure that is compatible with folding, transport, and assembly to allow suitable expression of a given passenger protein as a terminal fusion protein on the cell surface.

In some embodiments, candidate display carrier proteins, e.g., bacterial OMPs, are identified that exhibit the following properties, small (about 50 kD or less, and preferably about 30 kD or less), possess extracellular loops which extend preferably 2 nM or more from the peptidoglycan layer on the cell surface. Insertion points are chosen at the apex of extracellular turns, preferably at sites of poor sequence conservation (high variability) among homologs or paralogs from other species. Residues in the turns of the extracellular loops in consideration with limited phi-psi angle distributions are removed, e.g., proline. A linker is designed, see for example, FIG. 2 and FIG. 13, using flexible amino acids, i.e., glycine or serine.

Figure 4:
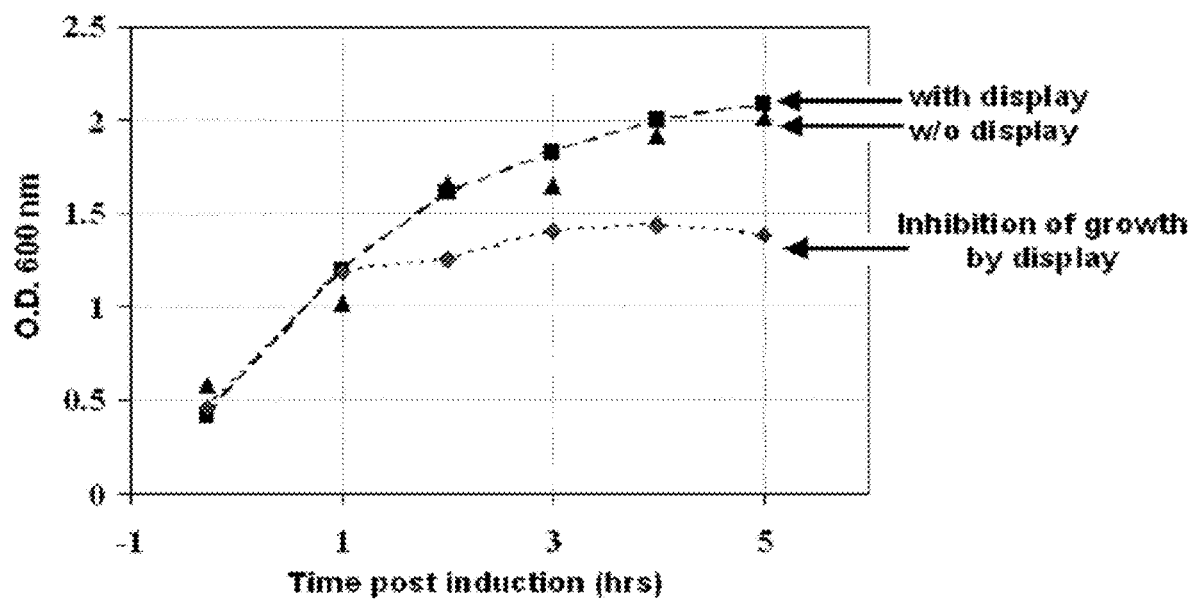
FIG. 4 shows lack of growth inhibition for cells displaying peptides (MC1061/pBAD33L1) as compared to cells not displaying peptides (MC1061/pBAD33OmpA), and cells displaying peptides using MC1061/pBAD18OmpAL1).
Figure 13:
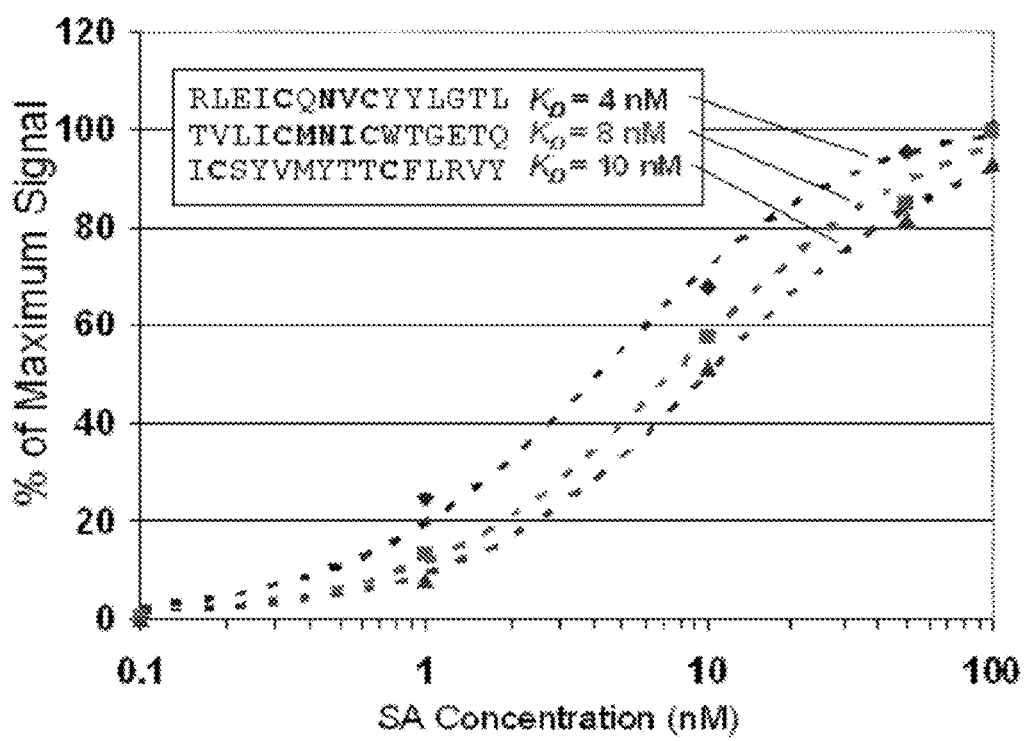
FIG. 13 shows equilibrium dissociation constants for streptavidin binding sequences measured using flow cytometry. The sequence identifiers from top to bottom are SEQ ID NO:232, SEQ ID NO:233, and SEQ ID NO:234.

Using recombinant DNA techniques known in the art, an expression vector is constructed wherein, (1) the carrier polypeptide chain is broken, preferably in the largest extracellular loop protruding maximally from the cell surface, e.g., Loop 2 or 3 of OmpX, (2) the naturally occurring C- and N-termini are fused using a short flexible linker sequence, such as Gly-Gly-Ser-Gly-Gly (SEQ ID NO:78), e.g., FIG. 2 or FIG. 13, (3) a flexible linker is added by fusion to the terminus at which display is desired, e.g., Gly-Gly-Ser-Gly-Gly-Ser (SEQ ID NO:79) the desired protein, i.e., preceding the newly generated N-terminus for N-terminal display or following the new C-terminus for C-terminal display, (4) the passenger peptide or polypeptide (or plurality of sequences, the "library") to be displayed is fused to the linker, e.g., FIG. 2 and FIG. 4, and finally, for N-terminal display, the native signal sequence is identified and fused to the N terminus of the polypeptide to be displayed. With this overall design, primers are designed to amplify gene fragments for assembly, or directly to synthesize (by total gene assembly) the designed sequence. See FIG. 13. The library of assembled genes is digested with a suitable restriction enzyme, ligated into a regulated expression vector, e.g., pBAD18 or pBAD33, and introduced into a host by methods known in the art such as transfection, electroporation, and the like. Plasmid DNA is prepared and multiple frozen stocks are prepared for indefinite storage.

As provided in Example 3, sequence rearrangement of the carrier protein, in this case OmpX, was accomplished using overlap PCR, according to methods known in the art, in order to create N/C terminal fusion expression vectors. See FIG. 14. It should be noted that any protein localized on the outer surface of a biological entity, presenting one or more loop sequences accessible on the cell surface and the like may be modified according to the present invention in order to generate and present a C-terminus, an N-terminus, or both at the outer surface of a biological entity and fused with a passenger polypeptide. Carrier proteins suitable for rearrangement for terminal fusion display from an internal loop include outer membrane proteins, such as OmpA, OmpX, OmpT, OmpC, OmpS, LamB, TraT, IgA protease, and the like, and other extracellular structural adhesion proteins of bacteria, such as FimH, PapA, PapG, and the like, transporter proteins of mammalian cells such as MCAT-1, capsid and coat proteins of bacteriophage (e.g., gpVIII from M13) and the envelope, and capsid proteins of eukaryotic cell viruses (e.g., HIV env, retroviral env, AAV capsid protein), and the like. See e.g. Table 4. Peptide and protein insertion points were chosen to occur within non-conserved loop sequences. The original leader peptide or the like was then fused to the newly generated terminus.

TABLE 4

Representative Carrier Proteins Suitable for Terminal Fusion Display Within Internal Surface Loops

| Biological Entity; Homologs | Carrier Protein; Examples |
|---|---|
| Gram negative bacteria; (e.g. *Escherichia, Yersina,* | Omps; OmpA, C, F, LA, S, T, X, FepA Invasins; Inv, etc; |

TABLE 4-continued

Representative Carrier Proteins Suitable for Terminal Fusion Display Within Internal Surface Loops

| Biological Entity; Homologs | Carrier Protein; Examples |
|---|---|
| *Shigella, Vibrio, Pseudomonas, Salmonella, Enterobacter, Klebsiella,* and the like. | Fimbrial &Pilus Proteins; FimA, FimH, PapA, PapG, F Pilin; Flagella; FliC; S-layer protein; bacteriorhodopsin; bacterial ion channels |
| Gram Positive Bacteria; (e.g. *Staphylococcus, Streptococcus, Bacillus*) | S. protein A (SpA); S-layer protein; M6 protein from *Streptococcus,* etc. |
| Eukaryotic Cell Viruses | Retroviral Envelope proteins; HIV, ALV/MLV, FELV Env viral capsid proteins; AAV Cap, etc. |
| Bacterial Virus & Bacteriophage; M13, fd, T-series phage (T4, T7, and the like), lambda, and the like. | Coat Proteins; GPIII, GPVIII (M13), 10A & 10B (T7 phage) |
| Eukaryotic Cells; Fungal, Animal, Plant | Yeast Cell Wall Proteins; Cwp1p, Tir1p; Sed1p; Tir1p; YCR89W; Mammalian cell alpha helical transporter and ion channel proteins; MCAT-1, MDRs; Adhesion proteins; Integrins, etc. |

Figure 16:
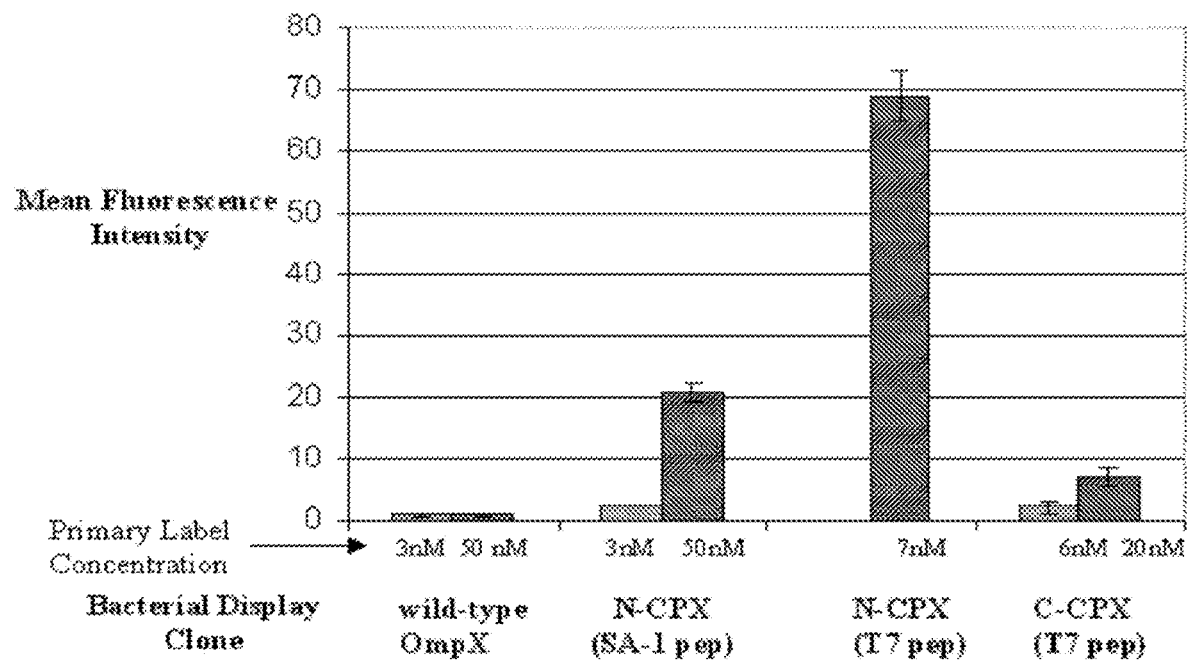
FIG. 16 shows display of disulfide constrained peptides binding to streptavidin (SA-1 pep), or non-constrained peptides binding to the anti-T7 epitope antibody (T7 pep) on the surface of *E. coli* using rearranged OmpX display vector (CPX) resulting in either N terminal display (N-CPX) or C-terminal display (C-CPX) of the passenger polypeptide. Primary label concentration is the concentration of either streptavidin-phycoerythrin, or anti-T7 monoclonal antibody used for fluorescent labeling.

For N-terminal display, the peptide or protein sequence was cloned into a multiple cloning site (MCS) following the leader peptide, preferably immediately following the leader peptide. The DNA sequences encoding the displayed peptide or protein were then fused, via PCR, to DNA sequences encoding a mobile flexible linker of variable length, and preferably about 5 to about 20 amino acids. See FIG. 15 and FIG. 16. The linker C terminus was in turn fused, using overlap PCR, to the newly generated N terminus of the OmpX, for example, residue 54 within loop 2. Preferably, the original C and N terminus (resulting from peptidase cleavage of the leader peptide) were joined via a short flexible linker such as Gly-Gly-Ser-Gly-Gly (SEQ ID NO:78), or the like, i.e. a linker which exhibits substantially similar flexibility and conformational structure as SEQ ID NO:78. See FIG. 15. The C terminus resulting from sequence rearrangement was modified by the addition of one or more stop codons to stop translation using PCR with oligonucleotide primers incorporating two stop codons, using methods known in the art.

Methods of making and using, as well as optimizing, the N/C-terminal expression display systems include those provided above for the OmpA loop 1, OmpX-loop 2, and loop 3 expression vectors as well as those known in the art.

Thus, the present invention provides expression vectors which present or display polypeptides as fusion proteins to an engineered C or N terminus that is displayed on the outer surface of a biological entity. The methods described herein may be applied to other proteins that do not normally present an accessible C or N terminus at the outer surface of a biological entity. This feature enables application of this invention to proteins which are optimally expressed or localized on a biological entity, but which may not possess a surface exposed terminus. For example, the Omps of bacteria, the structural proteins of bacterial fimbria, pili, and flagella, eukaryotic transporter and adhesions proteins. See Table 4. By displaying peptides as terminal fusion proteins rather than as insertional or "sandwich" fusion proteins, the surface displayed peptide affinity properties are more accurately measured in the context of surface display. In other words, the apparent polypeptide-target molecule binding affinity more closely approximates values obtained from measurements of the same interaction in solution with soluble polypeptides. As a result, peptides possessing superior performance can be isolated and identified, and a greater variety of protein sequences can be displayed since one terminus of the protein is not constrained. This approach also allows the display of two-unique polypeptides simultaneously at both the C and N terminus.

Terminal fusion display allows for high mobility of the surface displayed molecule, increased accessibility to target molecules, and simple proteolytic cleavage of the displayed peptide for production of soluble peptides. Terminal fusion display also enables the identification of novel substrates of proteases and peptidases. See FIG. 33. The N/C terminal fusion expression vectors according to the present invention provide a direct way for enhancing the conformational diversity and surface mobility of surface anchored peptides and polypeptides. Through the increased mobility resulting from terminal fusion (as opposed to insertional fusions), the apparent affinity of a polypeptide binding to its corresponding target molecule or material more closely resembles that of the peptide in solution. The N/C terminal display vectors allow the retention of an energetically stable outer membrane protein structure, compatible with folding, transport, and assembly for efficient display of a given passenger protein on the cell surface.

In some embodiments, a cDNA library may be cloned into the display position of the N or C terminal fusion expression vector, with a terminal affinity tag, such as T7tag epitope, or a label, or the like, appended to a terminus of the cDNA clone allowing for measurement of the total display level on the cell surface. As used herein, the term "affinity tag" refers to a biomolecule, such as a polypeptide segment, that can be attached to a second biomolecule to provide for purification or detection of the second biomolecule or provide sites for attachment of the second biomolecule to a substrate. Examples of affinity tags include a poly-histidine tract, protein A (Nilsson et al. (1985) EMBO J. 4:1075; Nilsson et al. (1991) Methods Enzymol. 198:3, glutathione S transferase (Smith and Johnson (1988) Gene 67:31), Glu-Glu affinity tag (Grussenmeyer et al., (1985) PNAS USA 82:7952), substance P, FLAG peptide (Hopp et al. (1988) Biotechnology 6:1204), streptavidin binding peptide, or other antigenic epitope or binding domain, and the like, (Ford et al. (1991) Protein Expression and Purification 2:950), all of which are herein incorporated by reference. As used herein, a "label" is a molecule or atom which can be conjugated to a biomolecule to render the biomolecule or form of the biomolecule, such as a conjugate, detectable or measurable. Examples of labels include chelators, photoactive agents, radioisotopes, fluorescent agents, paramagnetic ions, and the like.

The presence of surface localized cDNAs may be monitored using an antibody or reagent specific for the tag or label according to methods known in the art. Cells binding to a target protein may be then selected using MACS and/or FACS. The library pool may be incubated with a fluorescent label of one color (such as green) and then a second fluorescent label of a second color (such as red) to identify the presence of a full length cDNA of interest. Clones which are red and green are then isolated from the library directly using cell sorting methods known in the art.

In some embodiments, the polypeptides of an N/C terminal fusion expression vector may be isolated or purified from the outer surface of the host. In other words, a polypeptide may be expressed using an N/C terminal fusion expression vector and then produced in a soluble form (free in solution) by introducing a suppressible codon is downstream of the given polypeptide. Alternatively, a protease susceptible linker may be used in place of the "suppressible" codon. The polypeptides are displayed on the surface at high density by induction, such as with arabinose for a period of about 2 hours. The cells are washed once or twice in a compatible buffer, such as PBS, to remove undesired proteins and other debris, the cells are concentrated, and a protease is added to the cell suspension. The proteolytically cleaved polypeptide is then harvested by removal of the bacteria by low-speed centrifugation, and transfer of the supernatant into a fresh tube.

Figure 17:
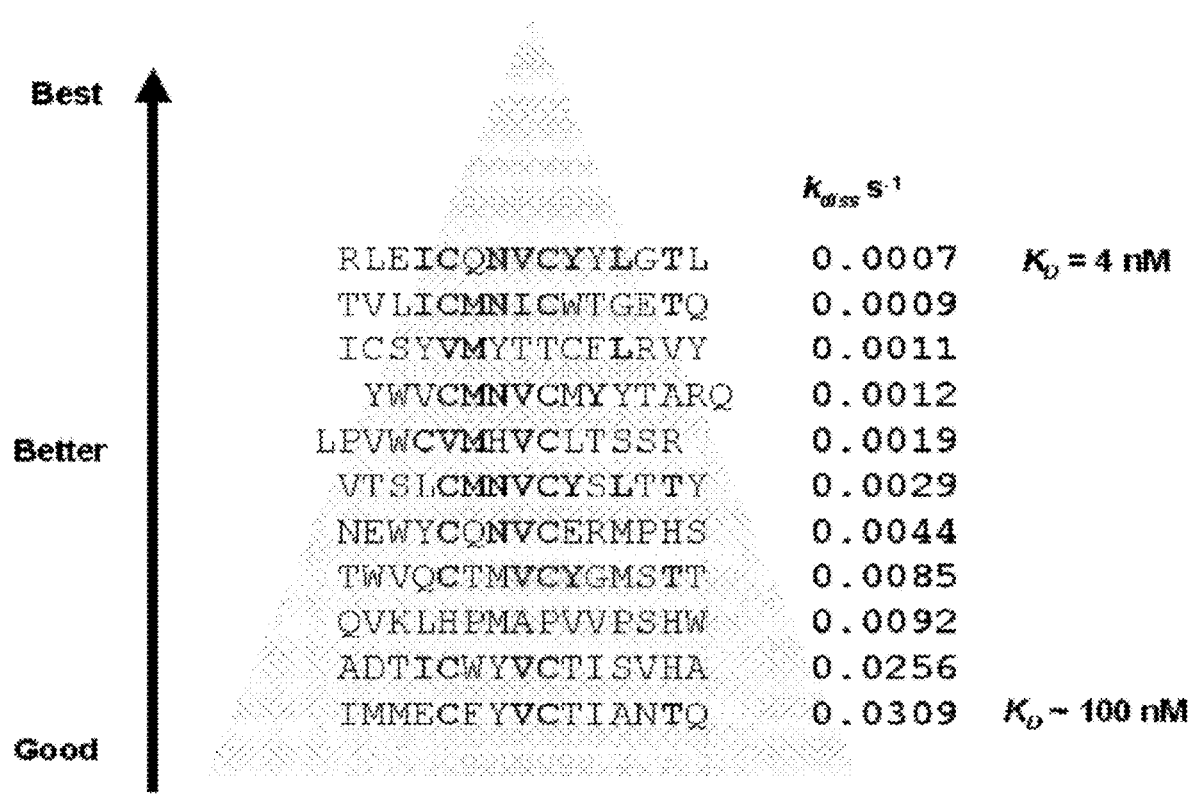
FIG. 17 shows consensus sequences for streptavidin binding peptides isolated from a fully random library displayed in OmpA loop. The sequence identifiers from top to bottom are SEQ ID NOs:235-245.

In some embodiments, the N/C terminal fusion expression vectors of the present invention can be used for the identification of substrates, such as protease and peptidase substrates, from substrate libraries. See FIG. 17. Accordingly, an N/C terminal fusion expression vector may be modified to express a fluorescent protein using methods known in the art. For example, the use of a bicistronic expression vector comprising (1) a circularly permutated outer membrane protein, such as OmpA or OmpX, (2) a ribosomal binding site down stream of the Omp gene sequence, and (3) label such as a green fluorescent protein suitable for efficient detection using fluorescence activated cell sorting, such as alajGFP. Expression is then monitored through the intensity of green fluorescence.

A library of the substrates is created using methods known in the art. The substrates are fused to the N or C terminus of the N or C terminal N/C terminal fusion expression system, respectively. The substrate library is constructed such that a label or an affinity tag suitable for fluorescence labeling is fused to the free terminus of the passenger polypeptide on the cell surface. See FIG. 33. The library is then grown, and cells which are green but not red are removed from the population to eliminate the isolation of false positive clones. The library is then incubated with the enzyme (e.g., a protease or peptidase), and cells which lose red fluorescence while retaining green fluorescence are isolated from the population using FACS.

Figure 18:
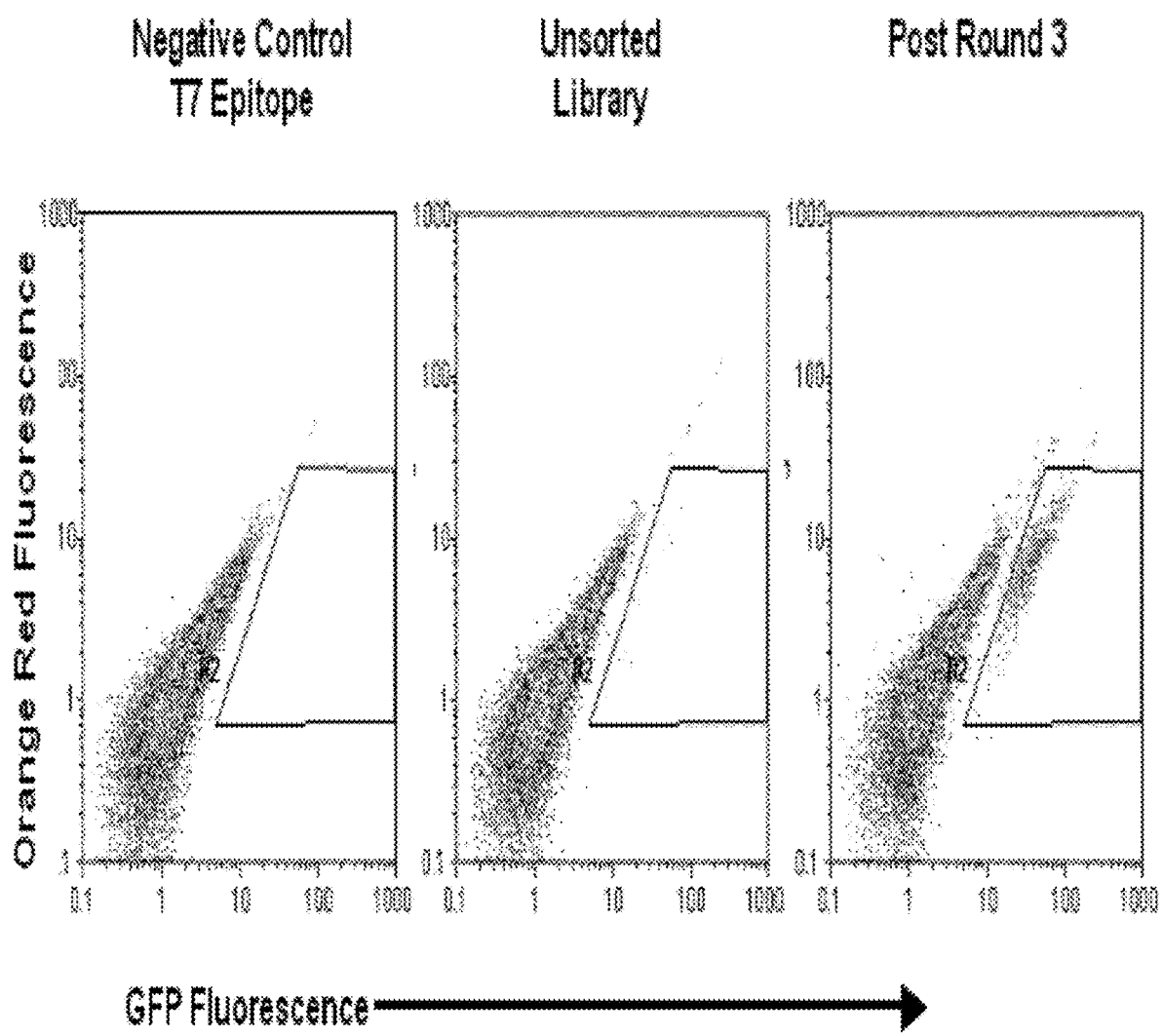
FIG. 18 shows screening of intrinsically fluorescent bacterial display peptide libraries for tumor cell recognition using flow cytometry.

In some embodiments, the N/C-terminal fusion expression vectors of the present invention may be used to construct whole cells that can be used as reagents. For example, one or more peptides identified using the methods herein, binding to a protein, virus, or cellular receptor, or synthetic composition of matter, are displayed on the outer surface of *E. coli* at a desired surface density. Cells can then be coupled directly to a material, e.g., glass/silicon, gold, polymer, by virtue of peptides selected to bind these materials, and used to capture in solution molecules binding to various other displayed peptides on the same cell. For optical detection, cells can co-express a fluorescent or luminescent reporter molecule such GFP, or luciferase. Flow cytometry, or fluorescence microscopy can be used to detect binding of molecular recognition element displaying cells to the target agent, e.g., virus, cell, particle, bead, and the like. See FIG. 18 and FIG. 7.

It should be noted that although the use of bacterial proteins are exemplified herein, a variety of surface localized proteins possessing surface exposed loops may be modified according to the present invention to provide N/C terminal fusion expression vectors which allow the display of polypeptides on the outer surface of viruses, and prokaryotic and eukaryotic cells including phage, bacteria, yeast, and mammalian cells. A variety of surface localized proteins known in the art may be used. In *Escherichia coli* and substantially similar species, such proteins include OmpA, OmpX, OmpT, OmpC, OmpF, OmpN, LamB, FepA, FecA, and other beta-barrel outer membrane proteins. Proteins which exhibit a topology substantially similar to that shown in FIG. 2, i.e., present either a C or N terminus on the outer surface of bacteria, may also be used according to the present invention. One of ordinary skill in the art may readily identify and screen for the various surface localized proteins that may be used in accordance with the present invention.

D. Applications of the Expression Vectors

D1. Selection of Tumor or Tissue/Organ Localizing Bacteria in Living Animals

As provided in Example 4, the library or a given subset of the library according to the present invention may be injected into an animal having a zenografted tumor. After a period of time of a few minutes to several days, tumor or tissue targeting bacteria are isolated by removing the desired tissues/fluids, or tumors from the organism and transferring that sample into bacterial growth medium for bacterial amplification.

Bacterial growth, in vivo, can be monitored using a luciferase operon, autofluorescent protein expression vector, or the like. The amplified bacteria are then used in a substantially similar process to further enrich bacteria for the selected target. Host strains may be modified according to methods known in the art in order to improve selection to reduce host immune response and prevent non-specific binding in vivo. Plasmid DNA is recovered from the isolated bacteria, and the peptide encoding DNA sequence is determined. The identified peptide sequences can then be used alone, or in combination with each other, to target bacteria, gene therapy vectors, and other biopharmaceuticals to tumors in humans.

D2. Immune Response Identification

The display systems of the present invention may be applied to human or animal serum for identifying dominant epitopes to which an immune response is targeted. For example, immune responses may be quantitatively probed in both acquired and genetic diseases, e.g., autoimmune diseases, cancer, viral infections, and the like to identify disease causes, effects, and potential therapeutic intervention points.

In these embodiments, immunoglobulin (IgG) or other protein fractions may be purified from a test sample, such as serum, spinal fluid, or other body fluids, and labeled with biotin. This biotinylated mixture of different IgGs can then be used as antigens to select and screen for peptides or proteins recognized by a corresponding antibody in the antigen mixture. After enrichment of the biological entity displaying antibody binding moieties, individual clones are isolated from the mixture by plating, their sequences are determined by DNA sequencing. The resulting sequences would fall into distinct consensus groups that correspond to different antibody specificities highly represented in the mixture. See e.g. FIG. 11, FIG. 19, and FIG. 20. By performing multiple selections with the antibody mixture over a range of total antigen concentrations, e.g., about 0.1 to about 100 nM, different consensus sequences would emerge. The peptide sequence selected from the library isolated would, in many cases, be substantially similar or the same to a corresponding sequence present on a native protein surface. In other words, the display selection would allow identification of the proteins with which the antibodies in the mixture bind to, thereby providing a target for therapeutic intervention.

The following examples are intended to illustrate but not to limit the invention.

Example 1

OmpA Loop 1 Expression Vector

A 15-mer random insert sequence which provides a balance between sequence complexity and maintenance of the stability and folding and export of OmpA was selected. See FIG. 2. It should be noted that longer length insert, e.g., 15 mer, libraries provide more copies of short sequences while allowing for possible longer cell binding motifs requiring 10 or more amino acids. Although an engineered disulphide bridge may be used for stabilization, such was not used as cystein oxidation in the E. coli periplasm could lead to aggregation and reduced export and disulfides could potentially emerge by chance. Moreover, the membrane spanning domain of OmpA already provides a rigid structural anchor for the peptide inserts into the more flexible loops.

After optimizing the library construction process through the use of the pBAB33L1, construction of a high quality library of about $4.5 \times 10^{10}$ independent transformants was found to be possible. This library is believed to be larger than any other reported bacterial display library, although a few similar sized phage libraries have been constructed. See Vaughan, T. J., et al. (1996) Nature Biotech. 14(3):309-314, which is herein incorporated by reference. This fact is notable since library size has previously been shown to correlate with the quality (affinity and specificity) of the selected sequences. See Griffiths, A. D. and D. S. Tawfik (2000) Curr. Opin. Biotechnol. 11(4):338-353, which is herein incorporated by reference. For optimal selection and screening efficiency, expression, growth, and induction conditions, as well as promoter strength and insert location were optimized. See FIG. 4. Importantly, a tightly-regulatable promoter was used to prevent loss of mildly toxic sequences during growth, maintain full library diversity, and improve single round enrichment efficiency. See FIG. 5.

A. Bacterial Strains, Vectors and Plasmids

All work was performed in E. coli strain MC1061 (F$^-$ araD139 $\Delta$(ara-leu)7696 galE15 galK16 $\Delta$(lac)X74 rpsL (Str$^R$) hsdR2 ($r_K^- m_K^+$) mcrA mcrB1), with the exception of YFP expression, which was carried out in FA13. See Bessette, P. H., et al., (1999) PNAS USA 96(24):13703-13849; and Casadaban, M. J. and S. N. Cohen, (1980) J. Mol. Biol. 138(2):179-207, which are herein incorporated by reference. Primers were obtained from Integrated DNA Technology (Coralville, Iowa), Operon-Qiagen (Valencia, Calif.), and Invitrogen (Carlsbad, Calif.). Restriction enzymes were from New England BioLabs (Beverly, Mass.). Streptavidin, R-phycoerythrin conjugate was purchased from Molecular Probes (Eugene, Oreg.). Biotinylated, and HRP conjugate, anti-T7•tag monoclonal antibody was obtained from Novagen (Madison, Wis.). Streptavidin coated magnetic microbeads were obtained from Qiagen (Valencia, Calif.), Dynal (Brown Deer, Wis.), or Miltenyi Biotec (Auburn, Calif.). Anti-biotin mAb coated magnetic beads and anti-biotin mAb R-phycoerythrin were from Miltenyi Biotec (Auburn, Calif.). Biotinylation and fluorescent labeling with Alexa Fluor® 488 were carried out using the FluoReporter® Mini-biotin-XX Protein Labeling Kit and Alexa Fluor® 488 Monoclonal Antibody Labeling Kit, respectively, from Molecular Probes (Eugene, Oreg.). Human C-reactive protein (cat#C4063) and serum albumin (cat# A3782) were from Sigma (St. Louis, Mo.). Biotinylated HIV-1 gp120 was obtained from ImmunoDiagnostics (Woburn, Mass.).

B. Vector and Library Construction

To maximize library construction efficiency, asymmetric SfiI restriction sites were introduced into an OmpA expression vector immediately preceding loop 1 and following loop 4. DNA fragments containing the random epitope insertions were synthesized by PCR, digested with SfiI, ligated into the display vector, and transformed into the *E. coli* strain MC1061, which can be made highly transformation competent and is ara-, allowing the use of the araBAD promoter for controlled OmpA expression. See Sidhu, S. S. (2000) Curr. Opin. Biotechnol. 11(6):610-616, which is herein incorporated by reference.

Plasmid pB33OmpA, contains the wild type ompA gene, including the native RBS, inserted downstream of the araBAD promoter in plasmid pBAD33. See Guzman, L., et al., (1995) J. Bacteriol. 177(14):4121-4130, which is herein incorporated by reference. It was constructed by ligation of digested (KpnI/HindIII) pBAD33 with a similarly digested ompA gene PCR product obtained using MC1061-derived genomic DNA, and primers 1 and 2. See Table 5.

N25G, N26Q and H151G, T152Q, T155Q. Plasmid pB33OmpA14 was made via overlap PCR, using primers 1-4 (Table 5) with pB33OmpA as template. The overlap product was digested (KpnJ/HindIII) and ligated to similarly digested pBAD33. Plasmids pB33OT1 and pB33OT4 containing the T7•tag epitope inserted into loops 1 and 4, respectively, of OmpA were constructed using PCR, with pB33OmpA as template, and primer 5 or 6 (Table 5), respectively, with primers 1 and 2 (Table 5). The overlap products were digested with SfiI and ligated with SfiI digested pB33OOmpA14. Plasmid pB330S1, containing the streptavidin-binding peptide sequence SAECHPQGPP-CIEGR (SEQ ID NO:96), inserted into OmpA loop 1, was constructed by overlap PCR using primers 1, 2, 7, and 8 (Table 5) with pB33OmpA14 as template. See Giebel, L. B., et al (1995) Biochemistry 34(47):15430-15435, which is herein incorporated by reference. Products were digested with SfiI and ligated into digested pB33OmpA14.

For random 15-mer library construction, primers 9 and 10 (Table 5) were used in a PCR with pB33OmpA as the

TABLE 5

Oligonucleotide primers used in polymerase chain reactions to construct expression plasmids and libraries*

| Primer | |
|---|---|
| 1 | GAGTCCAGAGGTACCAACGAGGCGCAAAAAATGAAAAAGACAGCT (SEQ ID NO: 80) |
| 2 | CGTTATGTCAAGCTTTTAAGCCTGCGGCTGAGTTA (SEQ ID NO: 81) |
| 3 | CAGTACCATGACACTGGCCTCATCGGCCAAAATGGTCCGACCCAT (SEQ ID NO: 82) |
| 4 | AACATCGGTGACGCAGGCCAGATCGGCCAGCGTCCGGACAACGGC (SEQ ID NO: 83) |
| 5 | CGTCCTGGCCTCATCGGCCAAGGATCCATGGCCTCCATGACCGGAGGACAACAAATG GGATCCGGAAATGGTCCGACCCATGAAAACCAACTGGGC (SEQ ID NO: 84) |
| 6 | CGTCATCTGGCCGATCTGGCCTCCGGATCCCATTTGTTGTCCTCCGGTCATGGAGGC CATGGATCCTGCGTCACCGATGTTGTTGGTCCACTGGTA (SEQ ID NO: 85) |
| 7 | CATCCGCAGGGCCCGCCGTGCATTGAAGGCCGCAATGGTCCGACCCATGAAAAC (SEQ ID NO: 86) |
| 8 | GCACGGCGGGCCCTGCGGATGGCATTCCGCGCTTTGGCCGATGAGGCCAGTGT (SEQ ID NO: 87) |
| 9 | CGTCCTGGCCTCATCGGCCAA (NNS)₁₅AATGGTCCGACCCATGAAAACCAACTGGGC (SEQ ID NO: 88) |
| 10 | CGTCATCTGGCCGATCTGGCCTGCGTCACCGATGTTGTTGGTCCACTGGTA (SEQ ID NO: 89) |
| 11 | ACTGTTTCTCCATACCCGTTTTTTTGGGCTAGCGAATTCCGTCCTGGCCTCATCGGC CAA (SEQ ID NO: 90) |
| 12 | GGCTGAAAATCTTCTCTCATCCGCCAAAACAGCCAAGCCGTCATCTGGCCGATCTGG CCT (SEQ ID NO: 91) |
| 13 | TCGCAACTCTCTACTGTTTC (SEQ ID NO: 92) |
| 14 | GGCTGAAAATCTTCTCTC (SEQ ID NO: 93) |
| 15 | TAGTAGCAAACGTTCTGGCAGATCTCCAAGCGTTCAATGTTGTCTCTAATTT (SEQ ID NO: 94) |
| 16 | TGCCAGAACGTTTGCTACTACCTCGGGACGCTCGATGGTTCTGTTCAATTAGC (SEQ ID NO: 95) |

*N = A, C, G, T; S = C, G

The plasmid pB33OmpAL4 contains addition of SfiI restriction sites in the ompA gene at positions corresponding to the beginning of the first extracellular loop of OmpA and at the end of the fourth loop, resulting in mutations F23L, template. The resulting product was lengthened in a second PCR to enable efficient digestion, using primers 11 and 12 (Table 5). The product was then digested (SfiI) and inserted into the digested (HincI/SfiI) pB33OmpA14 vector. About 15 μg of ligated DNA was transformed to the strain MC1061 by electroporation in ten aliquots. Transformed cells were pooled and incubated for 1 hour in 30 ml SOC medium. Serial dilutions were plated onto LB plates with 32 μg/ml chloramphenicol to determine library size. The transformed cells were cultured in 500 ml of LB medium with 0.2% glucose and 32 μg/ml chloramphenicol and grown to an OD of 2.2. Plating of serial dilutions of the pooled transformation mixture indicated $5 \times 10^{10}$ independent transformants.

The fusion protein expression plasmid encoding a yellow fluorescent protein incorporating a peptide insertion binding to streptavidin, pB33YFP-SA, was constructed by overlap extension PCR with an Aquorea GFP-based yellow fluorescent protein gene as template with primers 13-16 (Table 5), resulting in insertion of the 15 amino acid SA-1 peptide in the permissive site between amino acids Y145 and N146 of YFP. See Baird, G. S., et al. (1999) PNAS USA 96(20): 11241-11246, which is herein incorporated by reference.

A library aliquot was placed into appropriate bacterial growth medium containing more than about 0.1% glucose and propagated overnight for about 6 to about 12 hours. The library was then diluted into fresh growth medium at a factor of about 1:50 to about 1:100 and grown until the culture density (OD 600) reaches an OD value of about 0.5 to about 1.0, and expression of the library elements to be display was initiated by the addition of arabinose to the culture. The culture was then propagated further for about 0.1 to about 3 hours depending on the desired surface concentration of the library element to be displayed. In screening random peptide libraries displayed in OmpA-L1, an induction time period of about 30 minutes to about 2 hours is preferred. Shorter periods provided increased selection pressure for monovalent binding interactions, and consequently high affinity binding moieties.

An aliquot of the culture containing more than about $2 \times 10^{11}$ bacterial cells was then taken, washed in PBS, and resuspended in PBS at an OD of about 1 to about 10. The library was then mixed with one or more ligands, e.g. a protein, which has been chemically coupled to biotin, and allowed to incubate with gentle mixing, e.g., inversion or rocking, for a period of about 1 hour. The unbound ligand was then removed by washing about 1 to about 2 times in PBS. Streptavidin coated paramagnetic beads of about 10 nm to about 1 m or a streptavidin conjugated fluorescent probe were then added allowing the labeled cells to attach to the magnetic particles.

C. Magnetic Selection

Figure 21:
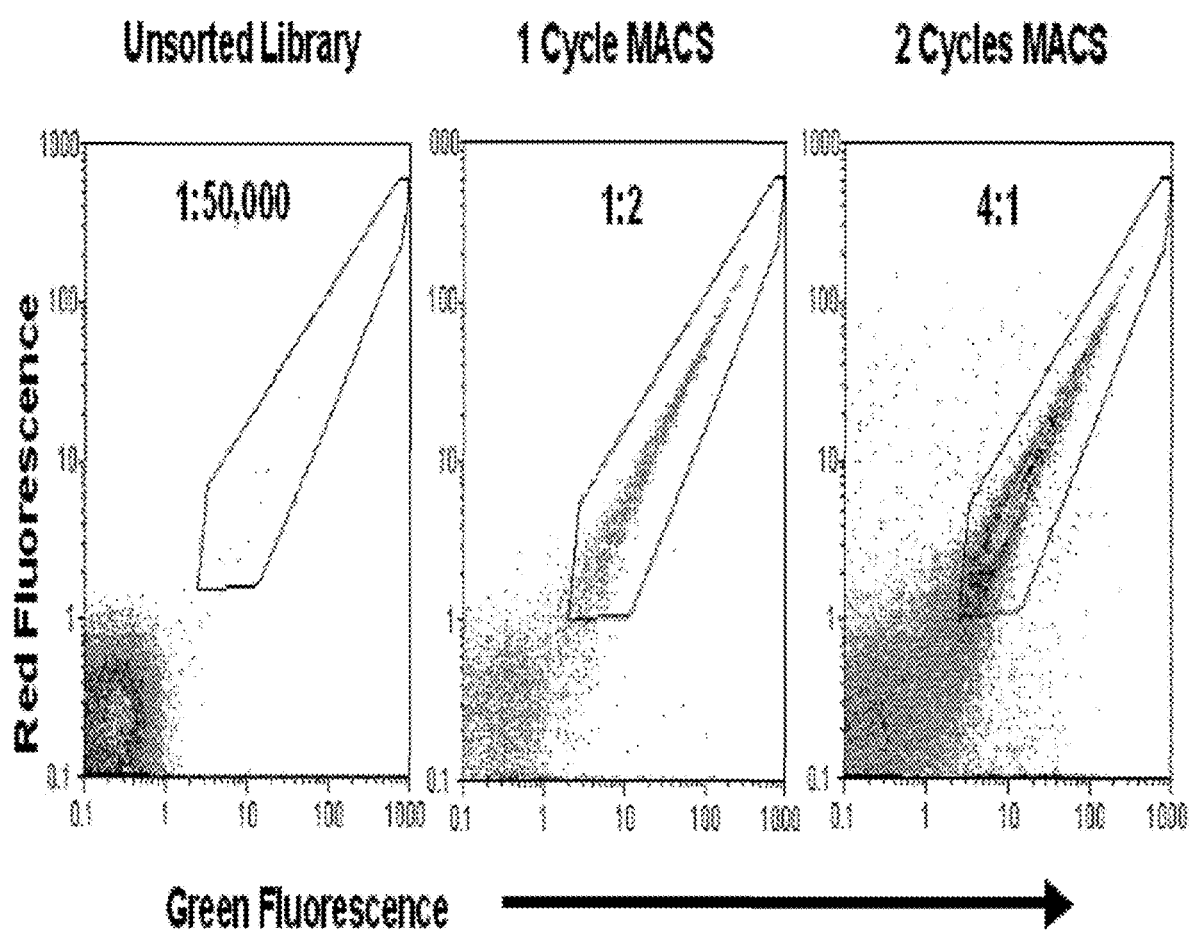
FIG. 21 shows flow cytometric analysis of the OmpA 15mer library prior to selection (Unsorted Library) and populations resulting from one or two rounds of magnetic selection (MACS) for binding to a T7tag antibody.

Cell displaying the given polypeptide were then separated from those that do not by sequential application of an enrichment cycle by applying a magnet of significant strength to the exterior face of the container holding the library, in order to remove specifically labeled cells from the mixture. See FIG. 21. Cells not adhering to the magnetic particles were then removed from the container and discarded if not of interest. The magnet was then removed and a sterile buffer was added to the container, and the cells and magnetic particles were thoroughly resuspended using methods known in the art.

The previous two steps were then repeated about 2 to about 5 times depending upon the expected value of the dissociation constant of the isolated clones. For the first round of selection from a random library 2 washes were sufficient unless it was known that the library contains many sequences that bind to the target. In each successive cycle, about 10 to about 1000-fold fewer cells were used for selection and the target ligand concentration (if soluble) was reduced by some factor greater than two, e.g., 10 fold. The ideal number of enrichment cycles is determined by the cycle after which no change in the number of fluorescent events is observed. For example in selection for binding to HSA, the frequency of cells binding to FITC-conjugated HSA increased after the first round to about 0.6%, and after the second round to about 10%, and then remained roughly constant at about 10% after the third round indicated that no further rounds of enrichment should be performed.

Figure 22:
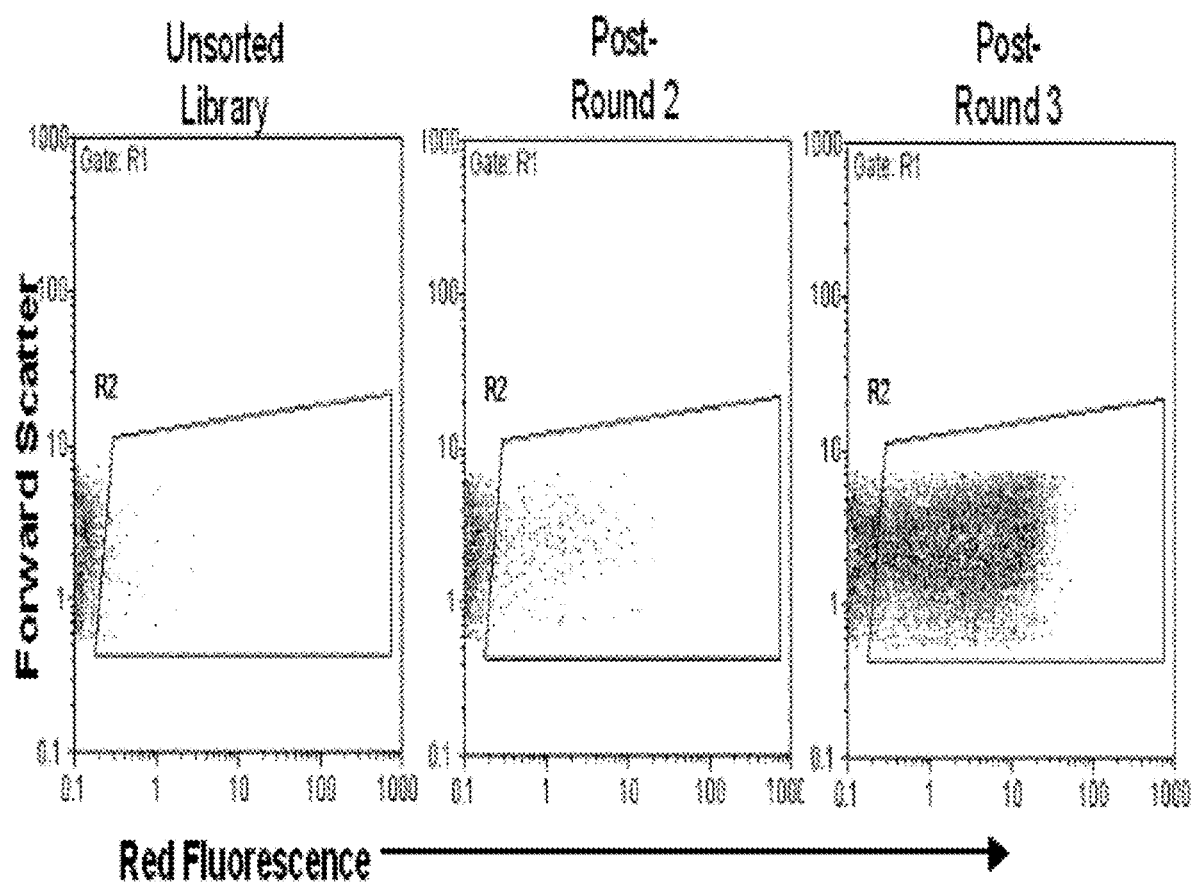
FIG. 22 shows enrichment of CRP binding peptides by magnetic selection, as measured by flow cytometry.

After the final wash, a small volume of the sample was diluted to about 1:1000 and plated onto agar plates to determine the number of clones remaining after this enrichment cycle. The remaining volume was transferred into a bacterial culture vessel, e.g., 250 ml culture flask, containing suitable growth medium, antibiotics, and glucose. The cells were propagated until they reached a density of about 0.5 OD or greater, and preferable not more than about 2 hours after the cells reach stationary phase (where the culture OD is not changing). Cell were then relabeled with biotinylated target, and streptavidin phycoerythrin or the like, and analyzed by flow cytometry to determine enrichment. See FIG. 21 and FIG. 22.

D. Flow Cytometric Screening

Flow cytometric screening of the magnetically enriched library population was used to achieve a more precise separation of only the tightest binding peptides. The enriched pool from magnetic selection was screened using flow cytometry for highly fluorescent cells after incubation with a biotinylated-T7 antibody (at a final concentration of 100 pM), and then streptavidin-phycoerythrin in order to assess the efficiency of selection of peptide ligands. See FIG. 21. Randomly selected clones from the sorted population were then sequenced. See FIG. 11.

For flow cytometric analysis and sorting, induced cells were typically labeled with biotinylated or fluorescently labeled antigen in PBS on ice for about 45 to about 60 minutes, followed by centrifugation and removal of the supernatant. When using biotinylated antigens, a secondary labeling was carried out with 6 nM streptavidin-phycoerythrin (Molecular Probes, Eugene, Oreg.) or 1 nM anti-biotin mAb-phycoerythrin (Miltenyi Biotec, Auburn, Calif.) for 30 minutes on ice, followed by centrifugation and removal of the supernatant. Cells were then resuspended in cold PBS at about $10^6$ cells/ml and immediately analyzed on a Partec PAS III cytometer (Partec Inc., Muenster, Germany) equipped with a 100 mW argon (488 nm) laser. For analysis, about $10^4$ to about $10^6$ cells were interrogated, and for sorting, at least 10-fold oversampling of the expected clonal diversity was used. Following sorting, retained cells were either amplified for further rounds of analysis and/or sorting by growing overnight in medium containing glucose, or plated directly on agar for isolation of single clones. Typically, about 5 to about 15 selected clones were confirmed for antigen binding, and the identity of each peptide insert was determined by automated sequencing of the ompA gene contained on the isolated plasmid.

Generally, for the first round of magnetic selection, a frozen aliquot of about $2.5 \times 10^{11}$ cells was used to inoculate 500 ml of LB medium containing 25 μg/ml chloramphenicol and grown at 37° C. with shaking (250 rpm) until the $OD_{600}$ was about 1 to about 1.5, at which time L-arabinose was added to a final concentration of 0.02% (w/v). After an additional two hours of growth, a volume corresponding to about $2.5 \times 10^{11}$ cells was concentrated by centrifugation (2000×g, 4° C., 15 minutes) and resuspended in 15 ml of cold PBS.

For negative selection, 150 μl of streptavidin-coated magnetic beads (Qiagen, Valencia, Calif.) were added, and the cell/bead mixture was incubated on ice for 30 minutes, at which time a magnet was applied to the tube, and the unbound cells in the supernatant were removed to a new tube.

For positive selection, biotinylated antigen (about 1 to about 100 nM) was added to the supernatant fraction and incubated on ice for about 30 about 60 minutes. Cells were centrifuged as above and resuspended in 7.5 ml of cold PBS with 150 µl of streptavidin-coated magnetic particles (Qiagen, Valencia, Calif., or Miltenyi Biotec, Auburn, Calif.). After about 30 to about 60 minutes of incubating the cells on ice with periodic agitation, a magnet was applied to the tube, and the supernatant was removed and discarded. The pellet was washed twice in 7.5 ml of cold PBS, repelleted to the magnet each time, and finally resuspended in LB medium and grown up overnight at 37° C. with shaking in 20 ml of LB with chloramphenicol and 0.2% glucose.

For the subsequent rounds of selection or sorting, a volume of cells corresponding to at least 10-fold oversampling of the number of cells retained in the previous round was subcultured to fresh LB with chloramphenicol but without glucose, grown to mid-log phase, and induced as above. The volumes used for magnetic selection were reduced, while maintaining the same concentrations. In some cases, subsequent rounds of magnetic selection were carried out with anti-biotin mAb coated magnetic particles (Miltenyi Biotec, Auburn, Calif.).

In one round, the population was enriched to roughly 50% binding peptides from an initial frequency of about $1:10^5$ (about 50,000-fold enrichment). A single round of screening required only about two hours of labor followed by overnight growth to amplify selected sequences. DNA sequencing of eight randomly chosen clones after two rounds of magnetic selection revealed a strong consensus binding motif of MAPQQ (SEQ ID NO:97) or MGPQQ (SEQ ID NO:98) that conferred high affinity ($K_D$–1 nM) binding to the T7 antibody as determined using an equilibrium binding affinity assay. See e.g. FIG. 17. In contrast, about 12-mer to about 20-mer phage display libraries rarely yield consensus sequences, likely due to uneven amplification of selected sequences after each round of selection. See Barry, M A., et al. (2002) VECTOR TARGETING FOR THERAPEUTIC GENE DELIVERY. Wiley-Liss; and Daugherty, et al. (1999) Protein Engineering. 12(7):613, which are herein incorporated by reference. Significantly, whole cell assays can be performed directly using selected clones to determine both dissociation rate constants and equilibrium affinity values of the peptide-target interaction. See FIG. 11 and Daugherty, et al. (1999) Protein Engineering. 12(7):613, which is herein incorporated by reference.

The relative affinity of selected clones was rank ordered using either equilibrium dissociation constant measurements in the whole cell format or dissociation rate constant measurements described herein. See FIG. 13 and FIG. 17.

For selection of peptides that bind to cell surface receptors which either do or do not become internalized, the library was mixed with a population of the target cells with the target cells in excess. See FIG. 1 and FIG. 18. The target cells were then removed from the added bacterial library either using immunochemical methods, chromatographic methods, or centrifugation, and the process was repeated.

Alternatively, the library was constructed in a host cell that expresses an autofluorescent protein optimized for flow cytometric detection, e.g., alajGFP. The fluorescent protein allows cell which are either attached or internalized into bacteria to be detected simply by flow cytometry or fluorescence microscopy. See FIG. 18 and FIG. 21. As result expensive reagents are not required to detect the presence of the binding event. The bacterial display library, exhibiting intracellular GFP, is then is mixed with the target cell population, and target cells that exhibit green fluorescence after a short incubation of about 1 minute to a few hours, and after an optional wash step are directed sorted from the population.

Figure 23:
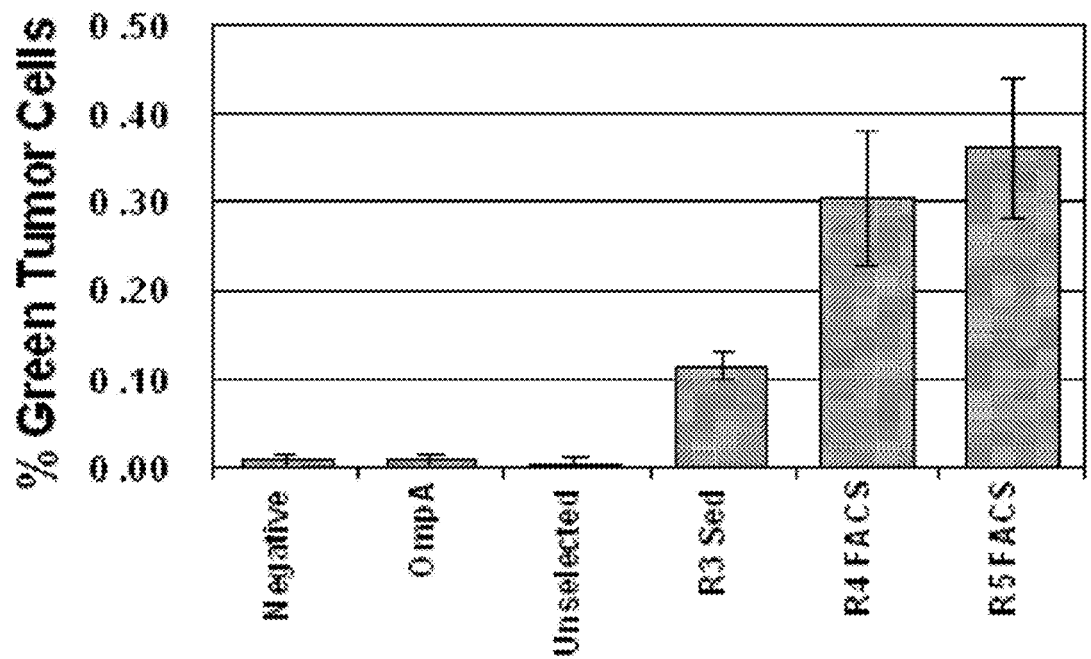
FIG. 23 shows enrichment of tumor binding and internalizing bacteria using FACS.

Bacteria were then recovered by transfer of the target cells with attached bacteria into bacterial growth medium. For selection of internalizing ligands, cells were treated with a drug or selective agent, e.g. lysozyme, which kills extracellular bacterial. Intracellular bacteria were then recovered by diluting the target cells into water to lyse the target cells, and release the bacteria. Sequential application of this process results in sequences which either bind to a target cell, or bind and become internalized into the target cell. See FIG. 20 and FIG. 23.

E. Protein Epitope Mapping

In many circumstances it is desirable to determine the proteins and protein sites to which another protein binds, or to map a protein binding epitope. To demonstrate that the present invention may be used for (1) isolating protein binding peptides, and (2) determining protein sequences to which a chosen protein binds, a protein mapping experiment was performed as follows.

The library was first depleted of streptavidin binding peptides by incubation with streptavidin coated microbeads, e.g., from Qiagen, Inc. (Valencia, Calif.). Then the library was incubated with biotinylated human C-reactive protein at 10 nM final concentration, and two rounds of magnetic selection were used to enrich CRP binding peptides. See FIG. 22. Three rounds of MACS resulted in a population comprising more than about 50% binding clones using 10 nM antigen. The enriched population was then labeled with 100 pM CRP and cells exhibiting fluorescence above background autofluorescence were sorted using FACS. One round of sorting enriched several clones exhibiting very high affinity for CRP, including one clone, EWACNDRGFNCQLQR (SEQ ID NO:99), which was determined to be a cyclic peptide with an affinity of $K_D$=1.2 nM. See FIG. 19. Two different consensus sequences were obtained, a result which has very rarely been observed using other display technologies. Equilibrium binding affinities were measured in the whole cell format, by determining cell fluorescence at various concentrations of target CRP. See e.g. FIG. 17. CRP binding clones are likely to be useful as inexpensive diagnostic reagents.

F. Selection of High Affinity Protein Binding Peptides Using Kinetic Selection

Figure 24:
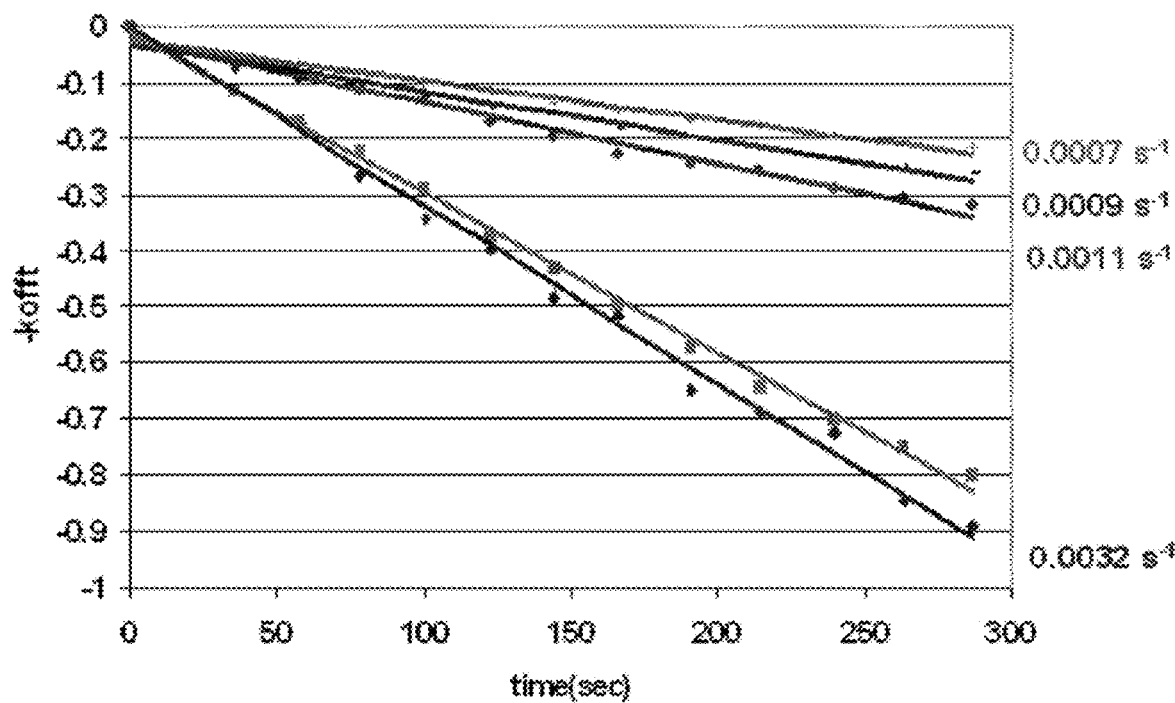
FIG. 24 shows dissociation rate constants of streptavidin binding peptides display on *E. coli*, measured by flow cytometry.

The library was incubated with a 1:1 mixture of streptavidin coated nano-spheres (50 nM) and streptavidin coated microparticles (Qiagen, Valencia, Calif.). Magnetic selection was used to separate binding clones from non-binding clones. Two rounds of selection provided a population of more than about 25% streptavidin binding cells. The enriched population was then labeled with streptavidin at 1 nM concentration, washed 1× in PBS, and then resuspended in PBS with 100 µM biotin as a competitor. This process step is used to favor clones with slow dissociation rate constants. After 1 hour, cells retaining detectable fluorescence were sorted using FACS. Individual clones were isolated by plating on agar plates and picking colonies after overnight growth. Clones from both magnetic selection and magnetic selection+FACS were sequenced, and their dissociation rate constants were measured using flow cytometry. See FIG. 24. The dissociation rate, and equilibrium dissociation constants were measured using flow cytometry. See FIG. 13 and FIG.

17. The highest affinity clone had an affinity of 4 nM and a dissociation rate constant of 0.0007 s$^{-1}$. The sequence function data can be used to establish sequence function relationships.

G. Selection of HSA and gp120 Binding Peptides

Figure 25A:
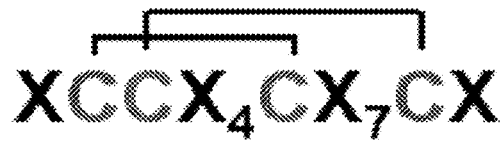
FIG. 25A shows streptavidin binding peptides selected from a double constrained library, (XCCX$_4$CX$_7$CX) comprising about 1×10$^9$ unique clones displayed in loop 2 of OmpX. The sequence identifiers from top to bottom are SEQ ID NOs:267-275.
Figure 25B:
FIG. 25B shows streptavidin binding peptides selected from a X$_4$CX$_3$CX$_4$ library displayed in loop 2 of OmpX. The sequence identifiers from top to bottom are SEQ ID NOs: 276-284.

The above process was applied to isolated peptides that bind to HIV-1 gp120 (as potential viral entry inhibitors) and to human serum albumin for determining feasibility of drug delivery and purification applications. See Sato, A. K., et al. (2002) Biotechnol. Prog. 18(2):182-192, which is herein incorporated by reference. Examples of selected peptides are shown in FIG. 25 and FIG. 26. The affinities of peptides isolated using the methods of the present invention are found to be significantly higher than affinities of peptides isolated using phage display for identical targets. See Table 6.

TABLE 6

Equilibrium dissociation constants for peptides selected from

| Target Protein | $K_D$(nM) |
|---|---|
| T7 MAb | 0.3 |
| C-RP | 1.2 |
| SA | 4 |
| HSA | 100 |
| GP120 | 2 |

The present invention allows the identification of optimal cystein placements to form disulphide constrained loops conferring high binding affinity without explicit library design, thereby alleviating the need to construct and screen ten or more different libraries, and removing critical assumptions that have limited the affinities of isolated ligands in earlier studies. See e.g. Giebel, L. B., et al. (1995) Biochemistry 34(47):15430-15435, which is herein incorporated by reference. For example, selections for binding to streptavidin yielded a strong preference for CX$_3$C ligands in all rounds of selection. Though several reports have previously described the screening of both linear and disulphide constrained peptide libraries (with differing lengths), the generation and screening of a CX$_3$C type library using any reported display technology has not been described previously.

Since loop rigidity has been shown to correlate with binding affinity, the additional rigidity imparted by the more tightly constrained loop appears to benefit affinity. It appears likely that phage display selections using "built-in" three-residue turns might yield affinity improvements relative to previously selections. While the results with streptavidin were expected, peptides containing putative disulphide loops were present in peptides binding to each of the target ligands tested (T7 antibody, HSA, gp120, and CRP) despite a 1000-fold reduced probability of occurrence. While a strong consensus sequence of IXNXRGF (SEQ ID NO: 100) was present in clones from the selection for CRP binding, FACS screening of the enriched pool result in the isolation of a peptide having the consensus and being flanked by two cysteins CNDRGFNC (SEQ ID NO: 101), i.e., 6 residue loop. Several such peptides deviated to different extents from the consensus suggesting that the presence of a disulphide compensated for other deviations from the consensus. See FIG. 11, FIG. 19, and FIG. 25.

H. Clonal Affinity Characterization

To obtain equilibrium binding curves, cells were labeled over a range of concentrations, e.g., about 0.1 to about 200 nM, of fluorescently conjugated target proteins (streptavidin-phycoerythrin or CRP-Alexa Fluor® 488) and analyzed by flow cytometry, as above. The corresponding mean fluorescence versus concentration data were fit to a monovalent binding isotherm to obtain the apparent $K_D$. Dissociation rates of streptavidin-binding clones were measured in the presence of about 1 to about 2 µM biotin. Cells were labeled with 50 nM streptavidin-phycoerythrin for 30 minutes at room temperature. The cells were then pelleted, resuspended in PBS with biotin, and immediately analyzed by flow cytometry. Fluorescence data were collected continuously for about five minutes. The dissociation rate constants were then determined as described previously. See Daugherty, P. S., et al. (1998) Protein Eng. 11(9):825-832, which is herein incorporated by reference.

For analysis of peptide affinity in a soluble scaffold, streptavidin-binding peptide SA-1 fused within a loop of YFP was prepared by cytoplasmic expression in *E. coli* strain FA113, induced overnight at room temperature. The soluble protein was isolated using B-PER II bacterial protein extraction reagent (Pierce Biotechnology, Rockford, Ill.) following the manufacturer's protocol. About 10$^7$ streptavidin coated magnetic beads (Dynal Inc., Brown Deer, Wis.) were added to 40 µl of cell lysate and equilibrated at room temperature for 20 minutes. The beads were washed once in 2 ml of PBS; biotin was added to a final concentration of 1 µM, and immediately analyzed by flow cytometry as above. Lysate from a strain expressing YFP with a T7•tag insertion at the same location was used as a negative control.

Example 2

OmpX Loop 2 and OmpX Loop 3 Expression Vectors

While the following protocol specifically describes the construction of vectors for the display of polypeptides and polypeptide libraries in loop 2 of OmpX, this procedure may be readily applied to loop 3 of OmpX, by consideration of the non-conserved regions in loop 3 as described in Table 3, by one skilled in the art. In loop 3, peptide insertions are preferred between residues 94-99, and preferably between residues 95-97, with Pro96 removed. The wild-type OmpX gene from *E. coli* MC1061:

```
                                          (SEQ ID NO: 102)
atgaaaaaaattgcatgtctttcagcactggccgcagttctggctttcac cgcaggtacttccgtagctgcgacttctactgtaactggcggttacgcac agagcgacgctcagggccaaatgaacaaaatgggcggtttcaacctgaaa taccgctatgaagaagacaacagcccgctgggtgtgatcggttctttcac ttacaccgagaaaagccgtactgcaagc/tctggtgactacaacaaaaac cagtactacggcatcactgctggtccggcttaccgcattaacgactgggc aagcatctacggtgtagtgggtgtgggttatggtaaattccagaccactg aatac/ccg/acctacaaacacgacaccagcgactacggtttctcctacg gtgcgggtctgcagttcaacccgatggaaaacgttgctctggacttctct tacgagcagagccgtattcgtagcgttgacgtaggcacctggattgccgg tgttggttaccgcttctaataa
``` was amplified using primer 1 and primer 2 introducing a KpnI cut site at the front of the gene and SfiI and HindIII cut sites at the end of the gene and inserted into pBAD33 using KpnI and HindIII digestions to create pB330mpX. Table 7 shows the primers used.

TABLE 7

| Primer | Description | Primer Sequence |
|---|---|---|
| 1 | OmpX forward w/ KpnI | ttcgagctcggtacctttgaggtggttatgaaaaaaattg (SEQ ID NO: 103) |
| 2 | OmpX reverse w/ SfiI, HindIII | aaaacagccaagcttggccaccttggccttattagaagcg gtaaccaacacc (SEQ ID NO: 104) |
| 3 | OmpX SfiI, T7tag loop2 forward | gcgagcatgaccggcggccagcagatgggtggcgggagtt ctggtgactacaacaaaaac (SEQ ID NO: 105) |
| 4 | OmpX SfiI, T7tag loop2 reverse | ctggccgccggtcatgctcgccatttggcccgactggccg cttgcagtacggcttttctc (SEQ ID NO: 106) |
| 5 | Making OmpX template | agaaaagccgtactgcaagcggcgggagttctggtgacta (SEQ ID NO: 107) |
| 6 | Ompx reverse w/ HindIII | tatctaagcttttattagaagcggtaaccaacacc (SEQ ID NO: 108) |
| 7 | OmpX 3C library | aagcaagctgcaagtccgaagcggccagtcgggccaanns nnsnnsnnstgcnnsnnsnnstgcnnsnnsnnsnnsggcg ggagttctggtgacta (SEQ ID NO: 109) |
| 8 | OmpX alpha CT library | tgcaagtccgaagcggccagtcgggccaannstgctgcnn snnsnnsnnstgcnnsnnsnnsnnsnnsnnsnnstgcnns ggcgggagttctggtgacta (SEQ ID NO: 110) |

Primer 1/primer 3 and primer 4/primer 2 were used in separate PCR reactions with pB33ompX as the template to produce fragments that were used in an overlap extension PCR.

The final product includes a SfiI site before a T7tag peptide epitope with four flanking residues on either side inserted within loop 2 of OmpX, resulting in a S74G substitution. The product was then digested with KpnI and HindIII and ligated to similarly digested pBAD33 to create pB33OmpX-T2. The pB33OmpX-T2 plasmid was then cut with SfiI to create the vector that was used to generate the OmpX libraries. The plasmid pB33OmpX-temp was created lacking the SfiI restriction sites and the T7 epitope that was used as the template for the PCR to generate the library insert. pB33OmpX-temp was made using PCR, using primer 5 and primer 6 to create a "megaprimer" with pB33OmpX-T2 as template. The megaprimer and primer 1 were then used in a PCR reaction with pB33OmpX-T2 as template. The product was digested with KpnI and HindIII and ligated to similarly digested pBAD33. Primer 7 and Primer 8 were used separately as the forward primers to create the various library inserts with primer 2 as the reverse primer and pB33OmpX-temp as the template. The product was digested with SfiI and ligated to similarly cut pBAD33OmpX-T2 to generate the OmpX display libraries.

Example 3

Circularly Permuted OmpX (CPX)

Figure 14:
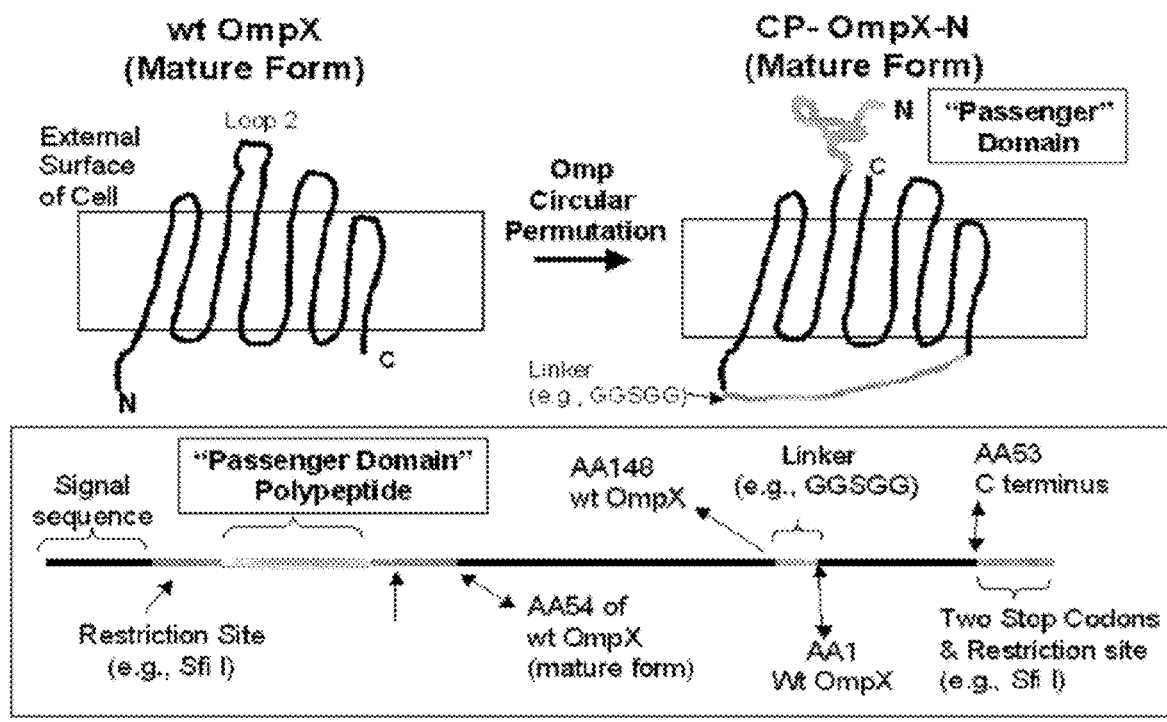
FIG. 14 shows an example of terminal fusion display using a topologically permuted Omp for polypeptide display exemplified using OmpX. Using PCR methods familiar to one skilled in the art, a rearranged gene sequence is assembled such that the order of the Omp polypeptide sequence is as shown in lower box in order to achieve N-terminal polypeptide display within a surface exposed loop. The linker sequence shown is SEQ ID NO:78.
Figure 15A:
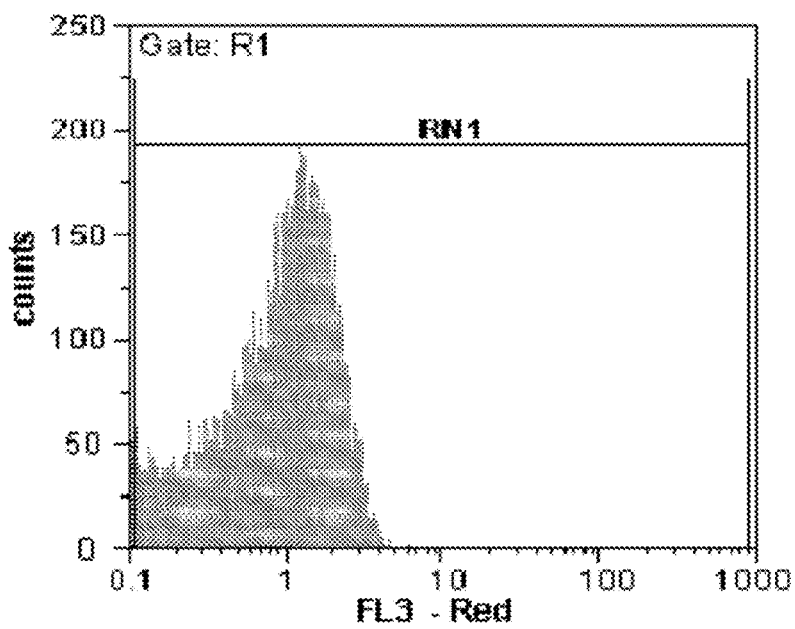
FIG. 15A shows flow cytometric analysis of control E. coli cells overexpressing OmpX. Cells were grown in LB growth medium, washed 1×, incubated with anti-T7tag monoclonal antibody, washed again, and incubated with 10 nM streptavidin phycoerythrin, and analyzed using flow cytometry.
Figure 15B:
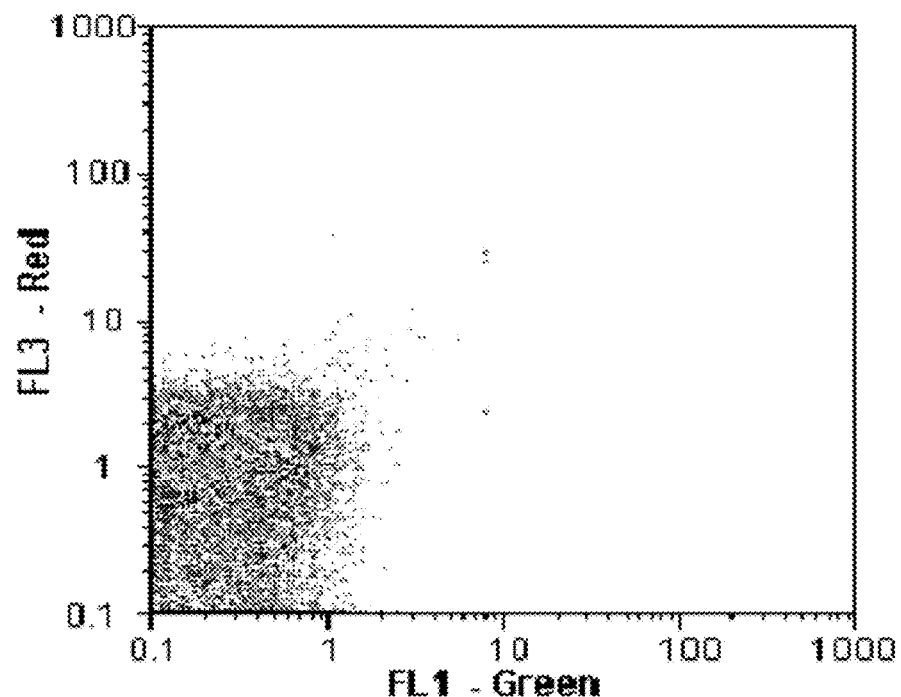
FIG. 15B shows a two-parameter plot of Green vs. Red fluorescence of the identical sample from 15A.
Figure 15C:
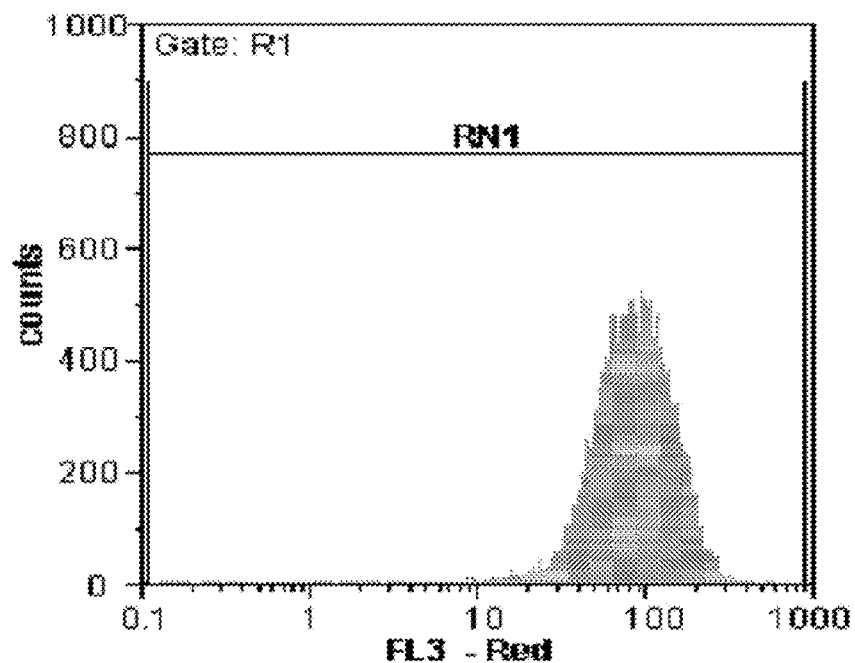
FIG. 15C shows *E. coli* displaying a T7tag peptide epitope recognized by a monoclonal antibody (MC1061/pCPX-T7). Cells were grown in liquid growth medium, washed 1× and incubated with anti-T7tag monoclonal antibody, washed again, and incubated with 10 nM streptavidin phycoerythrin, and analyzed using flow cytometry.
Figure 15D:
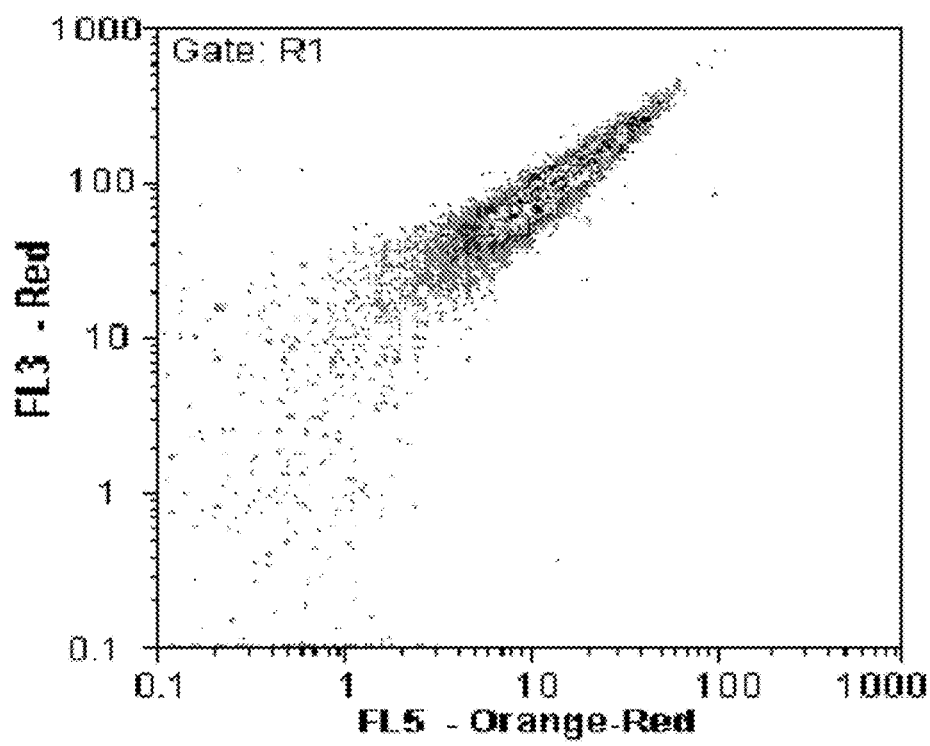
FIG. 15D shows a two-parameter plot of Green vs. Red fluorescence of the identical sample from 15C.

Display and expression of passenger polypeptides as N or C terminal fusions is accomplished by topological permutation of an Omp as shown in FIG. 14. Sequence rearrangement of an outer membrane protein, in this case OmpX, was accomplished using an overlap extension PCR methods known in the art in order to create either N or C terminal fusion constructs. See Ho, et al. (1989) Gene 77(1):51-59, which is herein incorporated by reference; and see FIG. 14, FIG. 27, FIG. 28, FIG. 30, and FIG. 32. Polypeptide passenger insertion points are chosen to occur within non-conserved, surface exposed loop sequences of surface exposed proteins, such as monomeric Omps (including OmpA, OmpX, OmpT, and the like) using methods known in the art.

The DNA sequence of the N/C terminal fusion expression vector provides the following contiguous components fused or linked in linear order from N to C terminus (See FIG. 14):

1. A DNA sequence encoding an N-terminal leader peptide, such as the native N-terminal leader peptide from an outermembrane localized protein (e.g., OmpX, OmpA, or the like,
2. A DNA restriction enzyme cleavage site (for efficient library construction),
3. A DNA sequence encoding given polypeptide to be expressed and displayed on the cell surface,
4. A DNA sequence encoding peptide linker, which may include entities commonly employed in the recombinant DNA and protein engineering arts, such as a proteolytic cleavage site that allows peptide release from the cell surface, and the like,
5. A carrier protein sequence beginning with the amino acid downstream, preferably immediately downstream, of the insertion point at which display is desired (e.g., wt OmpX aa 54) and ending with carrier's native-terminus excluding native stop codon(s),
6. A DNA sequence encoding a short, flexible peptide linker sequence (e.g., GGSGG (SEQ ID NO:78), or others known in the art),
7. A DNA sequence encoding the carrier protein's sequence beginning with the amino acid upstream, preferably immediately upstream, of the carrier's native leader peptide and ending with the amino acid upstream, preferably immediately upstream, of the chosen insertion site, and
8. Two stop codons for efficient termination followed by appropriate restriction enzyme cleavage sites (e.g., SfiI, or the like).

Terminal Fusion Expression Vectors

The following sequences and primers were used to construct the N/C terminal fusion expression vectors, and the resulting DNA sequences according to the specifications of FIG. 14 using methods known in the art:

Protein sequence of wild-type E. coli
pro-OmpX (pre-signal peptide cleavage):
(SEQ ID NO: 111)
(SS)MKKIACLSALAAVLAFTAGTSVAATSTVTGGYAQSDAQGQMNKMGG

FNLKYRYEEDNSPLGVIGSFTYTEKSRTAS/SGDYNKNQYYGITAGPAYR

INDWASIYGVVGVGYGKFQTTEY/P/TYKHDTSDYGFSYGAGLQFNPMEN

VALDFSYEQSRIRSVDVGTWIAGVGYRF**

DNA sequence of: wild-type E. coli OmpX
(SEQ ID NO: 112)
atgaaaaaaattgcatgtctttcagcactggccgcagttctggctttcac cgcaggtacttccgtagctgcgacttctactgtaactggcggttacgcac agagcgacgctcagggccaaatgaacaaatgggcggtttcaacctgaaa taccgctatgaagaagacaacagcccgctgggtgtgatcggttctttcac ttacaccgagaaaagccgtactgcaagc/tctggtgactacaacaaaaac cagtactacggcatcactgctggtccggcttaccgcattaacgactgggc aagcatctacggtgtagtgggtgtgggttatggtaaattccagaccactg aatac/ccg/acctacaaacacgacaccagcgactacggtttctcctacg gtgcgggtctgcagttcaacccgatggaaaacgttgctctggacttctct tacgagcagagccgtattcgtagcgttgacgtaggcacctggattgccgg tgttggttaccgcttctaataa A. Contiguous (Fused) DNA Sequences for the Display of the T7tag Peptide Epitope as an N-Terminal Fusion within OmpX Loop 2 (Between Amino Acids 53 and 54 of Mature OmpX):

(SEQ ID NO: 113)
(SS)atgaaaaaaattgcatgtctttcagcactggccgcagttctggctt tcaccgcaggtacttccgtagct-gcgacttctact (T7tag):
(SEQ ID NO: 114)
atggcgagcatgaccggcggccagcagatgggt (Linker):
(SEQ ID NO: 115)
ggaggccagtctggccag OmpX amino acids 54 to end (STOP):
(SEQ ID NO: 116)
tctggtgactacaacaaaaaccagtactacggcatcactgctggtccggc ttaccgcattaacgactgggcaagcatctacggtgtagtgggtgtgggtt atggtaaattccagaccactgaatacccgacctacaaacacgacaccagc gactacggtttctcctacggtgcgggtctgcagttcaacccgatggaaaa cgttgctctggacttctcttacgagcagagccgtattcgtagcgttgacg taggcacctggattgccggtgttggttaccgcttc Peptide Linker:
(SEQ ID NO: 117)
ggaggaagcgga OmpX aa 1 (first residue of structure)-53:
(SEQ ID NO: 118)
gcgacttctactgtaactggcggttacgcacagagcgacgctcagggcca aatgaacaaatgggcggtttcaacctgaaataccgctatgaagaagaca acagcccgctgggtgtgatcggttctttcacttacaccgagaaaagccgt actgcaagc Stop codons:
(SEQ ID NO: 119)
taataa Protein Sequence Resulting from Translation of the Above DNA Sequence=OmpX Signal Sequence/T7/SfiI/AA54/AA148/AA1/AA53:

(SEQ ID NO: 120)
MKKIACLSALAAVLAFTAGTSVA/MASMTGGQQMG/G/GQSGQ/SGDYNK

NQYYGITAGPAYRINDWASIYGVVGVGYGKFQTTEYPTYKHDTSDYGFSY

GAGLQFNPMENVALDFSYEQSRIRSVDVGTWIAGVGYRF/GGSG/ATSTV

TGGYAQSDAQGQMNKMGGFNLKYRYEEDNSPLGVIGSFTYTEKSRTAS**

B. Contiguous DNA Sequences for the Display of the T7 Epitope as a C-Terminal Fusion within OmpX Loop 3 (Between Amino Acids 95/97)

The order of the genetic elements encoding the C-terminal Loop 3 display vector is: signal sequence/OmpX 97-148/Linker/OmpX 1-95/Linker/T7tag peptide/stop codons: This fusion protein is encoded by the DNA sequence:

(SEQ ID NO: 121)
atgaaaaaaattgcatgtctttcagcactggccgcagttctggctttcac cgcaggtacttccgtagct/acctacaaacacgacaccagcgactacggt ttctcctacggtgcgggtctgcagttcaacccgatggaaaacgttgctct ggacttctcttacgagcagagccgtattcgtagcgttgacgtaggcacct ggattgccggtgttggttaccgcttc/ggaggaagcgga/gcgacttcta ctgtaactggcggttacgcacagagcgacgctcagggccaaatgaacaaa atgggcggtttcaacctgaaataccgctatgaagaagacaacagcccgct gggtgtgatcggttctttcacttacaccgagaaaagccgtactgcaagct ctggtgactacaacaaaaaccagtactacggcatcactgctggtccggct taccgcattaacgactgggcaagcatctacggtgtagtgggtgtgggtta tggtaaattccagaccactgaatac/ggaggaagcggaggaa/tggcgag catgaccggcggccagcagatgggt/taataa Protein Sequence Resulting from Translation of the DNA Sequence Immediately Above=Signal Peptide/AA97-AA148/Linker/AA1-AA95/Linker/T7tag:

(SEQ ID NO: 122)
MKKIACLSALAAVLAFTAGTSVA/TYKHDTSDYGFSYGAGLQFNPMENVA

LDFSYEQSRIRSVDVGTWIAGVGYRF/GGSG/ATSTVTGGYAQSDAQGQM

-continued
NKMGGFNLKYRYEEDNSPLGVIGSFTYTEKSRTASSGDYNKNQYYGITAG

PAYRINDWASIYGVVGVGYGKFQTTEY/GGSGGMASMTGGQQMG**

T7tag Peptide Encoding Sequence:

(SEQ ID NO: 123)
5'atggcgagcatgaccggcggccagcagatgggt (SEQ ID NO: 124)
MASMTGGQQMG Streptavidin Binding Peptide Encoding Sequence:

(SEQ ID NO: 125)
5'accgtgctgatttgcatgaacatctgttggacgggcgaaactcag (SEQ ID NO: 126)
TVLICMNICWTGETQ SacI and KpnI 5' Sites:

(SEQ ID NO: 127)
ttcgagctcggtacctttgaggtggtt

Signal Sequence:

(SEQ ID NO: 128)
Atgaaaaaaattgcatgtctttcagcactggccgcagttctggctttcac cgcaggtacttccgtaget (SEQ ID NO: 129)
MKKIACLSALAAVLAFTAGTSVA SfiI & Hind III 3' Sites:

(SEQ ID NO: 130)
ggccaaggtggccaagcttggctgtttt

Figure 29:
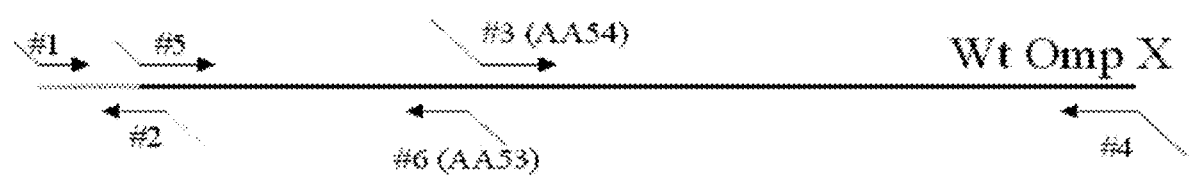
FIG. 29 shows primers used for the construction of N-terminal OmpX display vector. Primers are as follows.

C. Display of Peptides Binding to Streptavidin, T7-Tag Monoclonal Antibody, and C-Reactive Protein as N-Terminal Fusion Proteins To construct the N-terminal T7tag display vector, primers 1-14:

Primer (5'->3') 1:
Length 60 Melting Tm 48 Sense strand
(SEQ ID NO: 131)
ttcgagctcggtacctttgaggtggttatgaaaaaaattgcatgtctttc agcactggcc Primer (5'->3') 2:
Length 60 Melting Tm 49 Sense strand
(SEQ ID NO: 132)
tttcagcagtggccgcagttctggctttcaccgcaggtacttccgtagct atggcgagca Primer (5'->3') 3:
Length 60 Melting Tm 49 Sense strand
(SEQ ID NO: 133)
agctatggcgagcatgaccggcggccagcagatgggtggaggaagcggag gatctggtga Primer (5'->3') 4:
Length 60 Melting Tm 50 Sense strand
(SEQ ID NO: 134)
cggaggatctggtgactacaacaaaaaccagtactacggcatcactgctg gtccggctta Primer (5'->3') 5:
Length 60 Melting Tm 49 Sense strand
(SEQ ID NO: 135)
gctggtccggcttaccgcattaacgactgggcaagcatctacggtgtagt gggtgtgggt Primer (5'->3') 6:
Length 60 Melting Tm 50 Sense strand
(SEQ ID NO: 136)
gtagtgggtgtgggttatggtaaattccagaccactgaatacccgaccta caaacacgac Primer (5'->3') 7:
Length 60 Melting Tm 51 Sense strand
(SEQ ID NO: 137)
cgacctacaaacacgacaccagcgactacggtttctcctacggtgcgggt ctgcagttca Primer (5'->3') 8:
Length 60 Melting Tm 48 Sense strand
(SEQ ID NO: 138)
cgggtctgcagttcaacccgatggaaaacgttgctctggacttctcttac gagcagagcc Primer (5'->3') 9:
Length 60 Melting Tm 50 Sense strand
(SEQ ID NO: 139)
cttacgagcagagccgtattcgtagcgttgacgtaggcacctggattgcc ggtgttggtt Primer (5'->3') 10:
Length 60 Melting Tm 48 Sense strand
(SEQ ID NO: 140)
Tgccggtgttggttaccgcttcggaggaagcggagcgacttctactgtaa ctggcggtta Primer (5'->3') 11:
Length 60 Melting Tm 48 Sense strand
(SEQ ID NO: 141)
Ctgtaactggcggttacgcacagagcgacgctcagggccaaatgaacaaa atgggcggtt Primer (5'->3') 12:
Length 60 Melting Tm 51 Sense strand
(SEQ ID NO: 142)
Acaaaatgggcggtttcaacctgaaataccgctatgaagaagacaacagc ccgctgggtg Primer (5'->3') 13:
Length 60 Melting Tm 49 Sense strand
(SEQ ID NO: 143)
gcccgctgggtgtgatcggttctttcacttacaccgagaaaagccgtact gcaagctaat Primer (5'->3') 14:
Length 47 Melting Tm 49 Antisense strand
(SEQ ID NO: 144)
aaaacagccaagcttggccaccttggccttattagcttgcagtacgg and the numbering scheme corresponding to FIG. 28 and FIG. 29, were used in standard PCR using methods known in the art to give the following sequences:

5'flank & Signal sequence:
(SEQ ID NO: 145)
/ttcgagctcggtacctttgaggtggtt/atgaaaaaaattgcatgtctt
tcagcactggccgcagttctggctttcaccgcaggtacttccgtagct/ nt1-159:
(SEQ ID NO: 146)
/gcgacttctactgtaactggcggttacgcacagagcgacgctcagggcc
aaatgaacaaaatgggcggtttcaacctgaaataccgctatgaagaagac
aacagcccgctgggtgtgatcggttctttcacttacaccgagaaaagccg
tactgcaagc/ nt160-285:
(SEQ ID NO: 147)
tctggtgactacaacaaaaaccagtactacggcatcactgctggtccggc
ttaccgcattaacgactgggcaagcatctacggtgtagtgggtgtgggtt
atggtaaattccagaccactgaatac/ccg/ nt289-441:
(SEQ ID NO: 148)
acctacaaacacgacaccagcgactacggtttctcctacggtgcgggtct
gcagttcaacccgatggaaaacgttgctctggacttctcttacgagcaga
gccgtattcgtagcgttgacgtaggcacctggattgccggtgttggttac
cgcttc/taataa The above PCR fragments are then fused using overlap extension PCR reactions using primers 1-14 according to the scheme of FIG. 25, resulting in the full length N-terminal T7tag display vector encoded by the following:

(SEQ ID NO: 149)
5'ttcgagctcggtacctttgaggtggtt/atgaaaaaaattgcatg
tctttcagcactggccgcagttctggctttcaccgcaggtacttccgtag
ct/gcgacttctact/atggcgagcatgaccggcggccagcagatgggt/
ggaggccagtctggccag/tctggtgactacaacaaaaaccagtactacg
gcatcactgctggtccggcttaccgcattaacgactgggcaagcatctac
ggtgtagtgggtgtgggttatggtaaattccagaccactgaatac/ccg/
acctacaaacacgacaccagcgactacggtttctcctacggtgcgggtct
gcagttcaacccgatggaaaacgttgctctggacttctcttacgagcaga
gccgtattcgtagcgttgacgtaggcacctggattgccggtgttggttac
cgcttc/ggaggaagcgga/gcgacttctactgtaactggcggttacgca
cagagcgacgctcagggccaaatgaacaaaatgggcggtttcaacctgaa
ataccgctatgaagaagacaacagcccgctgggtgtgatcggttctttca
cttacaccgagaaaagccgtactgcaagc/taataa 3'

D. To Construct the N-Terminal Loop 2 According to FIGS. 28 and 29 and C-Terminal Loop-3 Display Vectors According to FIG. 30 and FIG. 31 the Following DNA Sequences:

5'flanking & Signal sequences (Prime w/PSD 515):
(SEQ ID NO: 150)
ttcgagctcggtacctttgaggtggtt/atgaaaaaaattgcatgtctt
cagcactggccgcagttctggctttcaccgcaggtacttccgtagct nt1-159:
(SEQ ID NO: 151)
gcgacttctactgtaactggcggttacgcacagagcgacgctcagggcca
aatgaacaaaatgggcggtttcaacctgaaataccgctatgaagaagaca
acagcccgctgggtgtgatcggttctttcacttacaccgagaaaagccgt
actgcaagc nt160-285:
(SEQ ID NO: 152)
tctggtgactacaacaaaaaccagtactacggcatcactgctggtccggc
ttaccgcattaacgactgggcaagcatctacggtgtagtgggtgtgggtt
atggtaaattccagaccactgaatac nt289-441:
(SEQ ID NO: 153)
acctacaaacacgacaccagcgactacggtttctcctacggtgcgggtct
gcagttcaacccgatggaaaacgttgctctggacttctcttacgagcaga
gccgtattcgtagcgttgacgtaggcacctggattgccggtgttggttac
cgcttctaataa were synthesized, and overlapped using PCR using the following primers 1-16:

Primer (5'->3') 1: Length 45 Melting Tm 49 Sense strand:
(SEQ ID NO: 154)
ttcgagctcggtacctttgaggtggttatgaaaaaaattgcatgt Primer (5'->3') 2: Length 57 Melting Tm 48 Antisense strand:
(SEQ ID NO: 155)
gcggtgaaagccagaactgcggccagtgctgaaagacatgcaatttttt
cataacc Primer (5'->3') 3: Length 57 Melting Tm 48 Sense strand:
(SEQ ID NO: 156)
tggctttcaccgcaggtacttccgtagctacctacaaacacgacaccagc
gactacg Primer (5'->3') 4: Length 57 Melting Tm 49 Antisense strand:
(SEQ ID NO: 157)
ttttccatcgggttgaactgcagacccgcaccgtaggagaaaccgtagtc
gctggtg Primer (5'->3') 5: Length 57 Melting Tm 48 Sense strand:
(SEQ ID NO: 158)
ttcaacccgatggaaaacgttgctctggacttctcttacgagcagagccg
tattcgt Primer (5'->3') 6: Length 57 Melting Tm 50 Antisense strand:
(SEQ ID NO: 159)
gcggtaaccaacaccggcaatccaggtgcctacgtcaacgctacgaatac
ggctctg Primer (5'->3') 7: Length 57 Melting Tm 48 Sense strand:
(SEQ ID NO: 160)
ggtgttggttaccgcttcggaggaagcggagcgacttctactgtaactgg
cggttac -continued Primer (5'->3') 8: Length 57 Melting Tm 48
Antisense strand:
(SEQ ID NO: 161)
ccgcccatttttgttcatttggccctgagcgtcgctctgtgcgtaaccgcc agttaca Primer (5'->3') 9: Length 57 Melting Tm 49 Sense
strand:
(SEQ ID NO: 162)
gaacaaaatgggcggtttcaacctgaaataccgctatgaagaagacaaca gcccgct Primer (5'->3') 10: Length 57 Melting Tm 51
Antisense strand:
(SEQ ID NO: 163)
cagtacggcttttctcggtgtaagtgaaagaaccgatcacacccagcg ggctgttgt Primer (5'->3') 11: Length 57 Melting Tm 49 Sense
strand:
(SEQ ID NO: 164)
cgagaaaagccgtactgcaagctctggtgactacaacaaaaaccagt actacggcat Primer (5'->3') 12: Length 57 Melting Tm 51
Antisense strand:
(SEQ ID NO: 165)
tgcttgcccagtcgttaatgcggtaagccggaccagcagtgatgccgt agtactggt Primer (5'->3') 13: Length 57 Melting Tm 49 Sense
strand:
(SEQ ID NO: 166)
cgactgggcaagcatctacggtgtagtgggtgtgggttatggtaaattc cagaccac Primer (5'->3') 14: Length 57 Melting Tm 48
Antisense strand:
(SEQ ID NO: 167)
ccggtcatgctcgccattcctccgcttcctccgtattcagtggtctgga atttacca Primer (5'->3') 15: Length 57 Melting Tm 49 Sense
strand:
(SEQ ID NO: 168)
cgagcatgaccggcggccagcagatgggttaataaggccaaggtggcca agcttggc Primer (5'->3') 16: Length 19 Melting Tm 49
Antisense strand:
(SEQ ID NO: 169)
aaaacagccaagcttggcc according to the scheme of FIG. 30, resulting in the full length C-terminal display vector encoded by:

(SEQ ID NO: 170)
ttcgagctcggtacctttgaggtggttatgaaaaaaattgcatgtctttc agcactggccgcagttctggctttcaccgcaggtacttccgtagct/acc tacaaacacgacaccagcgactacggtttctcctacggtgcgggtctgca gttcaacccgatggaaaacgttgctctggacttctcttacgagcagagcc gtattcgtagcgttgacgtaggcacctggattgccggtgttggttaccgc ttc/ggaggaagcgga/gcgacttctactgtaactggcggttacgcacag agcgacgctcagggccaaatgaacaaaatgggcggtttcaacctgaaata ccgctatgaagaagacaacagcccgctgggtgtgatcggttctttcactt acaccgagaaaagccgtactgcaagc/tctggtgactacaacaaaaacca gtactacggcatcactgctggtccggcttaccgcattaacgactgggcaa gcatctacggtgtagtgggtgtgggttatggtaaattccagaccactgaa tac/ggaggaagcggagga/atggcgagcatgaccggcggccagcagatg ggt/taataa E. Construction of an OmpX Display Scaffold Utilizing Only 19 of the 20 Standard Amino Acids, i.e., No Leucine Codons Plasmid pB33NLXT2 (No Leucine OmpX with T7tag in loop 2) was isolated from a no leucine OmpX library (NLL) constructed in plasmid expression vector pBAD33OmpX-T7tag-L2, which encodes OmpX with the T7tag peptide inserted into Loop 2, under the transcriptional control of the arabinose promoter (B), on a low-copy plasmid possessing a p15A origin of replication. by selecting with FACS for T7tag display in a leucine auxotroph (MC1061) grown in minimal medium lacking leucine. This OmpX variant contains the mutations L17V, L14V, L10V, L26V, L37I, L113V, L123V, wherein the amino acid numbering is based on the mature form of wild type OmpX.

The "no leucine" library used above, allowing valine or isoleucine at each leucine codon, was constructed by performing overlap extension PCR, using methods known in the art. Plasmid pB33XT2 was used as a template for three separate reactions with primers PD674/675, PD676/677, and PD678/180. See Table 8.

TABLE 8

| primer | sequence |
|---|---|
| PD179 | tcgcaactctctactgtttc (SEQ ID NO: 171) |
| PD180 | ggctgaaaatcttctctc (SEQ ID NO: 172) |
| PD515 | ttcgagctcggtacctttgaggtggttatgaaaaaaattg (SEQ ID NO: 173) |
| PD632 | cagtagaagtcgctccgcttcctccgaagcggtaaccaacaccgg (SEQ ID NO: 174) |
| PD633 | ggaggaagcggagcgacttctactgtaactggcggttacgcacag (SEQ ID NO: 175) |
| PD634 | aaaacagccaagcttggccaccttggccttattagcttgcagtacggcttttctcg (SEQ ID NO: 176) |

TABLE 8-continued

| primer | sequence |
|---|---|
| PD674 | gttatgaaaaaaattgcatgtrtttcagcarttgccgcagttrttgctttcaccgcaggt (SEQ ID NO: 177) |
| PD675 | tgttgtcttcttcatagcggtatttaaygttgaaaccgcccattttgt (SEQ ID NO: 178) |
| PD676 | ccgctatgaagaagacaacagcccgrttggtgtgatcggttctttcac (SEQ ID NO: 179) |
| PD677 | aacgttttccatcgggttgaactgaayacccgcaccgtaggagaaac (SEQ ID NO: 180) |
| PD678 | ttcaacccgatggaaaacgttgctrttgacttctcttacgagcagag (SEQ ID NO: 181) |
| PD703 | ctgcccagactgccctccctggccagactggccagctacggaagtacctgc (SEQ ID NO: 182) |
| PD704 | ggagggcagtctgggcagtctggtgactacaacaaa (SEQ ID NO: 183) |
| PD707 | ctgactgaggccagtctggccagnnsnnstgcnnsnnsnnsnnsnnsnnstgcnnsnn sggagggcagtctgggcag (SEQ ID NO: 184) |
| PD753 | gctttcaccgcaggtacttctgactgaggccagtctggcc (SEQ ID NO: 185) |

The resulting products were purified, pooled, and amplified in a second round with primers PD515/180. The product was digested with KpnI/HindIII (as well as DpnI and PstI to remove template carryover), repurified, and ligated to the large fragment of pBAD33 that had been digested with KpnI/HindIII.

Plasmid pB33NLCPX (No Leucine Circularly Permuted OmpX in pBAD33) was constructed by PCR amplification of pB33NLXT2 in three reactions with PD515/703, PD704/632, and PD633/634. The fragments generated were each purified and pooled in a second round overlap reaction with outside primers PD515/634. The resulting product was then purified, digested with KpnI/HindIII (as well as DpnI to remove template carryover), repurified, and ligated to the large fragment of pBad33 that had been digested with KpnI/HindIII.

F. Construction of an N-Terminal Peptide Library within Loop 2 of NLCPX.

The NLCPX-C7C library was constructed by PCR amplification of pB33NLCPX with primers PD707/180. The product was diluted 25-fold into a fresh PCR with primers PD753/180, in order to extend the length of the fragment on the 5' end. The resulting product was purified, digested with SfiI, repurified, and ligated to the large fragment resulting from digestion of pB33NLCPX with SfiI/HincII. The ligation mixture is then transformed into electrocompetent *E. coli* MC1061 cells using electroporation, and cells are grown overnight in LB supplemented with glucose, resulting in the N-terminal peptide display library which can be aliquoted or further amplified by growth.

G. Non-Canonical Amino Acid Analogs

Non-canonical amino acid analogs which can be recognized and incorporated by the native or engineered cellular translational machinery, can be displayed more efficiently by redesigning the scaffolds described herein as follows. See Link, A. J. et al. (2003) Curr. Opin. Biotechnol. 14(6):604, which is herein incorporated by reference. All codons corresponding to one or more native amino acids are removed by first constructing an Omp gene variant library via gene assembly mutagenesis in which all of the codons in are randomized to generate codons that encode alternative amino acids. See Bessette, et al. (2003) Methods. Mol. Biol. 231:29-37, which is herein incorporated by reference. Selection or screening is then used to isolate Omp variants that efficiently display a passenger protein in the absence of the corresponding natural amino acid.

For example, to create a scaffold that efficiently displays the leucine analog trifluoroleucine, all leucine codons were randomized such that they could encode valine or isoleucine at each position. This library was sorted by FACS for T7tag display in medium comprising 19 standard amino acids (no leucine) supplemented with trifluoroleucine. One of the resulting clones (NLOmpX T7tag) exhibits T7tag display in media lacking leucine at a level equivalent to media with 20 amino acids. In contrast, the wild-type OmpX scaffold exhibits a substantially reduced level of display of the epitope in 19 amino acids. This mutant OmpX sequence (NLOmpX) has all leucine codons replaced with valine, except at position 37 of the mature protein, which is replaced with isoleucine. Using the NLOmpX as a starting point for creating and screening a library allows for the ability to perform negative selections in media lacking leucine, in order to remove binders that do not contain leucine codons.

A scaffold deficient in at least one of the 20 standard amino acids, e.g., is preferred for screening libraries that incorporated analogs of the deficient amino acid. The reason is that with too many leucine codons in the OmpX DNA sequence, the removal of leucine, and addition of a leucine analog, such as trifluoroleucine, inhibits the expression of the carrier OmpX. See FIG. 34. Thus, wild-type OmpX can not be made without Leu in the medium, but with leucine present, the leucine analog can not be incorporated since the rates of incorporation are different. Therefore, removing the leucines from the scaffold (OmpX) allows scaffold synthesis without any leucine present. As a result, one may readily screen for polypeptide libraries that incorporate leucine analogs.

Example 4

Assay Using the Expression Vectors

The following two strategies were used to isolate sequences which bind to tumor cells, and potentially internalize. First, the bacterial display library was selected for binding by incubation with tumor cells, and selective sedimentation of tumor cells. A single round of enrichment by sedimentation was used to enrich binding or internalizing sequences. Two additional rounds were performed incorporating a step designed to selectively kill extracellular bacteria with the antibiotic gentamycin. Intracellular bacteria were then recovered by osmotic shock conditions resulting in preferential tumor cell lysis. The two rounds of selection incorporating a gentamycin selection steps resulted in a further increase in the percentage of green tumor cells in the FACS invasion assay. See FIG. 23. After the first three rounds of enrichment by simple co-sedimentation of bacteria adhering to tumor cells and gentamycin selection, a GFP expression vector was electroporated into each of the library pools resulting from each round to monitor selection success the remaining library population to facilitate quantitative and efficient FACS screening. See FIG. 23. Two rounds of FACS screening provided additional enrichment. See FIG. 20. After five rounds of selection for internalization into ZR-75-1 tumor cell line, (ATCC No. CRL-1500) from ATCC (Manassas, Va.), single clones were isolated and assayed for their internalization efficiency, as suggested by the gentamycin protection assay. The isolated clones exhibited up to about a 200-fold (0.005→1.0%) increased ability to internalize into the target cell lines, relative to negative controls. The sequences of a panel of isolated sequences from round 5 are presented in FIG. 7.

To demonstrate that peptides selected by bacterial display bound specifically to tumor cells, bacterial cells displaying tumor targeting peptides, and expressing an autofluorescent protein, e.g., EGFP, were incubated with tumor cells for one hour. Non-bound cells were washed from the tumor cell surfaces and images were acquired using fluorescence microscopy. See FIG. 14. Tumor cells incubated with OmpA displaying bacteria only, were non-fluorescent (FIG. 14), while tumor targeting peptide displaying bacteria bound specifically to tumor cell clumps (ZR-75-1). Therefore, fluorescent protein expressing, peptide displaying bacteria can be used as an infinitely renewable diagnostic reagents in a variety of assay platforms known to one skilled in the art, such as ELISA, fluorescence microscopy, and flow cytometry.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A method for identifying a target in a sample, the method comprising:
   (a) contacting the sample with a plurality of fusion proteins, wherein each fusion protein of the plurality comprises an outer membrane protein and a passenger polypeptide,
      (i) wherein a native N-terminus and a native C-terminus of each outer membrane protein are joined by a linker,
      (ii) wherein each outer membrane protein comprises a non-native N-terminus and a non-native C-terminus derived from an extracellular loop of the outer membrane protein, and
      (iii) wherein each passenger polypeptide is fused to the non-native N-terminus or the non-native C-terminus of its outer membrane protein; and
   (b) detecting a specific interaction between at least one of the passenger polypeptides of the plurality of fusion proteins and the target, wherein the presence of the specific interaction is indicative of the presence of the target in the sample,
   wherein each outer membrane protein is a bacterial outer membrane protein OmpA or OmpX.

2. The method of claim 1, wherein each passenger polypeptide is a substrate for an enzyme.

3. The method of claim 1, wherein at least one of the passenger polypeptides comprises a peptide ligand.

4. The method of claim 1, wherein each fusion protein comprises a label.

5. The method of claim 4, wherein at least one of the labels comprises a fluorescent agent.

6. The method of claim 4, wherein at least one of the labels comprises an affinity tag.

7. The method of claim 4, wherein at least one of the labels is C-terminal to the fusion protein.

8. The method of claim 4, wherein at least one of the labels is N-terminal to the fusion protein.

9. The method of claim 1, wherein each passenger polypeptide is linked or fused directly to the non-native C-terminus of the outer membrane protein.

10. The method of claim 1, wherein each passenger polypeptide is linked or fused directly to the non-native N-terminus of the outer membrane protein.

11. The method of claim 1, wherein each fusion protein is disposed in an outer membrane of a host cell, and wherein at least one of the non-native N-terminus and the non-native C-terminus of each fusion protein is positioned extracellularly.

12. The method of claim 11, wherein the non-native N-terminus is positioned extracellularly.

13. The method of claim 11, wherein the non-native C-terminus is positioned extracellularly.

14. The method of claim 11, wherein both the non-native C-terminus and the non-native N-terminus are positioned extracellularly.

15. The method of claim 11, wherein the host cell is a bacterial cell, a yeast cell or a mammalian cell.

16. The method of claim 15, wherein the host cell is a bacterial cell.

17. The method of claim 16, wherein the bacterial cell is an *Escherichia coli* cell.

* * * * *